United States Patent
Cobbold

(10) Patent No.: US 10,035,856 B2
(45) Date of Patent: Jul. 31, 2018

(54) FUNCTIONAL ANTIBODY FRAGMENT COMPLEMENTATION FOR A TWO-COMPONENTS SYSTEM FOR REDIRECTED KILLING OF UNWANTED CELLS

(71) Applicant: Revitope Limited, London (GB)

(72) Inventor: Mark Cobbold, Winchester, MA (US)

(73) Assignee: Revitope Limited, London (GB)

( * ) Notice: Subject to any disclaimer, the term of this patent is extended or adjusted under 35 U.S.C. 154(b) by 0 days.

(21) Appl. No.: 15/355,511

(22) Filed: Nov. 18, 2016

(65) Prior Publication Data

US 2017/0152316 A1 Jun. 1, 2017

Related U.S. Application Data

(60) Provisional application No. 62/270,907, filed on Dec. 22, 2015, provisional application No. 62/257,552, filed on Nov. 19, 2015.

(51) Int. Cl.
*A61K 38/00* (2006.01)
*C07K 16/28* (2006.01)
*C07K 16/18* (2006.01)
*A61K 39/395* (2006.01)
*A61K 39/00* (2006.01)

(52) U.S. Cl.
CPC .......... *C07K 16/2809* (2013.01); *C07K 16/18* (2013.01); *C07K 16/2863* (2013.01); *A61K 38/00* (2013.01); *A61K 39/39558* (2013.01); *A61K 2039/505* (2013.01); *C07K 2317/31* (2013.01); *C07K 2317/622* (2013.01)

(58) Field of Classification Search
CPC .............. A61K 38/00; A61K 39/39558; A61K 2039/505
See application file for complete search history.

(56) References Cited

U.S. PATENT DOCUMENTS

| | | | |
|---|---|---|---|
| 5,585,089 | A | 12/1996 | Queen et al. |
| 5,693,762 | A | 12/1997 | Queen et al. |
| 5,739,116 | A | 4/1998 | Hamann et al. |
| 5,767,285 | A | 6/1998 | Hamann et al. |
| 5,773,001 | A | 6/1998 | Hamann et al. |
| 7,151,164 | B2 | 12/2006 | Hansen et al. |
| 7,659,241 | B2 | 2/2010 | Senter et al. |
| 7,884,184 | B2 | 2/2011 | De Groot et al. |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 9,102,736 | B2 | 8/2015 | Hofmeister et al. |
| 9,120,853 | B2 | 9/2015 | Lowman et al. |
| 9,127,053 | B2 | 9/2015 | West et al. |
| 9,169,321 | B2 | 10/2015 | Daugherty et al. |
| 9,453,078 | B2 | 9/2016 | Stagliano et al. |
| 2004/0001853 | A1 | 1/2004 | George et al. |
| 2004/0197336 | A1 | 10/2004 | Self |
| 2005/0037001 | A1 | 2/2005 | Germeraad et al. |
| 2006/0045881 | A1 | 3/2006 | Molldrem |
| 2006/0088522 | A1 | 4/2006 | Boghaert et al. |
| 2008/0107660 | A1 | 5/2008 | Self |
| 2009/0130106 | A1 | 5/2009 | Christopherson et al. |
| 2009/0214543 | A1 | 8/2009 | Zangemeister-Wittke et al. |
| 2009/0304719 | A1* | 12/2009 | Daugherty ......... C07K 16/2818 424/178.1 |
| 2010/0189651 | A1 | 7/2010 | Stagliano et al. |
| 2010/0291082 | A1 | 11/2010 | Zurawski et al. |
| 2011/0008840 | A1 | 1/2011 | Hoffee et al. |
| 2011/0178279 | A1 | 7/2011 | Williams et al. |
| 2011/0229476 | A1 | 9/2011 | Liu et al. |
| 2013/0266568 | A1 | 10/2013 | Brinkmann et al. |
| 2013/0267686 | A1 | 10/2013 | Brinkmann et al. |
| 2013/0309230 | A1 | 11/2013 | Stagliano et al. |
| 2014/0023664 | A1 | 1/2014 | Lowman et al. |
| 2014/0024810 | A1 | 1/2014 | Stagliano et al. |
| 2014/0255313 | A1 | 9/2014 | Vasiljeva et al. |
| 2014/0363430 | A1 | 12/2014 | West et al. |
| 2015/0005477 | A1 | 1/2015 | Lowman et al. |
| 2015/0079088 | A1 | 3/2015 | Lowman et al. |
| 2015/0079093 | A1 | 3/2015 | Stuhler |
| 2015/0087810 | A1 | 3/2015 | Moore et al. |
| 2015/0118254 | A1 | 4/2015 | Lowman et al. |
| 2015/0183875 | A1 | 7/2015 | Cobbold et al. |
| 2015/0218217 | A1 | 8/2015 | Moore et al. |
| 2015/0307564 | A1 | 10/2015 | Young et al. |
| 2016/0009817 | A1 | 1/2016 | Wang et al. |
| 2016/0039942 | A1 | 2/2016 | Cobbold et al. |
| 2016/0122425 | A1 | 5/2016 | Daugherty et al. |
| 2016/0144042 | A1 | 5/2016 | Williams et al. |
| 2016/0152711 | A1 | 6/2016 | Williams et al. |
| 2016/0228546 | A1 | 8/2016 | Stagliano et al. |
| 2017/0081397 | A1 | 3/2017 | Stagliano et al. |

FOREIGN PATENT DOCUMENTS

| | | | |
|---|---|---|---|
| EP | 0659438 | A1 | 6/1995 |
| EP | 0871673 | B1 | 4/2006 |

(Continued)

OTHER PUBLICATIONS

Shearer et al. (J. Immunol. Aug. 1, 1990; 145 (3): 932-9).*

(Continued)

*Primary Examiner* — Stephen Rawlings
(74) *Attorney, Agent, or Firm* — McNeill Baur PLLC

(57) ABSTRACT

A targeted T-cell engaging agent for treating a condition characterized by the presence of unwanted cells includes (a) a targeting moiety that is capable of targeting the unwanted cells; (b) a first T-cell engaging domain capable of T-cell engaging activity when binding a second T-cell engaging domain, wherein the second T-cell engaging domain is not part of the agent; (c) at least one inert binding partner capable of binding to the first T-cell engaging domain such that the first T-cell engaging domain does not bind to the second T-cell engaging domain unless the inert binding partner is removed; and (d) at least one cleavage site separating the first T-cell engaging domain and the inert binding partner, wherein the cleavage site is: (i) cleaved by an enzyme expressed by the unwanted cells; (ii) cleaved through a pH-sensitive cleavage reaction inside the unwanted cell; (iii) cleaved by a complement-dependent cleavage reaction; or (iv) cleaved by a protease that is colocalized to the unwanted cell by a targeting moiety that is the same or different from the targeting moiety in the agent.

16 Claims, 20 Drawing Sheets

(56) References Cited

FOREIGN PATENT DOCUMENTS

| | | |
|---|---|---|
| EP | 1948802 A1 | 7/2008 |
| EP | 1664270 B1 | 5/2014 |
| GB | 1216649 | 3/2014 |
| WO | 9517212 A | 6/1995 |
| WO | 1995017212 A1 | 6/1995 |
| WO | 1996034892 A1 | 11/1996 |
| WO | 1997023237 A1 | 7/1997 |
| WO | 1998010651 A1 | 3/1998 |
| WO | 1998018493 A2 | 5/1998 |
| WO | 1998024478 A2 | 6/1998 |
| WO | 1998041641 A1 | 9/1998 |
| WO | 1999002175 A1 | 1/1999 |
| WO | 00006605 | 2/2000 |
| WO | 0244197 | 6/2002 |
| WO | 2003027135 A2 | 4/2003 |
| WO | 2004069876 A2 | 8/2004 |
| WO | 2005052004 A2 | 6/2005 |
| WO | 2005061547 A2 | 7/2005 |
| WO | 2005083431 A2 | 9/2005 |
| WO | 2005087813 A1 | 9/2005 |
| WO | 2007057922 A1 | 5/2007 |
| WO | 2007107764 A1 | 9/2007 |
| WO | 2008019366 A2 | 2/2008 |
| WO | 2008052322 A1 | 5/2008 |
| WO | 2008097866 A2 | 8/2008 |
| WO | 2009024771 A2 | 2/2009 |
| WO | 2009025846 A2 | 2/2009 |
| WO | 2008063113 | 7/2009 |
| WO | 2010037837 A2 | 4/2010 |
| WO | 2010081173 A2 | 7/2010 |
| WO | 2011056721 A2 | 5/2011 |
| WO | 2012123755 A1 | 9/2012 |
| WO | 2013104804 A2 | 7/2013 |
| WO | WO2013123061 A1 * | 8/2013 |
| WO | 2013128194 A1 | 9/2013 |
| WO | 2013139789 A1 | 9/2013 |
| WO | 2015001361 A1 | 1/2015 |
| WO | 2016014974 A2 | 1/2016 |

OTHER PUBLICATIONS

Sandor et al. (Immunol. Today. May 1993; 14 (5): 227-31).*
Thompson et al. (MAbs. Jul.-Aug. 2009; 1 (4): 348-356).*
Self et al. (Nat. Med. Jul. 1996; 2 (7): 817-20).*
Shapira et al. (PLoS One. 2012; 7 (2): e32320; pp. 1-17).*
Yang et al. (MAbs. 2015; 7 (2): 440-50).*
Desnoyers et al. (Sci. Transl. Med. Oct. 16, 2013; 5 (207): 207ra144; pp. 1-10).*
Choi et al. (Expert Opin. Biol. Ther. Jul. 2011; 11 (7): 843-53).*
Polu et al. (Expert Opin. Biol. Ther. Aug. 2014; 14 (8): 1049-53).*
Watanabe et al. (Oncol. Rep. Oct. 2011; 26 (4): 949-55).*
Donaldson et al. (Cancer Biol. Ther. Nov. 2009; 8 (22): 2147-52).*
Igawa et al. (Protein Eng. Des. Sel. Aug. 2010; 23 (8): 667-77).*
Liu et al. (MAbs. Jan.-Feb. 2012; 4 (1): 17-23).*
Sandersjöö et al. (Cell. Mol. Life Sci. Apr. 2015; 72 (7): 1405-15).*
Abhinandan KR and Martin AC, Protein Eng Des Sel. 23(9):689-97 (2010).
Adis R&D Profile: Brentuximab Vedotin, Drugs RD 11(1):85-95 (2011).
Akiyama et al., "Characterization of cytomegalovirus pp65-HLA-A24 peptide-specific CTL lines from metastatic melanoma patients", Oncology Reports 22: pp. 185-191 (Mar. 3, 2009).
Alderson RF, et al. CAT-8015: a second-generation pseudomonas exotoxin A-based immunotherapy targeting CD22-expressing hematologic malignancies. Clin Cancer Res. 15(3):832-9. Feb. 1, 2009.
Alegretti AP, et al. Expression of CD55 and CD59 on peripheral blood cells from systemic lupus erythematosus (SLE) patients. Cell Immunol. 265(2):127-32.2010; Epub Aug. 2, 2010.
Alexander, J., et al., "Linear PADRE T Helper Epitope and Carbohydrate B Cell Epitope Conjugates Induce Specific High Titer IgG Antibody Responses," J. Immunol. 164:1625-1633 (2000).

Alisa A, et al. "Human CD4(+) T cells recognize an epitope within alpha-fetoprotein sequence and develop into TGF-beta-producing CD4(+) T cells," J Immunol. Apr. 1, 2008;180(7):5109-17.
Appay V. The physiological role of cytotoxic CD4(+) T-cells: the holy grail? Clin Exp Immunol. 138(1):10-13. 2004.
Arai K, et al., "Preventing effect of anti-ICAM-1 and anti-LFA-1 monoclonal antibodies on murine islet allograft rejection," International Journal of Pancreatology, Aug. 1999, vol. 26, Issue 1, pp. 23-31.
Ariel O, et al. Signal transduction by CD58: the transmembrane isoform transmits signals outside lipid rafts independently of the GPI-anchored isoform. Cell Signal. 21(7):1100-8. Jul. 2009. Epub Mar. 5, 2009.
Baeuerle P.A., et al. "BiTE: Teaching antibodies to engage T-cells for cancer therapy." Curr Opin Mol Therapeutics. 11(1):22-30. (Feb. 1, 2009).
Baeuerle, P.A. and Reinhardt, C., "Bispecific T-Cell Engaging Antibodies for Cancer Therapy," Cancer Res. 69( 12):4941-4944 (2009).
Bargou, R., et al., "Tumor Regression in Cancer Patients by Very Low Doses of a T-Cell Engaging Antibody," Science 321:974-977 (2008).
Becker-Herman S, et al. CD74 is a member of the regulated intramembrane proteolysis-processed protein family. Mol Biol Cell. 16(11):5061-9. Nov. 2005. Epub Aug. 17, 2005.
Bellosillo, B., et al., "Complement-Mediated Cell Death Induced by Rituximab in B-Cell Lymphoproliferative Disorders is Mediated in vitro by a Caspase-Independent Mechanism Involving the Generation of Reactive Oxygen Species," Blood 98(9):2771-2777 (2001).
Bertilaccio, M.T.S., et al., "A Novel Rag2-Gamma2-Xenograft Model of Human CLL," Blood 115(8):1605-1609 (2010).
Bonnet, D. and Dick, J.E., "Human Acute Myeloid Leukemia is Organized as a Hierarchy that Originates from a Primitive Hematopoietic Cell," Nat. Med. 3(7):730-737 (1997).
Borche L, et al. CD43 monoclonal antibodies recognize the large sialoglycoprotein of human leukocytes. Eur J Immunol. 17(10):1523-6. Oct. 1987.
Brodsky FM. A matrix approach to human class II histocompatibility antigens: reactions of four monoclonal antibodies with the products of nine haplotypes. Immunogenetics. 19(3):179-94. 1984.
Bruhl, H., et al., "Depletion of CCR5-Expressing Cells with Bispecific Antibodies and Chemokine Toxins: A New Strategy in the Treatment of Chronic Inflammatory Diseases and HIV," The Journal of Immunology, vol. 166, pp. 2420-2426 (2001).
Carter, P.J., "Introduction to Current and Future Protein Therapeutics: A Protein Engineering Perspective," Exp. Cell Res. 317:1261-1269 (2011).
Carter, P.J., "Potent Antibody Therapeutics by Design," Nat. Rev. Immunol 6:343-357 (2006).
Chinese Office Action in corresponding CN application No. 201280024084.1, dated Jul. 21, 2015.
Choi et al., "Bispecific antibodies engage T cells for antitumor immunotherapy," Expert Opin. Biol. Ther. 11(7), pp. 842-853, 2011.
Clark, E.A., et al., "Role ofBp35 Cell Surface Polypeptide in Human B-Cell Activation," Proc. Natl. Acad. Sci. 82: 1766-1770 (1985).
Clarke, et al., "Gemtuzumab Ozogamicin: Is There Room for Salvage?" Blood 116(14):2618-2619 (2010).
Cochran, Domain-level antibody epitope mapping through yeast surface display of epidermal growth factor receptor fragments, J of Immunological Methods 287:147-158 (2004).
Davol et al., "Anti-CD3 x Anti-HER2 Bispecific Antibody Effectively Redirects Armed T Cells to Inhibit Tumor Development and Growth in Hormone-Refractory Prostate Cancer-Bearing Severe Combined Immunodeficient Beige Mice," Clinical Prostate Cancer, vol. 3, No. 2, pp. 112-121, 2004.
De Groot, A.S., et al., "Activation of Natural Regulatory T Cells by IgG Fc-derived Peptide 'Tregitopes'," Blood 112 (8):3303-3311 (2008).
Deckert M, et al. CD59 molecule: a second ligand for CD2 in T cell adhesion. Eur J Immunol. 22(11):2943-7. Nov. 1992.

(56) References Cited

OTHER PUBLICATIONS

Demichelis et al., "Comparative Immumohistochemical Study of MUC1 and Carbohydrate Antigens in Breast Benign Disease and Normal Mammary Gland," Appl. Immunohistochem. Mol. Morphol. vol. 18, No. 1, Jan. 2010, pp. 41-50.
Dermer, Another anniversary for the war on cancer, Bio/technology 12:320 (1994).
Donda, A., et al., "In vivo Targeting of an Anti-Tumor Antibody Coupled to Antigenic MHC Class I Complexes Induces Specific Growth Inhibition and Regression of Established Syngeneic Tumor Grafts," Cancer Immunity 3:11 (2003).
Duncan RJS et al., "A new reagent which may be used to introduce sulfhydryl groups into proteins, and its use in the preparation of conjugates for immunoassay," Analytical Biochemistry, 132(1):68-73 (Jul. 1, 1983).
Eberl, G., et al., "An Anti-CD19 Antibody Coupled to a Tetanus Toxin Peptide Induces Efficient Fas Ligand (FasL)-Mediated Cytotoxicity of a Transformed Human B Cell Line by Specific CD4+ T Cells," Clinical and Experimental Immunology 114:173-178 (1998).
Engleman EG, et al. Studies of a human T lymphocyte antigen recognized by a monoclonal antibody. Proc Natl Acad Sci U S A. 78(3):1791-5. Mar. 1981.
Eno-Amooquaye, E.A., et al., "Altered Biodistribution of an Antibody-Enzyme Conjugate Modified with Polyethylene Glycol," Br. J. Cancer 73:1323-1327 (1996).
Epstein AL, et al. Two new monoclonal antibodies (LN-1, LN-2) reactive in B5 formalin-fixed, paraffin-embedded tissues with follicular center and mantle zone human B lymphocytes and derived tumors. J Immunol. 133(2):1028-1036. Aug. 1984.
European Office Action in corresponding EP Application No. 12718715.1, dated Jul. 23, 2015.
Fattah, O.M., et al., "Peptabody-EGF: A Novel Apoptosis Inducer Targeting ErbB 1 Receptor Overexpressing Cancer Cells," Int. J. Cancer 119:2455-2463 (2006).
File History of U.S. Appl. No. 14/381,405, filed Aug. 27, 2014.
First Office Action and Search Report from the State Intellectual Property Office of the People's Republic of China for Application No. 201280024084.1, dated Nov. 15, 2014 (18 pages).
Fluhr H, et al. Interferon-gamma and tumor necrosis factor-alpha sensitize primarily resistant human endometrial stromal cells to Fas-mediated apoptosis. J Cell Sci. 120(Pt 23):4126-33. Dec. 1, 2007; Epub Nov. 14, 2007.
Gendler et al., "Cloning of partial cDNA encoding differentiation and tumor-associated mucin glycoproteins expressed by human mammary epithelium," Proc. Natl. Acad. Sci. USA, vol. 84, pp. 6060-6064, Sep. 1987.
Germain, C., et al., "MHC Class I-Related Chain a Conjugated to Antitumor Antibodies can Sensitize Tumor Cells to Specific Lysis by Natural Killer Cells," Clin. Cancer Res. 11(20):7516-7522 (2005).
Ghanekar et al., Clin Diagn Lab Immunol 8(3):628-31 (2001).
Ghanekar et al., Gamma Interferon Expression in CD8+ T Cells is a Marker for Circulating Cytotoxic T Lymphocytes that Recognize an HLA A2-Restricted Epitope of Human Cytomegalovirus Phosphoprotein p65, Clin Diagn Lab Immunol 8(3):628-31 (2001).
Giovannoni, L., et al., "Isolation of Anti-angiogenesis Antibodies from a Large Combinatorial Repertoire by Colony Filter Screening," Nucleic Acids Research 29(5):E27 (2001).
Golay, Mechanisms of action of therapeutic monoclonal antibodies: promises and pitfalls of in vitro and in vivo assays, Archives of Biochemistry and Biophysics 526:146-153 (2012).
Grimbert P. Thrombospondin/CD47 interaction: a pathway to generate regulatory T cells from human CD4+ CD25− T cells in response to inflammation. J Immunol. 177(6):3534-41. Sep. 15, 2006.
Gura, Systems for identifying new drugs are often faulty, Science 278:1041-1042 (1997).
Hellstrom, I., et al., "Monoclonal Mouse Antibodies Raised Against Human Lung Carcinoma," Cancer Research 46:3917-3923 (1986).

Hislop, A.D., et al., "Cellular Responses to Viral Infection in Humans: Lessons from Epstein-Barr Virus," Annu. Rev. Immunol. 25:587-617 (2007).
Hochman J, et al., Biochemistry 15(12) :2706-2710 (1976).
Horie R, Watanabe T. CD30: expression and function in health and disease. Semin Immunol. 10(6):457-70. Dec. 1998.
Horne C, et al., Immunol. 129:660-664 (1982).
Howland, S.W., et al., "Inducing Efficient Cross-Priming Using Antigen-Coated Yeast Particles," J. Immunother. 31(7):607-619 (2008).
Hughes, B., "Antibody-Drug Conjugates for Cancer: Poised to Deliver?," Nature Reviews Drug Discovery 9:665-667 (2010).
International Preliminary Report on Patentability for International Application PCT/GB2012/050577; dated Sep. 17, 2013.
International Preliminary Report on Patentability for PCT/GB2013/050499 dated Sep. 2, 2014.
International Search Report and Written Opinion of the International Searching Authority for International Application No. PCT/GB2012/050577, "Re-Directed Immunotherapy," dated Jun. 29, 2012.
International Search Report for PCT/GB2013/050499 dated Jul. 24, 2013.
International Search Report for PCT/GB2013/052427 dated May 2, 2014.
Irvine, D.J., et al., "Direct Observation of Ligand Recognition by T Cells," Nature 419:845-849. (2002).
Jager, et al., "Domain interactions in antibody Fv and scFv fragments: effects on unfolding kinetics and equilibria," FEBS Letters 462, pp. 307-312, 1999.
Jaton, Jean-Claude, "Amino Acid Sequence of the N-Terminal 139 Residues of Light Chain Derived from a Homogeneous Rabbit Antibody," Biochem. J. (1974) 141, pp. 1-13.
Jeffrey, S.C., et al., "Dipeptide-Based Highly Potent Doxorubicin Antibody Conjugates," Bioorganic & Medicinal Chemistry Letters 16:358-362 (2006).
Jilaveanu LB, et al. CD70 expression patterns in renal cell carcinoma. Hum Pathol. 43(9):1394-9. Sep. 2012; Epub Mar. 7, 2012.
Jubala, CD20 Expression in Normal Canine B Cells and in Canine non-Hodgkin Lymphoma, Vet Pathol 42:468-476 (2005).
Jutila MA, et al. L-selectin serves as an E-selectin ligand on cultured human T lymphoblasts. J Immunol. 169(4):1768-73. Aug. 15, 2002.
Kawamura, K.S., et al., "In Vivo Generation of Cytotoxic T Cells from Epitopes Displayed on Peptide-Based Delivery Vehicles," Journal of Immunology 168:5709-5715 (2002).
Khendri et al., "Cancer immunotherapy via nucleic acid aptamers," International Immunopharmacology 29 (2015), pp. 926-936.
Kjer-Nielsen et al., "Crystal structure of the human T cell receptor CD3{epsilon}{gamma} heterodimer complexed to the therapeutic mAb OKT3," PNAS 101, pp. 7675-7680, May 10, 2014.
Klechevsky E, et al. Cross-priming CD8+ T cells by targeting antigens to human dendritic cells through DCIR. Blood. 116(10):1685-97. Sep. 9, 2010; Epub Jun. 7, 2010.
Kohler, et al., "Continuous Cultures of Fused Cells Secreting Antibody of Predefined Specificity," Nature 256:495-497 (1975).
Kozak, R.W., et al., "IL-2-PE40 Prevents the Development of Tumors in Mice Injected with IL-2 Receptor Expressing EL4 Transfectant Tumor Cells," Journal of Immunology 145 (8):2766-2771 (1990).
Kreitman RJ, et al. Phase I trial of anti-CD22 recombinant immunotoxin moxetumomab pasudotox (CAT-8015 or HA22) in patients with hairy cell leukemia. J Clin Oncol. 230(15):1822-8. May 20, 2012; Epub Feb. 21, 2012.
Kufer, P., et al., "Construction and Biological Activity of a Recombinant Bispecific Single-Chain Antibody Designed for Therapy of Minimal Residual Colorectal Cancer," Cancer Immunology Immunotherapy, vol. 45, pp. 193-197 (1997).
Lagadec P, et al. Involvement of a CD47-dependent pathway in platelet adhesion on inflamed vascular endothelium under flow. Blood. 101(12):4836-43. Jun. 15, 2003; Epub Feb. 27, 2003.
Lamb CA, et al. Invariant chain targets HLA class II molecules to acidic endosomes containing internalized influenza virus. Proc Natl Acad Sci U S A. 88(14):5998-6002. Jul. 15, 1991.

(56) References Cited

OTHER PUBLICATIONS

Larche, M., et al., "Functional Evidence for a Monoclonal Antibody that Binds to the Human IL-4 Receptor," Immunology 65:617-622 (1988).
Lash, A., "Making the Case for Antibody-Drug Conjugates," In Vivo: The Business and Medicine Report:32-38 (2010).
Lehmann JC, et al. Overlapping and selective roles of endothelial intercellular adhesion molecule-1 (ICAM-1) and ICAM-2 in lymphocyte trafficking. J Immunol. 171(5):2588-93. Sep. 1, 2003.
Lesley J, Trowbridge IS. Genetic characterization of a polymorphic murine cell-surface glycoprotein. Immunogenetics. 15(3):313-20. Mar. 1982.
Li et al., "Inhibition of Cell Proliferation by an Anti-EGFR Aptamer," PLoS ONE, vol. 6, Issue 6, Jun. 2011, pp. 1-10.
Li et al., "Inhibition of Cell Proliferation by an Anti-EGFR Aptamer," PLoS ONE, vol. 6, Issue 6, Jun. 2011, Supplemental Table S2 (1 page).
Li S, et al., "Analysis of FOXP3+ regulatory T cells that display apparent viral antigen specificity during chronic hepatitis C virus infection," PLoS Pathog. Dec. 2009;5(12):e1000707. Epub Dec. 24, 2009.
Loffler et al. "A recombinant bispecific single-chain antibody, CD19 x CD3, induces rapid and high lymphoma-directed cytotoxicity by unstimulated T lymphocytes." 95(6):2098-103 (Mar. 15, 2000).
Loisel, S. et al., "Establishment of a Novel Human B-CLL-like Xenograft Model in Nude Mouse," Leukemia Research 29:1347-1352 (2005).
Lorberboum-Galski, H., et al., "Cytotoxic Activity of an Interleukin 2-Pseudomonas Exotoxin Chimeric Protein Produced in *Escherichia coli*," Proc. Natl. Acad. Sci 85: 1922-1926 (1988).
Lutterbuese R. et al., "T cell-engaging BiTE antibodies specific for EGFR potently eliminate KRAS- and BRAF-mutated colorectal cancer cell", Proc. Natl. Acad. Sci. 107(28):12605-12610. (Jul. 13, 2010).
Lutterbuese, R., et al., "Potent Control of Tumor Growth by CENCD3-bispecific Single-Chain Antibody Constructs that are not Competitively Inhibited by Soluble CEA," J. Immunother. 32(4):341-352 (2009).
Mack et al., PNAS 92:7021-7025 (1995).
Mack, M., et al., "A Small Bispecific Antibody Construct Expressed as a Functional Single-Chain Molecule With High Tumor Cell Cytotoxicity," Proceedings of the National Academy of Sciences, vol. 93, pp. 7021-7025 (Jul. 1995).
Mack, M., et al., "Biologic Properties of a Bispecific Single-Chain Anitbody Directed Against 17-1A (EpCAM) and CD3; Tumor Cell-Dependent T Cell Stimulation and Cytotoxic Activity," The Journal of Immunology, vol. 158, pp. 3965-3971 (1997).
Mahato, R., et al., "Prodrugs for Improving Tumor Targetability and Efficiency," Adv. Drug. Deily. Rev. 63(8):659-670 (2011).
Maiti A et al. TNF-alpha induction of CD44-mediated leukocyte adhesion by sulfation. Science. 282(5390):941-3. Oct. 30, 1998.
Masuda K, et al., FEBS Journal 273:20184-2194 (2006).
Matsumura, Y. and Maeda, H., "A New Concept for Macromolecular Therapeutics in Cancer Chemotherapy: Mechanism of Tumoritropic Accumulation of Proteins and the Antitumor Agent Smancs," Cancer Res. 46:6387-6392 (1986).
Mayes, S., et al., "New Antibody Drug Treatments for Lymphoma," Expert Opin. Biol. Ther. 11 ( 5):623-640 (2011 ).
Mazor R, et al. Identification and elimination of an immunodominant T-cell epitope in recombinant immunotoxins based on Pseudomonas exotoxin A. Proc Natl Acad Sci U S A. 109(51):E3597-603. Dec. 18, 2012. Epub Dec. 3, 2012.
Melton, R.G., et al., "Covalent Linkage of Carboxypeptidase G2 to Soluble Dextrams-1," Biochemical Pharmacology 36(1):105-112 (1987).
Meziere, C., et al., "In Vivo T Helper Cell Response to Retro-Inverso Peptidomimetics," J. Immunol. 159:3230-323 7 (1997).
Molhoj et al. "CD19-/CD3-bispecific antibody of the BiTE class is far superior to tandem diabody with respect to redirected tumor cell lysis", Mol Immunol. 44(8):1935-1943. (Dec. 1, 2006).
Moller et al., "NMR-based determination of the binding epitope and conformational analysis of MUC-1 glycopeptides and peptides bound to the breast cancer-selective monoclonal antibody SM3," Eur. J. Biochem. 269, pp. 1444-1455, 2002.
Moore, P.A., et al., "Application of Dual Affinity Retargeting Molecules to Achieve Optimal Redirected T-Cell Killing of B-Cell Lymphoma," Blood 117(17):4542-4551 (2011).
Mous et al., "Redirection of CMV-specific CTL towards B-CLL via CD20-targeted HLA/CMV complexes," Leukemia 20, pp. 1096-1102 (2006).
Murphy, G., "The ADAMs: Signalling Scissors in the Tumour Microenvironment," Nature Reviews Cancer 8:929-941 (2008).
Nakanishi T et al., Protein Science 17:261-270 (2008).
Non-Final Office Action in corresponding U.S. Appl. No. 14/005,452, dated Jul. 31, 2015.
Non-Final Office Action in corresponding U.S. Appl. No. 14/660,137, dated Oct. 22, 2015.
Ogg, G.S., et al., "Sensitization of Tumour Cells to Lysis by Virus-Specific CTL using Antibody-Targeted MHC Class I/Peptide Complexes," British Journal of Cancer 82( 5): 105 8-1062 (2000).
Onda M, et al. An immunotoxin with greatly reduced immunogenicity by identification and removal of B cell epitopes. Proc Natl Acad Sci U S A. 2105(32):11311-6. Aug. 12, 2008; Epub Aug. 4, 2008.
Osborn L, et al. Amino acid residues required for binding of lymphocyte function-associated antigen 3 (CD58) to its counter-receptor CD2. J Exp Med. 181(1):429-34. Jan. 1995.
O'Sullivan MK, et al., "Comparison of two methods of preparing enzyme-antibody conjugates: application of these conjugates for enzyme immunoassay," Anal Biochem. Nov. 15, 1979;100(1):100-8.
O'Sullivan, M.J., et al., "Comparison of Two Methods of Preparing Enzyme-Antibody Conjugates: Application of these conjugates for Enzyme Immunoassay," Analytical Biochemistry 100: 100-108(1979).
Park, B.-W., et al., "Rationally Designed Anti-HER2/neu Peptide Mimetic Disables P185HER2/neu Tyrosine Kinases in vitro and in vivo," Nature Biotechnology 18: 194-198 (2000).
PDB locus 1SY6_A, 204 amino acids, Oct. 10, 2012, pp. 1-3.
Plant, A, et al., "Phospholipid/Alkanethiol Bilayers for Cell-Surface Receptor Studies by Surface Plasmon Resonance," Analytical Biochemistry, vol. 226, pp. 342-348 (1995).
Polski JM and Janney CG. Ber-H2 (CD30) immunohistochemical staining in malignant melanoma. Mod Pathol. 12(9):903-6. Sep. 1999.
Ponde, D.E., et al., "Development of Anti-EGF Receptor Peptidomimetics (AERP) as Tumor Imaging Agent," Bioorganic & Medicinal Chemistry Letters 21 :2550-2553 (2011 ).
Poon, KA, "Safety Assessment of Antibody Drug Conjugates," Presentation at Northern California Society of Toxicology. May 6, 2010.
Porcelli, S., et al., "Recognition of Cluster of Differentiation 1 Antigens by Human CD4-CD8-Cytolytic T Lymphocytes," Nature 341:447-450 (1989).
Rader, C., "DARTs Take Aim at BiTEs," Blood 117:4403-4404 (2011).
Rajasagi M. CD44 promotes progenitor homing into the thymus and T cell maturation. J Leukoc Biol. 85(2):251-61. Feb. 2009; Epub Oct. 27, 2008.
Rawlings, N.D., et al., "MEROPS: the Peptidase Database," Nucleic Acids Research 36:D320-D325 (2008).
Response to Office Action from European Patent Office dated Nov. 8, 2013, filed Apr. 14, 2014, for European Patent Application No. 12718715.1 (21 pages).
Rich, D.H., "Inhibitors of cysteine proteases." In Research monographs in cell and tissue physiology vol. 12, Proteinase inhibitors. Barrett AJ, Salvesen G, eds. (Amsterdam: Elsevier.) pp. 153-178 (1986).
Riechmann L J Mol Biol. 259:957-969 (1996).
Romagnoli, P., et al., "Selective Interaction of Ni with an MHC-Bound Peptide," The EMBO Journal 10(6):1303-1306 (1991).
Romero, P., et al., "Photoaffinity Labeling of the T Cell Receptor on Living Cytotoxic T Lymphocytes," The Journal of Immunology 150(9):3825-3831 (1993).

(56) References Cited

OTHER PUBLICATIONS

Rothlisberger D, et al., J. Mol. Biol. 347, 773-789 (2005).
Salmeron et al., "A Conformational Epitope Expressed Upon Association of CD3-e with Either CD3- or CD3-y is the Main Target for Recognition by Anti-CD3 Monoclonal Antibodies," J. Immun., vol. 147, No. 9, pp. 3047-3052, Nov. 1, 1991.
Sathish, Challenges and approaches for the development of safer immunomodulatory biologics, Nature Reviews Drug Discovery 12:306-324 (2013).
Savage, P., et al., "Induction of Viral and Tumour Specific CTL Responses Using Antibody Targeted HLA Class I Peptide Complexes," British Journal of Cancer 86:1336-1342 (2002).
Schaffitzel, C., et al., "Ribosome Display: an in vitro Method for Selection and Evolution of Antibodies from Libraries," Journal of Immunological Methods 231 :119-135 (1999).
Schmiegel, W., et al., "Cytokine-Mediated Enhancement of Epidermal Growth Factor Receptor Expression Provides an Immunological Approach to the Therapy of Pancreatic Cancer," Proc. Natl. Acad. Sci. 94:12622-12626 (1997).
Search report from Intellectual Property Office for GB1216649 dated Jan. 17, 2013.
Searle, F., et al., "A Human Choriocarcinoma Xenograft in Nude Mice; a Model for the Study of Antibody Localization," British Journal Cancer 44: 13 7-144 (1981).
Senter, P.D., et al., "Anti-Tumor Effects of Antibody-Alkaline Phosphatase Conjugates in Combination with Etoposide Phosphate," Proc. Natl. Acad. Sci. 85:4842-4846 (1988).
Shangguan et al., "Aptamers evolved from live cells as effective molecular probes for cancer study," PNAS, vol. 103, No. 32, Aug. 8, 2006, pp. 11838-11843.
Shen, L., et al., "Important Role of Cathepin S in Generating Peptides for TAP-Independent MHC Class I Crosspresentation In Vivo," Immunity 21:155-165 (2004).
Sherman, D.B. and Spatola, A.F., "Compatibility of Thioamides with Reverse Turn Features: Synthesis and Conformational Analysis of Two Model Cyclic Pseudopeptides Containing Thioamides as Backbone Modifications," J. Am. Chem. Soc. 112:433-441 (1990).
Small, E.J., et al., "Placebo-Controlled Phase III Trial of Immunologic Therapy with Sipuleucel-T (APC8015) in Patients with Metastatic, Asymptomatic Hormone Refractory Prostate Cancer," Journal of Clinical Oncology 24(19):3089-3094 (2006).
Smith, D.C., et al., "Exogenous Peptides Delivered by Ricin Require Processing by Signal Peptidase for Transporter Associated with Antigen Processing-Independent MHC Class I restricted Presentation," J. Immunol. 169:99-107 (2002).
Staerz, U., et al., "Hybrid Antibodies Can Target Sites for Attack by T Cells," Nature, vol. 314, pp. 628-631 (Apr. 1985).
Staerz, U.D. and Bevan, M.J., "Hybrid Hybridoma Producing a Bispecific Monoclonal Antibody that can Focus Effector T-Cell Activity," Proc. Natl. Acad. Sci 83: 1453-1457 (1986).
Stein R, et al. Epitope specificity of the anti-(B cell lymphoma) monoclonal antibody, LL2. Cancer Immunol Immunother. 37(5):293-8. Oct. 1993.
Stirnemann, K., et al., "Sustained Activation and Tumor Targeting of NKT Cells Using a CDIdanti-HER2-scFv Fusion Protein Induce Antitumor Effects in Mice," The Journal of Clinical Investigation 118(3 ):994-1005 (2008).
Sumida T, et al., "Regulatory T cell epitope recognized by T cells from labial salivary glands of patients with Sjögren's syndrome," Arthritis Rheum. Dec. 1997;40(12):2271-3.
Sykulev, Y., et al., "Evidence that a Single Peptide-MHC Complex on a Target Cell can Elicit a Cytolytic T Cell Response," Immunity 4:565-571 (1996).
Sylwester, A.W., et al., "Broadly Targeted Human Cytomegalovirus-Specific CD4+ and CD8+ T Cells Dominate the Memory Compartments of Exposed Subjects," The Journal of Experimental Medicine 202(5):673-685 (2005).

Tamiolakis D et al. Distribution of somatostatin in pancreatic ductal adenocarcinoma remodels the normal pattern of the protein during foetal pancreatic development: an immunohistochemical analysis. Clin Exp Med. 5(3):106-11, 2005.
Thie et al., "Rise and Fall of an Anti-MUC1 Specific Antibody," PLoS ONE, vol. 5, Issue 1, pp. 1-19, Jan. 2011.
Thompson et al., "Light-activated antibodies in the fight against primary and metastic cancer," Drug Discovery Today, vol. 15, Nos. 11/12, pp. 468-473, Jun. 2010.
Thompson et al., "Preclinical evaluation of light-activatable, bispecific anti-human CD3 antibody conjugates as anti-ovarian cancer therapeutics," mAbs 1:4, Landes Bioscience, pp. 348-356, Jul./Aug. 2009.
Thorsett, E.D., et al., "Dipeptide Mimics. Conformationally Restricted Inhibitors of Angiotensin-Converting Enzyme," Biochemical and Biophysical Research Communications 111(1):166-171 (1983).
Tosolini, M., et al., "Clinical Impact of Different Classes of Infiltrating T Cytotoxic and Helper Cells (Thl, Th2, Treg, Thl 7) in Patients with Colorectal Cancer," Cancer Res. 71 (4):1263-1271 (2011).
Trowbridge IS, et al. Biochemical characterization and cellular distribution of a polymorphic, murine cell-surface glycoprotein expressed on lymphoid tissues. Immunogenetics. 15(3):299-312, Mar. 1982.
Veber, D.F ., et al., "Conformationally Restricted Bicyclic Analogs of Somatostatin," Proc. Natl. Acad. Sci. 75(6):2636-2640 (1978).
Vita, R., et al., "The Immune Epitope Database 2.0," Nucleic Acids Research 38:D854-D862 (2010).
Waldman, T.A., et al., "Immune Receptors: Targets for Therapy of Leukemia/Lymphoma, Autoimmune Diseases and for the Prevention of Allograft Rejection," Annu. Rev. Immunol. 10:675-704 (1992).
Wang, Q.-C., et al., "Induction of Hepatitis C Virus-Specific Cytotoxic T and B Cell Responses by Dendritic Cells Expressing a Modified Antigen Targeting Receptor," World Journal of Gastroenterology 11(4):557-560 (2005).
Webb S, et al., "Pharma interest surges in antibody drug conjugates," Nat Biotechnol. Apr. 2011;29(4):297-8.
Winter, G., et al., "Making Antibodies by Phage Display Technology," Annu. Rev. Immunol. 12:433-455 (1994).
Witte, Monoclonal antibodies targeting the VEGF receptor-2 (Flk1/KDR) as an anti-angiogenic therapeutic strategy, Cancer and Metastasis Reviews 17:155-151 (1998).
Written Opinion of the International Searching Authority for PCT/GB2013/050499 dated Jul. 24, 2013.
Wucherpfennig, et al., "Structural Biology of the T-cell Receptor: Insights into Receptor Assembly, Ligand Recognition, and Initiation of Signaling," Cold Spring Harb. Perspect. Biol., 2:a005140, pp. 1-16, 2010.
Yu, Interaction between Bevacizumab and Murine VEGF-A: A Reassessment, Investigative Ophthalmology & Visual Science 49(2):522 (2008).
Yu, Tsan-Hua et al., "Viral hepatitis is associated with intrahepatic cholangiocarcinoma with cholangiolar differentiation and N-cadherin expression," Modern Pathology (2011) 24, pp. 810-819.
Zhou, X. et al., "The Role of Complement in the Mechanism of Action of Rituximab for B-Cell Lymphoma: Implications for Therapy," The Oncologist 13:954-966 (2008).
Zhu et al., "Aptamer-Drug Conjugates," Bioconjugate Chem. 2015, 26, 2186-2197.
Lyu et al., "Generating Cell Targeting Aptamers for Nanotheranostics Using Cell-SELEX," Theranostics 2016; 6(9), pp. 1440-1452.
Wu et al., "Aptamers: Active Targeting Ligands for Cancer Diagnosis and Therapy," Theranostics 2015; 5(4); pp. 322-344.
Xiang et al., "Nucleic Acid Aptamer-Guided Cancer Therapeutics and Diagnostics: the Next Generation of Cancer Medicine," Theranostics 2015; 5(1), pp 23-42.
Zhu et al., "Progress in Aptamer-Meditated Drug Delivery Vehicles for Cancer Targeting and Its Implications in Addressing Chemotherapeutic Challenges," Theranostics 2014; 4(9), pp. 931-944.

(56) References Cited

OTHER PUBLICATIONS

International Search Report and Written Opinion issued in corresponding PCT Application No. PCT/US2016/062748, dated Jan. 27, 2017, 16 pages.
Figure 1 from Encyclopedia Britannica "Antibody" entry, 2017.
Lee et al., "Cell polarity and cancer—cell and tissue polarity as a non-canonical tumor suppressor," Journal of Cell Science 121(8):1141-1150 (2008).
Trzpis et al., "Epithelial Cell Adhesion Molecule," The American Journal of Pathology 171(2):386-395 (2007).

* cited by examiner

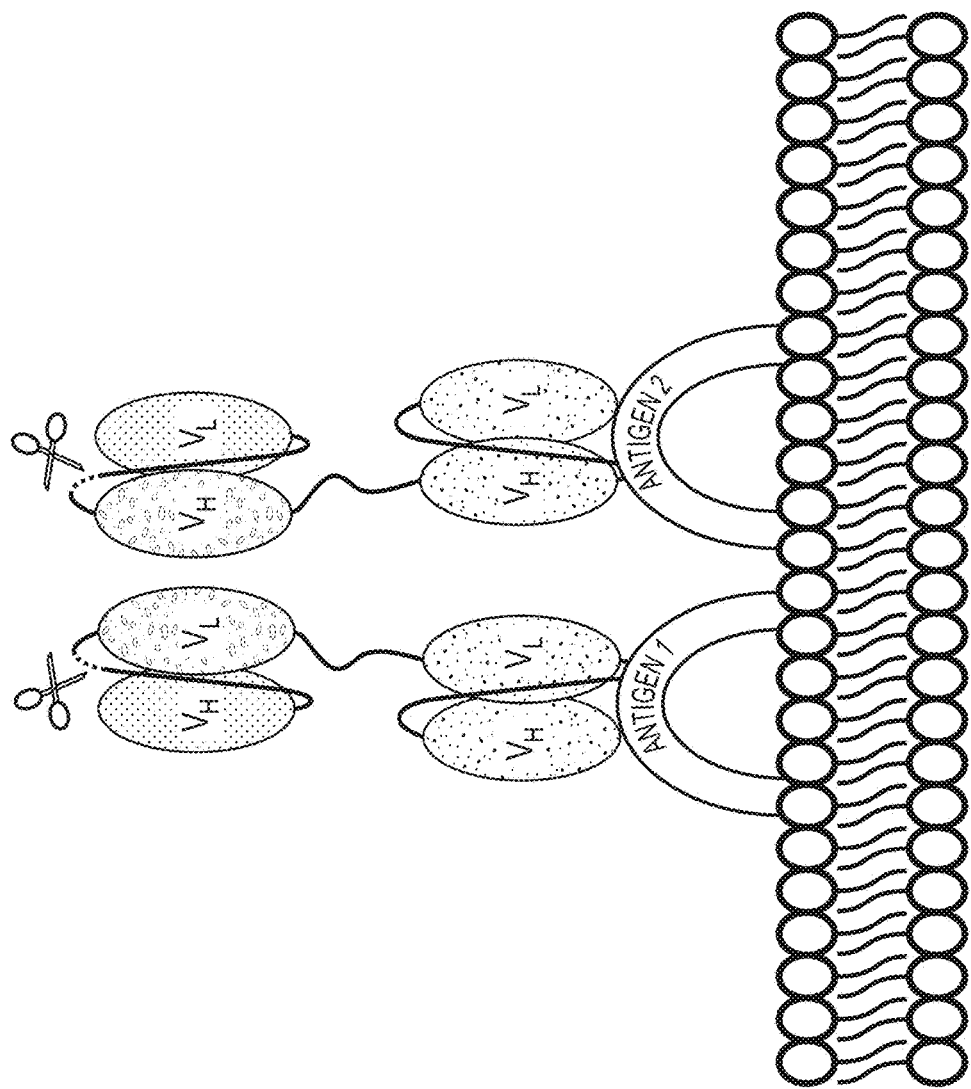

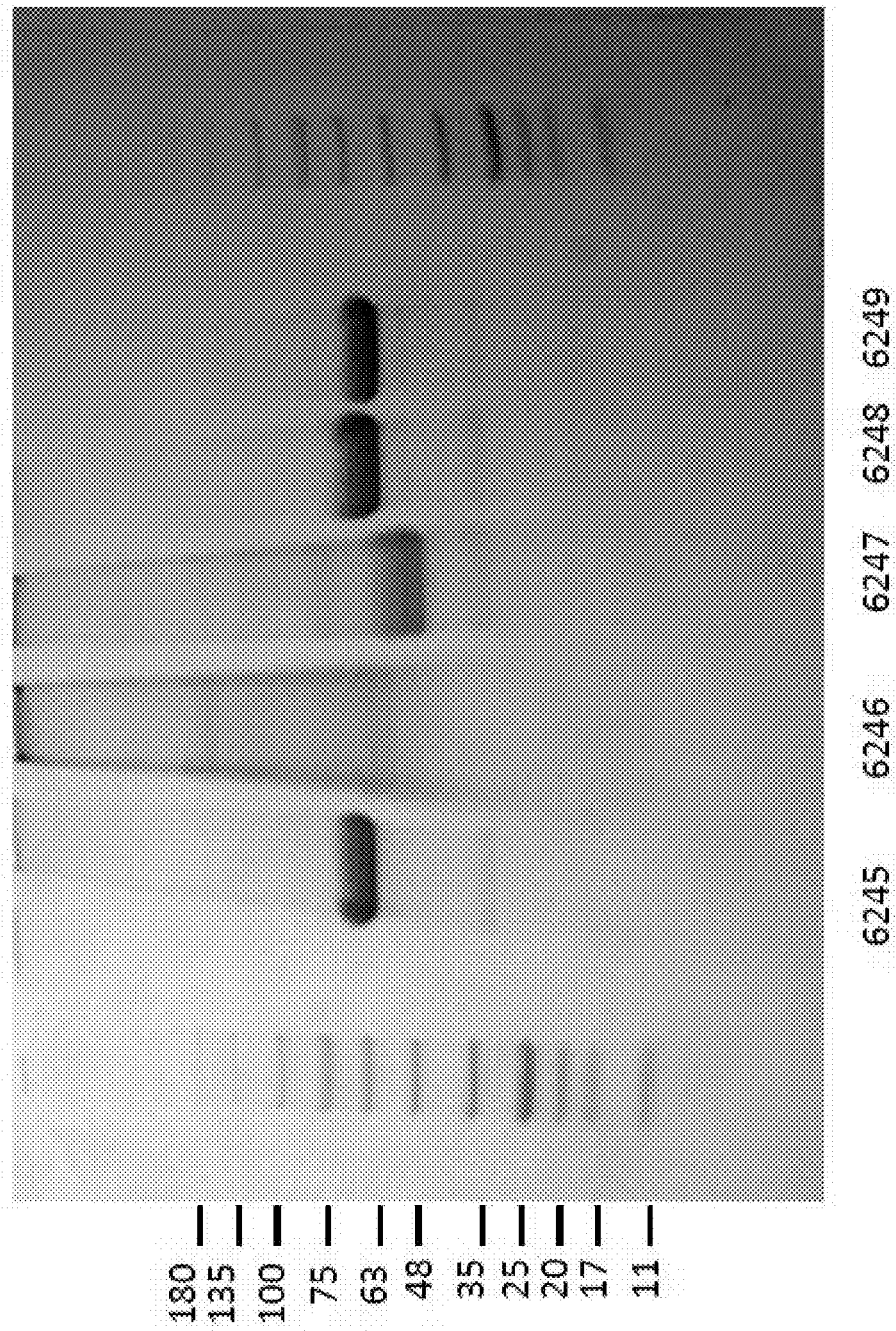

6248 EpCAM scFv (V_L [LINKER] V_H) [LINKER]-scFv(Anti-CD3ε V_H [CLEAVABLE LINKER] inert V_L) hexahistidine tag (MMP2 cleavage site bold underlined)

ELVMTQSPSSLTVTAGEKVTMSCKSSQSLLNSGNQKNYLTWYQQKPGQPPKLLIYWASTRESGVPDR
FTGSGSGTDFTLTISSVQAEDLAVYYCQNDYSYPLTFGAGTKLEIK[GGGGSGGGGSGGGGS]EVQLLE
QSGAELVRPGTSVKISCKASGYAFTNYWLGWVQRPGHGLEWIGDIFPGSGNIHYNEKFKGKATLTA
DKSSSTAYMQLSSLTFEDSAVYFCARLRNWDEPMDYWGQGTTVTVSS[GGGGS]DVQLVQSGAEVKKPG
ASVKVSCKASGYTFTRYTMHWVRQAPGQGLEWIGYINPSRGYTNYADSVKGRFTITTDKSTSTAYME
LSSLRSEDTATYYCARYYDDHYCLDYWGQGTTVTVSS[GEGTSTGSGAIPVSLRGSGGSGGAD]DIVLT
QSPATLSLSPGERATLSCRASQSVSSSYLAWYQQKPGQAPRLLIYGASSRATGVPARFSGSGSGTDF
TLTISSLEPEDFATYYCLQIYNMPITFGQGTKVEIKHHHHHH    (SEQ ID NO: 168)

6249 EpCAM scFv (V_L [LINKER] V_H) [LINKER]-scFv(Anti-CD3ε V_L [CLEAVABLE LINKER] inert V_H) hexahistidine tag (MMP2 cleavage site underlined)

ELVMTQSPSSLTVTAGEKVTMSCKSSQSLLNSGNQKNYLTWYQQKPGQPPKLLIYWASTRESGVPDR
FTGSGSGTDFTLTISSVQAEDLAVYYCQNDYSYPLTFGAGTKLEIK[GGGGSGGGGSGGGGS]EVQLLE
QSGAELVRPGTSVKISCKASGYAFTNYWLGWVQRPGHGLEWIGDIFPGSGNIHYNEKFKGKATLTA
DKSSSTAYMQLSSLTFEDSAVYFCARLRNWDEPMDYWGQGTTVTVSS[GGGGS]DIVLTQSPATLSLSP
GERATLSCRASQSVSYMNWYQQKPGKAPKRWIYDTSKVASGVPARFSGSGSGTDYSLTINSLEAEDA
ATYYCQQWSSNPLTFGGGTKVEIK[GEGTSTGSGAIPVSLRGSGGSGGAD]DVQLVQSGAEVKKPGASV
KVSCKASGYTFTGYYMHWVRQAPGQGLEWMGWINPNSGGTNYAQKFQGRVTITRDTSASTAYMELSS
LRSEDTAVYYCARDFLSGYLDYWGQGTLVTVSSHHHHHH    (SEQ ID NO: 169)

FUNCTIONAL ANTIBODY FRAGMENT COMPLEMENTATION FOR A TWO-COMPONENTS SYSTEM FOR REDIRECTED KILLING OF UNWANTED CELLS

CROSS-REFERENCE TO RELATED APPLICATIONS

The present application claims the benefit of priority of U.S. Provisional Application No. 62/257,552, filed Nov. 19, 2015, and U.S. Provisional Application No. 62/270,907, filed Dec. 22, 2015.

SEQUENCE LISTING

The present application is filed with a Sequence Listing in electronic format. The Sequence Listing is provided as a file entitled "2017-04-19_01131-0007-00US_SL_ST25.txt" created on Apr. 19, 2017, which is 84,197 bytes in size.

FIELD

This application relates to targeted T-cell engaging agents for treating a condition characterized by the presence of unwanted cells. In particular, it relates to agents that can be used to treat a condition characterized by the presence of unwanted cells, such as cancer or other disease-causing cells.

BACKGROUND

Cancer and other diseases caused by the presence of unwanted cells create significant loss of life, suffering, and economic impact. Immunotherapeutic strategies for targeting cancer have been an active area of translational clinical research.

A variety of other approaches have been explored for immunotherapy, but many of these prior approaches lack sufficient specificity to particular unwanted cells. For example, demibodies have been designed each having an scFv portion binding to different antigens on a target cell, an Fc domain allowing pairing to a complementary demibody, and a binding partner capable of forming an association to another binding partner on a complementary demibody. WO 2007/062466. These demibodies, however, are not necessarily specific to cancer cells and could bind and have activity on other cells expressing the same antigens. See also WO 2013/104804, which provides a first polypeptide with a targeting moiety binding to a first antigen and a first fragment of a functional domain, along with a second polypeptide with a targeting moiety binding to a second antigen and a second fragment of a functional domain that is complementary to the first fragment of the functional domain. Likewise, this approach is not necessarily specific to cancer cells and could bind and have activity on other cells expressing the same antigens.

While some positive test data has been shown with prior approaches, clinically-effective therapeutic strategies must be able to elicit a strong immune response in an individual suffering from a disease such as cancer. Additionally, effective therapies should be very specific and not cause unwanted side effects to other cell types in the body. Therefore, additional developments in this field of re-directed immunotherapy are required.

SUMMARY

In accordance with the description, the inventors describe a targeted T-cell engaging agent for treating a condition characterized by the presence of unwanted cells. This agent includes (a) a targeting moiety that is capable of targeting the unwanted cells; (b) a first T-cell engaging domain capable of activity when binding a second T-cell engaging domain, wherein the second T-cell engaging domain is not part of the agent; (c) at least one inert binding partner capable of binding the first T-cell engaging domain such that the first T-cell engaging domain does not bind to the second T-cell engaging domain unless the inert binding partner is removed; and (d) at least one cleavage site separating the first T-cell engaging domain and the inert binding partner.

In one embodiment, a two-component system for treating a condition characterized by the presence of unwanted cells is encompassed comprising a first component comprising a targeted T-cell engaging agent comprising:
  a. a first component comprising a targeted T-cell engaging agent comprising
    i. a first targeting moiety that is capable of targeting the unwanted cells;
    ii. a first T-cell engaging domain capable of T-cell engaging activity when binding a second T-cell engaging domain, wherein the second T-cell engaging domain is not part of the first component;
    iii. a first inert binding partner for the first T-cell engaging domain binding to the first T-cell engaging domain such that the first T-cell engaging domain does not bind to the second T-cell engaging domain unless the inert binding partner is removed; and
    iv. a cleavage site separating the first T-cell engaging domain and the first inert binding partner, wherein the cleavage site is:
      (1) cleaved by an enzyme expressed by the unwanted cells;
      (2) cleaved through a pH-sensitive cleavage reaction inside the unwanted cell;
      (3) cleaved by a complement-dependent cleavage reaction; or
      (4) cleaved by a protease that is colocalized to the unwanted cell by a targeting moiety that is the same or different from the targeting moiety in the agent,
  b. a second component comprising a second T-cell engaging domain capable of T-cell engaging activity when binding the first T-cell engaging domain, wherein the first and second T-cell engaging domains are capable of binding when neither is bound to an inert binding partner.

In another embodiment, the second component of the two-component system further comprises a second targeting moiety that is capable of targeting the unwanted cells.

In another embodiment, the second component of the two-component system further comprises a second inert binding partner for the second T-cell engaging domain binding to the second T-cell engaging domain such that the second T cell engaging domain does not bind to the first T-cell engaging domain unless the inert binding partner is removed and
  a. a cleavage site separating the second T-cell engaging domain and the second inert binding partner, wherein the cleavage site is:
    i. cleaved by an enzyme expressed by the unwanted cells;
    ii. cleaved through a pH-sensitive cleavage reaction inside the unwanted cell;
    iii. cleaved by a complement-dependent cleavage reaction; or iv. cleaved by a protease that is colocalized to the unwanted cell by a targeting moiety that is the same or different from the targeting moiety in the agent, wherein cleavage of the cleavage site causes loss of the inert binding partner and complementation with the first T-cell engaging domain of the two-component system.

In some embodiments, the first and second targeting moieties of the two-component system are the same.

In some embodiments, the first and second targeting moieties of the two-component system are different In some embodiments, the first and second cleavage sites are the same.

In some embodiments, the first and second cleavage sites are different.

In some embodiments, at least one cleavage site is a protease cleavage site. In some embodiments, the at least one cleavage site is capable of being cleaved outside the unwanted cells.

In some embodiments of the two-component system, at least one enzyme expressed by the unwanted cells is a protease.

In some embodiments of the two-component system, at least one inert binding partner specifically binds the T-cell engaging domain.

In some embodiments of the two-component system, at least one inert binding partner is a VH or VL domain.

In some embodiments of the two-component system, the T-cell engaging domain is a VH domain, the inert binding partner is a VL domain and when the T-cell engaging domain is a VL domain, the inert binding partner is a VH domain.

In some embodiments of the two-component system, at least one targeting moiety is an antibody or functional fragment thereof. In some embodiments of the two-component system, the at least one inert binding partner is capable of dissociation once at least one cleavage site has been cleaved and after dissociation the two T-cell engaging domains are capable of binding to each other and exhibiting T-cell engaging activity.

In some embodiments of the two-component system, a set of nucleic acid molecules encodes the first and second component of the two-component system. In some embodiments of the two-component system, a nucleic acid molecule encodes the component for use in a two-component system.

In some embodiments of the two-component system, one T-cell engaging domain is a VH domain and the other T-cell engaging domain is a VL domain.

In another embodiment, a component for use in a two-component system for treating a condition characterized by the presence of unwanted cells comprising a first targeted T-cell engaging agent comprises:

a. a targeting moiety that is capable of targeting the unwanted cells;
b. a first T-cell engaging domain capable of T-cell engaging activity when binding a second T-cell engaging domain, wherein the second T-cell engaging domain is not part of the first targeted T-cell engaging agent;
c. an inert binding partner for the first T-cell engaging domain binding to the first T-cell engaging domain such that the first T-cell engaging domain does not bind to the second T-cell engaging domain unless the inert binding partner is removed; and
d. a cleavage site separating the first T-cell engaging domain and the inert binding partner, wherein the cleavage site is:
  i. cleaved by an enzyme expressed by the unwanted cells;
  ii. cleaved through a pH-sensitive cleavage reaction inside the unwanted cell;
  iii. cleaved by a complement-dependent cleavage reaction; or cleaved by a protease that is colocalized to the unwanted cell by a targeting moiety that is the same or different from the targeting moiety in the agent, wherein cleavage of the cleavage site causes loss of the inert binding partner and allows for complementation with the second T-cell engaging domain that is not part of the agent.

In some embodiments, a method of treating a disease in a patient characterized by the presence of unwanted cells is encompassed that comprises administering the two-component system to the patient. In some embodiments, a method of targeting an immune response of a patient to unwanted cells is encompassed that comprises administering the two-component system. In some embodiments, these unwanted cells are cancer cells. In some embodiments, the cancer is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 4A-C illustrate the cleavage of the stepwise process of the pair of complementary components in a two-component system binding to the target cell (A), cleavage of linker attaching the inert binding partners (A and B), and binding to create an active moiety capable of T-cell FIGS. 5A-B provide evaluation of constructs by SDS PAGE and Coomassie blue staining.

FIG. 17 shows a sequence schematic for constructs 6248 and 6249 with the various linkers boxed and the protease cleavage site in bold and underline. The His tag is also in bold.

DESCRIPTION OF THE SEQUENCES

Figure 1:
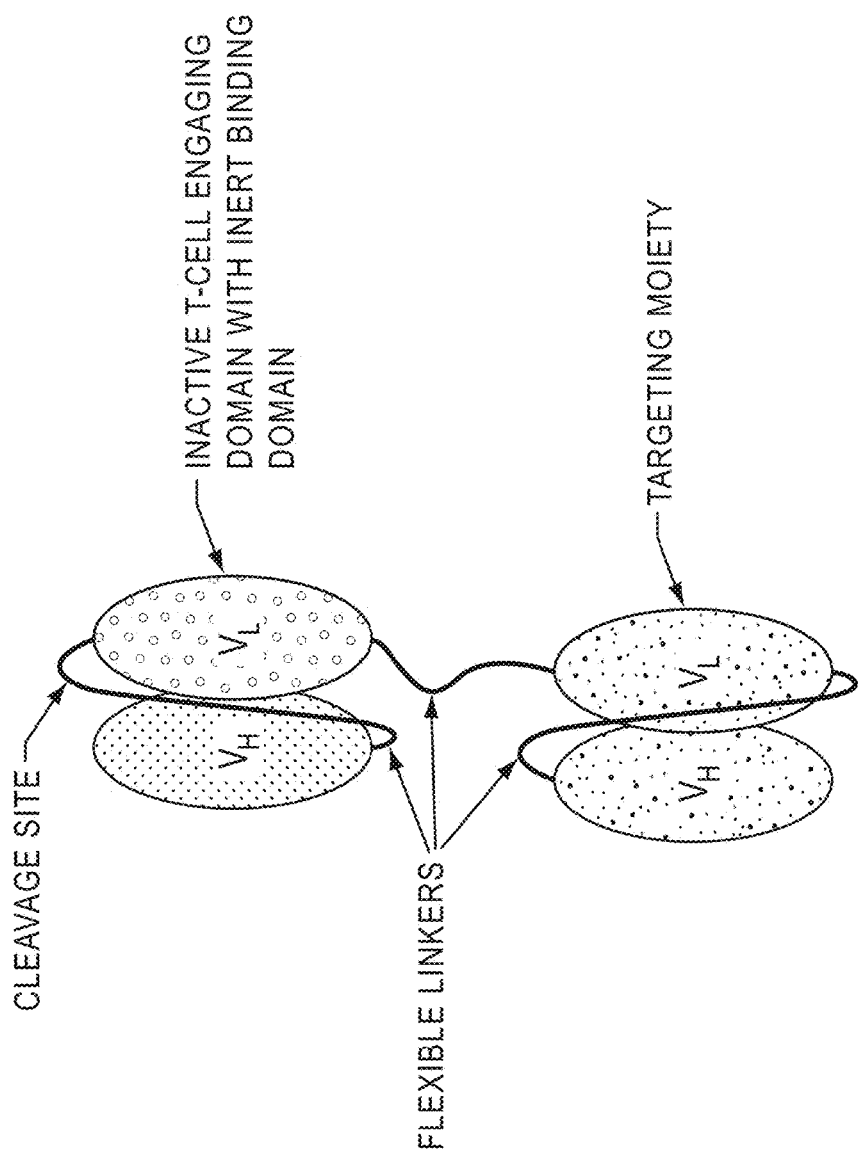
FIG. 1 shows one embodiment of a first component of a two-component system, where the first component is a targeted T-cell engaging agent in an inactive state with an inert binding partner.

Tables 1A and 1B provide a listing of certain sequences referenced herein.

TABLE 1A

Description of the Sequences and SEQ ID NOs

| Description | Sequence | # |
|---|---|---|
| ADAM28 cleavage site | KPAKFFRL | 1 |
| ADAM28 cleavage site | DPAKFFRL | 2 |
| ADAM28 cleavage site | KPMKFFRL | 3 |
| ADAM28 cleavage site | LPAKFFRL | 4 |
| ADAM28 cleavage site | LPMKFFRL | 5 |
| ADAM28 cleavage site | KPAMFFRL | 6 |
| ADAM28 cleavage site | YPAKFFRL | 7 |
| ADAM28 cleavage site | KWAKFFRL | 8 |
| ADAM28 cleavage site | DPMKFFRL | 9 |
| ADAM28 cleavage site | DPAMFFRL | 10 |
| ADAM28 cleavage site | DPMMFFRL | 11 |
| ADAM28 cleavage site | KMAMFFRL | 12 |
| ADAM28 cleavage site | KMAMFFIM | 13 |
| ADAM28 cleavage site | KPAMFFIM | 14 |
| ADAM28 cleavage site | LPAMFFRL | 15 |
| ADAM28 cleavage site | LPMMFFRL | 16 |
| ADAM28 cleavage site | LMAMFFRL | 17 |
| ADAM28 cleavage site | LMAMFFIM | 18 |
| ADAM28 cleavage site | LPAMFFIM | 19 |
| ADAM28 cleavage site | LPAMFFYM | 20 |
| ADAM28 cleavage site | KPMMFFRL | 21 |
| ADAM28 cleavage site | KPAKFFYM | 22 |

TABLE 1A-continued

Description of the Sequences and SEQ ID NOs

| Description | Sequence | # |
|---|---|---|
| ADAM28 cleavage site | KPAKFFIM | 23 |
| ADAM28 cleavage site | IPMKFFRL | 24 |
| ADAM28 cleavage site | IPAMFFRL | 25 |
| ADAM28 cleavage site | IPMMFFRL | 26 |
| ADAM28 cleavage site | IMAMFFRL | 27 |
| ADAM28 cleavage site | IMAMFFIM | 28 |
| ADAM28 cleavage site | IPAMFFIM | 29 |
| ADAM28 cleavage site | IPAMFFYM | 30 |
| cathepsin B cleavage site | FR | 31 |
| cathepsin B cleavage site | FK | 32 |
| cathepsin B cleavage site | VA | 33 |
| cathepsin B cleavage site | VR | 34 |
| cathepsin B cleavage site | V{Cit} | 35 |
| cathepsin B cleavage site | HLVEALYL | 36 |
| cathepsin B cleavage site | SLLKSRMVPNFN | 37 |
| cathepsin B cleavage site | SLLIARRMPNFN | 38 |
| cathepsin B cleavage site | KKFA | 39 |
| cathepsin B cleavage site | AFKK | 40 |
| cathepsin B cleavage site | QQQ | 41 |
| cathepsin D cleavage site | PRSFFRLGK | 42 |
| cathepsin D cleavage site | SGVVIATVIVIT | 43 |
| cathepsin K cleavage site | GGP | 44 |
| MMP1 cleavage site | SLGPQGIWGQFN | 45 |
| MMP2 cleavage site | AIPVSLR | 46 |
| MMP2 cleavage site | SLPLGLWAPNFN | 47 |
| MMP2 cleavage site | HPVGLLAR | 48 |
| MMP2 cleavage site | GPLGVRGK | 49 |
| MMP2 cleavage site | GPLGLWAQ | 50 |
| MMP3 cleavage site | STAVIVSA | 51 |
| MMP7 cleavage site | GPLGLARK | 52 |
| MMP7 cleavage site | RPLALWRS | 53 |
| MMP7 cleavage site | SLRPLALWRSFN | 54 |
| MMP2/9 cleavage site | GILGVP | 55 |
| MMP2/9 cleavage site | GPLGIAGQ | 56 |
| MMP9 cleavage site | AVRWLLTA | 57 |
| MMP9 cleavage site | PLGLYAL | 58 |
| MMP9 cleavage site | GPQGIAGQR | 59 |
| MMP9 cleavage site | KPVSLSYR | 60 |

TABLE 1A-continued

Description of the Sequences and SEQ ID NOs

| Description | Sequence | # |
|---|---|---|
| MMP11 cleavage site | AAATSIN | 61 |
| MMP11 cleavage site | AAGAMFLE | 62 |
| MMP13 cleavage site | GPQGLAGQRGIV | 63 |
| MMP14 cleavage site | PRHLR | 64 |
| MMP14 cleavage site | PQGLLGAPGILG | 65 |
| MMP14 cleavage site | PRSAKELR | 66 |
| PSA / KLK3 | HSSKLQ | 67 |
| PSA / KLK3 | SSKLQ | 68 |
| KLK4 | RQQR | 69 |
| TMPRSS2 | GGR | 70 |
| Legumain | AAN | 71 |
| ST14 (Matriptase) | QAR | 72 |
| C1s cleavage site | YLGRSYKV | 73 |
| C1s cleavage site | MQLGRX | 74 |
| MASP2 cleavage site | SLGRKIQI | 75 |
| C2a and Bb cleavage site | GLARSNLDE | 76 |
| uPa cleavage site | TYSRSRYL | 77 |
| uPa cleavage site | KKSPGRVVGGSV | 78 |
| uPa cleavage site | NSGRAVTY | 79 |
| uPa cleavage site | AFK | 80 |
| tissue-type plasminogen activator (tPA) | GGSGQRGRKALE | 81 |
| ADAM10 | PRYEAYKMGK | 82 |
| ADAM12 | LAQAF | 83 |
| ADAM17 | EHADLLAVVAK | 84 |
| flexible amino acid linker (may be presented in repeating fashion) | GGGGS | 85 |
| flexible amino acid linker (may be presented in repeating fashion) | GGGS | 86 |
| flexible amino acid linker (may be presented in repeating fashion) | GS | 87 |
| flexible amino acid linker (may be presented in repeating fashion) | GSGGS | 88 |
| flexible amino acid linker (may be presented in repeating fashion) | GGSG | 89 |
| flexible amino acid linker (may be presented in repeating fashion) | GGSGG | 90 |
| flexible amino acid linker (may be presented in repeating fashion) | GSGSG | 91 |

TABLE 1A-continued

Description of the Sequences and SEQ ID NOs

| Description | Sequence | # |
|---|---|---|
| flexible amino acid linker (may be presented in repeating fashion) | GSGGG | 92 |
| flexible amino acid linker (may be presented in repeating fashion) | GGGSG | 93 |
| flexible amino acid linker (may be presented in repeating fashion) | GSSSG | 94 |
| Anti-EGFR aptamer (tight binder with $K_d$ = 2.4 nM) | UGCCGCUAUAAUGCACGGAUUUAAUCGCCGUAGAAAAGCAUGUCAAAGCCG | 95 |
| Anti-EGFR aptamer | UGGCGCUAAAUAGCACGGAAAUAAUCGCCGUAGAAAAGCAUGUCAAAGCCG | 96 |
| Anti-EGFR aptamer | UGCUAGUAUAUCGCACGGAUUUAAUCGCCGUAGAAAAGCAUGUCAAAGCCG | 97 |
| Anti-EGFR aptamer | UGCCGCCAUAUCACACGGAUUUAAUCGCCGUAGAAAAGCAUGUCAAAGCCG | 98 |
| Anti-EGFR aptamer | UUCCGCUGUAUAACACGGACUUAAUCGCCGUAGUAAAGCAUGUCAAAGCCG | 99 |
| Anti-EGFR aptamer | UGUCGCUCUAUUGCACGGAUUUAAUCGCCGUAGAAAAGCAUGUCAAAGCCG | 100 |
| Anti-EGFR aptamer | UGCUGCUUUAUCCCACAUAUUUUUCCCCUCAUAACAAUAUUUCUCCCCCC | 101 |
| Anti-EGFR aptamer | UGCNGCUAUAUCGCNCGUAUUUAAUCGCCGUAGAAAAGCAUGUCNANGCCG | 102 |
| Anti-EGFR aptamer | UGCAAAGAAAACGCACGUAUUUAAUCGCCGUAGUAAAGCAUGUCAAAGCCG | 103 |
| Anti-EGFR aptamer | UGCAUCACUAUCGAACCUAUUUAAUCCACCAAAAUAAUUGCAAGUCCAUACUC | 104 |
| Anti-EGFR aptamer | UGCCNNAAUAACACACNUAUAUAAUCGCCGUACAAAAUCAUGUCAAANCCG | 105 |
| Anti-EGFR aptamer | UGCAGCUGUAUUGCACGUAUUUAAUCGCCGUAGAAAAGCAUGUCAAAGCCG | 106 |
| Anti-EGFR aptamer | UUCCGAUAAUCCCGCGUACUAAAUCACCAUAGUCAACAAUUUCCAACCUC | 107 |
| Anti-EGFR aptamer | UCCACUAUAUCACACGUAUUUAAUCGCCGUAGAAAAGCAUGUCAAAGCCG | 108 |
| Anti-EGFR aptamer | UCCCUCAACCUCGCUACUAUUUAAUCGCCGUAGAAAAGCAUGUCAAAGCCU | 109 |
| Anti-EGFR aptamer | UGCCGCUAUAUCACACGAAUUUAAUCGCCGUAGAAAAGCAUGUCAAAGCCG | 110 |
| Anti-EGFR aptamer | AGCCCCUAGAACACACGGAUUUAAUCGCCGUAGAAAAGCAUGUCAAAGCCG | 111 |
| Anti-EGFR aptamer | UGCCAAUAUAUAACACGGAAUUUAAUCGCCGUAGAAAAGCAUGUCAAAGCCG | 112 |
| Anti-EGFR aptamer | UGCCGCUAUAGCGCACGGAUUUAAUCGCCGUAGAAAAGCAUGUCAAAGCCG | 113 |
| Anti-EGFR aptamer | UGCAGAUAUAUGUCACUCAUUAAUCCCCGUAUAAAAACAUAACUAAGCUC | 114 |
| Anti-EGFR aptamer | UGUAGCUGUAUUGCACACAUUAAAUCGCCGUAGUAAAGCAUGUCAAAGCCG | 115 |

TABLE 1A-continued

Description of the Sequences and SEQ ID NOs

| Description | Sequence | # |
| --- | --- | --- |
| Anti-EGFR aptamer | UACCAAUAUAUCGCCACACAUAAUCG CCGUAGAAAAGCAUGUCAAAGCCG | 116 |
| Anti-EGFR aptamer | UGCCGCUAUGCCCACGGAAUUUAAUC GCCGUAGAAAAACAUGUCAAAGUCG | 117 |
| Anti-EGFR aptamer | UGCCGCUAUUUAGCACGGAUUAAAUC GCCGUAGAAAAGCAUGUCAAAGCCG | 118 |
| Anti-EGFR aptamer | UGCCGCUAUUUAGCACGGAUUAAAUC GCCGUAGAAAAGCAUGUCNAAGCCG | 119 |
| Anti-EGFR aptamer | UGUAGUAAUAUGACACGGAUUUAAUC GCCGUAGAAAAGCANGUCAAAGCCU | 120 |
| Anti-EGFR aptamer | UGUCGCCAUUACGCACGGAUUUAAUC GCCGUAGAAAAGCAUGUCAAAGCCG | 121 |
| Anti-EGFR aptamer | UGCCCCAAACUACACAAAUUUAAUC GCCGUAUAAAAGCAUGUCAAAGCCG | 122 |
| Anti-EGFR aptamer | UGCACUAUCUCACACGUACUAAUCGC CGUAUAAAAGCAUGUCAAAGCCG | 123 |
| Anti-EGFR aptamer | UGUCGCAAUAAUACACUAAUUUAAUC GCCGUAGAAAAGCAUGUCAAAGCCG | 124 |
| Anti-EGFR aptamer | UGCAACAAUAUAGCACGUAUUUAAUC GCCGUAGUAAAGCAUGUCAAAGG | 125 |
| Anti-EGFR aptamer | CUACCACAAAUCCCACAUAUUUAAUC UCCCAAUCAAAUCUUGUCCAUUCCC | 126 |
| Anti-EGFR aptamer | UGCCCUAAACUCACACGGAUAUAAUC GCCGUAGAAAAGCAUGUCAAAGCCG | 127 |
| Anti-EGFR aptamer | UUGUCGUAUGUCACACGUAUUAAAUC GCCGUAUAAAAGCAUGUCAAAGCCG | 128 |
| Anti-EGFR aptamer | UUCCGCUAUAACACACGGAGAAAAUC GCCGUAGUAAAGCAUGUCAAAGCCG | 129 |
| Anti-EGFR aptamer | UGCCGAUAUAACGCACGGAUAUAAUC GCCGUAGAAAAGCAUGUCAAAGCCG | 130 |
| Anti-EGFR aptamer | UGCCAUUAUACAGCACGGAUUUAAUC GCCGUAGAAAAGCAUGUCAAAGCCG | 131 |
| Anti-EGFR aptamer | UCCAGAAAUAUGCACACAUUUAAUCG CCGUAGAAAAGCAUGUCAAAGCCG | 132 |
| Anti-EGFR aptamer | UCCGCUAAACAACACGGAUACAAUCG CCGUAGAAAAGCAUGUCCAAGCCG | 133 |
| Anti-EGFR aptamer | UGCACUAUCUCACACGUACUAAUCGC CGUAUAAAAGCAUGUCAAANNNG | 134 |
| Anti-EGFR aptamer | AUNGCNANNNUACACGUAUUNAAUCG CCGUAGAAAAGCAUGUCANAGCCG | 135 |
| Anti-EGFR aptamer | UGCUGCUAUAUUGCAAUUUUUUAAAC UAAGUAGAAACCAUGUACAAGUCG | 136 |
| Anti-EGFR aptamer | UGUCGCCAUAUUGCACGGAUUUAAUC GCCGUAGAAAAGCAUGUCCAAGCCG | 137 |
| Anti-EGFR aptamer | UGCCGUUAUAACCCACGGAAUUUAAC CUCCGUAGAAAAGCAUGUCAAAGCCG | 138 |
| Anti-EGFR aptamer | UGUGAAUAUAUAUCACGGAUUUAAUC GCCGUAUAAAAGCNAUGUCAAAGCCG | 139 |
| Anti-EGFR aptamer | UGCCGAUAUNNANCACGGAUUUAAUC GCCGUAGAAAAGCAUGUCCAAGCCG | 140 |

TABLE 1A-continued

Description of the Sequences and SEQ ID NOs

| Description | Sequence | # |
|---|---|---|
| Anti-EGFR aptamer | UGUCACUAAAUUGCACGUAUAUAAUC GCCGUAGUAAGCAUGUCAAAGCCG | 141 |
| Anti-EGFR aptamer | UGCAACCAUAAAGCACGUAAUAAAUC GCCGUAUAUAAGCAUGUCaAAGCCG | 142 |
| Anti-EGFR aptamer | UGCCGCUAUAUAGCACGUAUUAAUCG CCGUAGUAAAGCAUGUCaAAGCCG | 143 |
| Anti-EGFR aptamer | UGCCGCUAUAGCACACGGAAUUUAAU CGCCGUAGUAAAGCAUGUCAAAGCCG | 144 |
| Anti-EGFR aptamer | UGCAGGUAUAUAACNCGGAUUUAAUC GCCGUAGAAAAGCAUGUCNAAGCCG | 145 |
| Anti-EGFR aptamer | UGCUCCUAUAACACACGGAUUUAAUC GCCGUAGAAAAGCAUGUCCAAGCCG | 146 |
| Anti-EGFR aptamer | UGCCCGUAAUUGCACGGAUUUAAUCG CCGUAGAAAAGCAUGUCCAAGCCGG | 147 |
| Anti-EGFR aptamer | ACUCCCUAUAUNGCAACUACAUAAUC GCCGUAAAAUAAGCAUGUNCAAGCCG | 148 |
| Anti-EGFR aptamer | UGAAGCUAGAUCACACUAAAUUAAUC GCCGUAGAAAAGCAUGUCAAAAAAGC CG | 149 |
| Anti-EGFR aptamer | UGACUCUUUAUCCCCCGUACAUUAUU cACCGACCAAAGCAUUACCAUCCCC | 150 |
| Anti-EGFR aptamer | UGACGCCCUAACACACGUAUAUAAUC GCCGUAGAAAAGCAUGUCAAAGCCG | 151 |
| Anti-EGFR aptamer | UGUCGCAAAAUAGCACGUAUUUAAUC GCCGUAGAAAAGCAUGUCCAAGCCG | 152 |
| Anti-EGFR aptamer | UGAGUGUAUAAUUCACGUAUUUAAUC GCCGUAGAAAAGCAUGUCAAAGCCG | 153 |
| Anti-EGFR aptamer | UGCUACUAUAUCGUAGGUAACUAAUC GCCCUACAAACUCACUCUAAAACCG | 154 |
| Anti-EGFR aptamer | UUACGCUAUAUCACACGGAAUUUUAA UCGCCGUAGAAAAGCAUGUCCAAGCC G | 155 |
| Anti-EGFR aptamer | CCCAUCUGUACUACAGGAAUUUAAUC GCCGUAGAAAAGCAUGUCCAAGCCG | 156 |
| Anti-EGFR aptamer | UGCCCAUAAAUAGCACGGAUUUAAUC GCCGUAGAAAAGCAUGUCCAAGCCG | 157 |
| Anti-EGFR aptamer | UGCCGCAAUAACAUACACAUAUAAUC GCCGUAGAAAAGCAUGUCAAAGCCG | 158 |
| Anti-EGFR aptamer | UGCAACUAUAUCGCACGUAUGUAAUC GCCGUAGAAAAGCAUGUCAAAGCC | 159 |
| Anti-EGFR aptamer | UUCCGCUAUAUAGCACGGAAUUAAUC GCCGUAGAAAAGCAUGUCCAAGCCG | 160 |
| Anti-EGFR aptamer | UUCCGCUAAGUCACACGAAAUUAAUC GCCGUAGAAAAGCAUGUCCAAGCCG | 161 |
| Anti-EGFR aptamer | UGUAGCAAUAUCACACGUAAUUAAUC GCCGUAUAUAAGCAUGUCAAAGCCG | 162 |
| Anti-EGFR aptamer | UGCCGUUAUAUAUCACGGAUUUAAUC GCCGUAGAAAAGCAUGUCCAAGCCG | 163 |
| Anti-EGFR aptamer | UAACACAUAUAUCAAGUAACUUAUCU CCUUAGUAACCAUCUCCAAGCCG | 164 |
| HLA-A*0201-restricted viral peptide | NLVPMVATV | 178 |

TABLE 1B

Description of Construct Sequences and SEQ ID NOs

| Description | Sequence | # |
|---|---|---|
| Construct 6245 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH(IGHV1-54*01 (85.90%)-(IGHD)-IGHJ4*01, S123 > T(243))[8.8.14] (129-248)]-5-mer tetraglycyl-seryl linker (249-253)-scFv anti-CD3E [humanized VH (Homo sapiens IGHV1-46*01 (82.50%)-(IGHD)-IGHJ6*01)[8.8.12](254-372)-18-mer linker (373-390)-V-KAPPA (Mus musculus IGKV4-59*01 (81.70%)-IGKJ1*01 L124 > V (493) [5.3.9](391-496)]-hexahistidine (497-502) CAS Registry Number 1005198-65-1 ChemID: 1005198-65-1 | ELVMTQSPSSLTVTAGEKVIMSCKSS QSLLNSGNQKNYLTWYQQKPGQPPKL LIYWASTRESGVPDRFTGSGSGTDFT LTISSVQAEDLAVYYCQNDYSYPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDVQLVQS GAEVKKPGASVKVSCKASGYTFTRYT MHWVRQAPGQGLEWIGYINPSRGYTN YADSVKGRFTITTDKSTSTAYMELSS LRSEDTATYYCARYYDDHYCLDYWGQ GTTVTVSSGEGTSTGSGGSGGSGGAD DIVLTQSPATLSLSPGERATLSCRAS QSVSYMNWYQQKPGKAPKRWIYDTSK VASGVPARFSGSGSGTDYSLTINSLE AEDAATYYCQQWSSNPLTFGGGTKVE IKHHHHHH | 165 |
| Construct 6246 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH(IGHV1-54*01 (85.90%)-(IGHD)-IGHJ4*01, S123 > T(243))[8.8.14] (129-248)]-5-mer tetraglycyl-seryl linker (249-253)-scFv anti-CD3E [humanized VH (Homo sapiens IGHV1-46*01 (82.50%)-(IGHD)-IGHJ6*01)[8.8.12](254-372)-18-mer linker (373-390 -hexahistidine (391-396) | ELVMTQSPSSLTVTAGEKVIMSCKSS QSLLNSGNQKNYLTWYQQKPGQPPKL LIYWASTRESGVPDRFTGSGSGTDFT LTISSVQAEDLAVYYCQNDYSYPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDVQLVQS GAEVKKPGASVKVSCKASGYTFTRYT MHWVRQAPGQGLEWIGYINPSRGYTN YADSVKGRFTITTDKSTSTAYMELSS LRSEDTATYYCARYYDDHYCLDYWGQ GTTVTVSSGEGTSTGSGGSGGSGGAD HHHHHH | 166 |
| Construct 6247 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH(IGHV1-54*01 (85.90%)-(IGHD)-IGHJ4*01, S123 > T (243))[8.8.14] (129-248)]-5-mer tetraglycyl-seryl linker (249-253)-anti-CD3E-V-KAPPA (Mus musculus IGKV4-59*01 (81.70%)-IGKJ1*01 L124 > V (356) [5.3.9](254-359)1-hexahistidine (360-365) | ELVMTQSPSSLTVTAGEKVIMSCKSS QSLLNSGNQKNYLTWYQQKPGQPPKL LIYWASTRESGVPDRFTGSGSGTDFT LTISSVQAEDLAVYYCQNDYSYPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDIVLTQS PATLSLSPGERATLSCRASQSVSYMN WYQQKPGKAPKRWIYDTSKVASGVPA RFSGSGSGTDYSLTINSLEAEDAATY YCQQWSSNPLTFGGGTKVEIKHHHHH H | 167 |
| Construct 6248 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH(IGHV1-54*01 (85.90%)-(IGHD)-IGHJ4*01, S123 > T (243))[8.8.14] (129-248)]-5-mer tetraglycyl-seryl linker (249-253)-scFv anti-CD3E [humanized VH (Homo sapiens IGHV1-46*01 (82.50%)-(IGHD)-IGHJ6*01)[8.8.12](254-372)-25-mer linker (373-397 containing | ELVMTQSPSSLTVTAGEKVIMSCKSS QSLLNSGNQKNYLTWYQQKPGQPPKL LIYWASTRESGVPDRFTGSGSGTDFT LTISSVQAEDLAVYYCQNDYSYPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDVQLVQS GAEVKKPGASVKVSCKASGYTFTRYT MHWVRQAPGQGLEWIGYINPSRGYTN YADSVKGRFTITTDKSTSTAYMELSS LRSEDTATYYCARYYDDHYCLDYWGQ GTTVTVSSGEGTSTGSGAIPVSLRGS GGSGGADDIVLTQSPATLSLSPGERA | 168 |

TABLE 1B-continued

Description of Construct Sequences and SEQ ID NOs

| Description | Sequence | # |
|---|---|---|
| MMP2 cleavage site AIPVSLR (SEQ ID NO: 46))-V-KAPPA (Homo sapiens V-KAPPA from gantenerumab, CAS: 1043556-46-2; 398-505); 87-hexahistidine (506-511) | TLSCRASQSVSSSYLAWYQQKPGQAP RLLIYGASSRATGVPARFSGSGSGTD FTLTISSLEPEDFATYYCLQIYNMPI TFGQGTKVEIKHHHHHH | |
| Construct 6249 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH (IGHV1-54*01 (85.90%)-(IGHD)-IGHJ4*01, S123 > T(243))[8.8.14] (129-248)]-5-mer tetraglycyl-seryl linker (249-253)-scFv anti-CD3E V-KAPPA (Mus musculus IGKV4-59*01 (81.70%)-IGKJ1*01 L124 > V (493)[5.3.9](254-359)]-25-mer linker (360-384 containing MMP2 cleavage site AIPVSLR (SEQ ID NO: 46))-Ig heavy chain V region (clone alpha-MUC1-1, GenBank Accession S36265; 385-502)-hexahistidine (503-508) | ELVMTQSPSSLTVTAGEKVTMSCKSS QSLLNSGNQKNYLTWYQQKPGQPPKL LIYWASTRESGVPDRFTGSGSGTDFT LTISSVQAEDLAVYYCQNDYSPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDIVLTQS PATLSLSPGERATLSCRASQSVSYMN WYQQKPGKAPKRWIYDTSKVASGVPA RFSGSGSGTDYSLTINSLEAEDAATY YCQQWSSNPLTFGGGTKVEIKGEGTS TGSGAIPVSLRGSGGSGGADDVQLVQ SGAEVKKPGASVKVSCKASGYTFTGY YMHWVRQAPGQGLEWMGWINPNSGGT NYAQKFQGRVTITRDTSASTAYMELS SLRSEDTAVYYCARDFLSGYLDYWGQ GTLVTVSSHHHHHH | 169 |
| Construct 9327 EpCAM $V_LV_H$-$V_HDV_L$ single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH (IGHV1-54*01 (85.90%)-(IGHD)-IGHJ4*01, S123 > T(243))[8.8.14] (129-248)]-5-mer tetraglycyl-seryl linker (249-253)-scFv anti-CD3E [humanized VH (Homo sapiens IGHV1-46*01 (82.50%)-(IGHD)-IGHJ6*01)[8.8.12](254-372)-25-mer linker (373-397)-V-KAPPA (Homo sapiens V-KAPPA from gantenerumab, CAS: 1043556-46-2; 398-505);-hexahistidine (506-511) Anti-EpCAM sequence from Brischwein K et al, Mol. Immunol. (2006) 43: 1129-43 | ELVMTQSPSSLTVTAGEKVTMSCKSS QSLLNSGNQKNYLTWYQQKPGQPPKL LIYWASTRESGVPDRFTGSGSGTDFT LTISSVQAEDLAVYYCQNDYSPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDVQLVQS GAEVKKPGASVKVSCKASGYTFTRYT MHWVRQAPGQGLEWIGYINPSRGYTN YADSVKGRFTITTDKSTSTAYMELSS LRSEDTATYYCARYYDDHYCLDYWGQ GTTVTVSSGEGTSTGSGGGGSGGGGS GGSGGADDIVLTQSPATLSLSPGERA TLSCRASQSVSSSYLAWYQQKPGQAP RLLIYGASSRATGVPARFSGSGSGTD FTLTISSLEPEDFATYYCLQIYNMPI TFGQGTKVEIKHHHHHH | 170 |
| Construct 9328 single chain; scFv anti-EPCAM [Mus musculus V-KAPPA (IGKV8-19*01 (98.00%)-IGKJ5*01 L126 > I(112)) [12.3.9](1-113)-15-mer tris(tetraglycyl-seryl) linker (114-128)-Mus musculus VH (IGHV1-54*01 (85.90%)-(IGHD)-IGHJ4*01, S123 > T(243))[8.8.14] (129-248)]-5-mer tetraglycyl-seryl linker (249-253)-scFv anti-CD3E V-KAPPA (Mus musculus IGKV4-59*01 (81.70%)-IGKJ1*01 L124 > V (493)[5.3.9](254-359)]-25-mer linker (360-384)-Ig heavy chain V region (clone alpha-MUC1-1, GenBank Accession S36265; 385-502)-hexahistidine (503-508) | ELVMTQSPSSLTVTAGEKVTMSCKSS QSLLNSGNQKNYLTWYQQKPGQPPKL LIYWASTRESGVPDRFTGSGSGTDFT LTISSVQAEDLAVYYCQNDYSPLTF GAGTKLEIKGGGGSGGGGSGGGGSEV QLLEQSGAELVRPGTSVKISCKASGY AFTNYWLGWVKQRPGHGLEWIGDIFP GSGNIHYNEKFKGKATLTADKSSSTA YMQLSSLTFEDSAVYFCARLRNWDEP MDYWGQGTTVTVSSGGGGSDIVLTQS PATLSLSPGERATLSCRASQSVSYMN WYQQKPGKAPKRWIYDTSKVASGVPA RFSGSGSGTDYSLTINSLEAEDAATY YCQQWSSNPLTFGGGTKVEIKGEGTS TGSGGGGSGGGGSGGSGGADDVQLVQ SGAEVKKPGASVKVSCKASGYTFTGY YMHWVRQAPGQGLEWMGWINPNSGGT NYAQKFQGRVTITRDTSASTAYMELS SLRSEDTAVYYCARDFLSGYLDYWGQ GTLVTVSSHHHHHH | 171 |

TABLE 1B-continued

Description of Construct Sequences and SEQ ID NOs

| Description | Sequence | # |
|---|---|---|
| Construct 9329<br>Glypican3 $V_{HH}$-CD3ε ($V_H$-MMP2-$V_L$)<br>Anti-human Glypican-3 VHH sequence from U.S. Pat. No. 2012145469; residues 1-116)-5-mer tris(tetraglycyl-seryl) linker (117-122)-scFv anti-CD3ε [humanized VH (Homo sapiens IGHV1-46*01 (82.50%)-(IGHD)-IGHJ6*01) [8.8.12](123-241)-25-mer linker (242-266 containing MMP2 cleavage site AIPVSLR (SEQ ID NO: 46))-V-KAPPA (Homo sapiens V-KAPPA from gantenerumab, CAS: 1043556-46-2; 267-374); -hexahistidine (375-380) | QVQLVQSGGGLVQPGGSLRLSCAASY FDFDSYEMSWVRQAPGKGLEWIGSIY HSGSTYYNPSLKSRVTISRDNSKNTL YLQMNTLRAEDTATYYCARVNMDRFD YWGQGTLVTVSSSGGGGSDVQLVQSG AEVKKPGASVKVSCKASGYTFTRYTM HWVRQAPGQGLEWIGYINPSRGYTNY ADSVKGRFTITTDKSTSTAYMELSSL RSEDTATYYCARYYDDHYCLDYWGQG TTVTVSSGEGTSTGSGAIPVSLRGSG GSGGADDIVLTQSPATLSLSPGERAT LSCRASQSVSSSYLAWYQQKPGQAPR LLIYGASSRATGVPARFSGSGSGTDF TLTISSLEPEDFATYYCLQIYNMPIT FGQGTKVEIKHHHHHH | 172 |
| Construct 9330<br>anti-[Homo sapiens SDC1 (syndecan-1, CD138), scFv, from indatuximab CAS: 1238517-16-2, U.S. Pat. No. U520140010828], [Mus musculus V-KAPPA (IGKV10-94*01-IGKJ1*01)[6.3.9](1-108) - 15-mer tris(tetraglycyl-seryl) linker (109-123) [Mus musculus VH (IGHV1-9*01 - (IGHD)-IGHJ4*01)[8.8.15](124-245)-5-mer tris(tetraglycyl-seryl) linker (246-250)-scFv anti-CD3ε [humanized VH (Homo sapiens IGHV1-46*01 (82.50%)-(IGHD)-IGHJ6*01)[8.8.12](251-369)-25-mer linker (370-394 containing MMP2 cleavage site AIPVSLR (SEQ ID NO: 46))-V-KAPPA (Homo sapiens V-KAPPA from gantenerumab, CAS: 1043556-46-2; 395-502); -hexahistidine (503-508) | DIQMTQSTSSLSASLGDRVTISCSAS QGINNYLNWYQQKPDGTVELLIYYTS TLQSGVPSRFSGSGSGTDYSLTISNL EPEDIGTYYCQQYSKLPRTFGGGTKL EIKRGGGGSGGGGSGGGGSQVQLQQS GSELMMPGASVKISCKATGYTFSNYW IEWVKQRPGHGLEWIGEILPGTGRTI YNEKFKGKATFTADISSNTVQMLSSL TSEDSAVYYCARRDYYGNFYYAMDY WGQGTSVTVSSGGGGSDVQLVQSGAE VKKPGASVKVSCKASGYTFTRYTMHW VRQAPGQGLEWIGYINPSRGYTNYAD SVKGRFTITTDKSTSTAYMELSSLRS EDTATYYCARYYDDHYCLDYWGQGTT VTVSSGEGTSTGSGAIPVSLRGSGGS GGADDIVLTQSPATLSLSPGERATLS CRASQSVSSSYLAWYQQKPGQAPRLL IYGASSRATGVPARFSGSGSGTDFTL TISSLEPEDFATYYCLQIYNMPITFG QGTKVEIKHHHHHH | 173 |
| Construct 9332<br>EGFR $V_{HH}$-CD3ε ($V_H$-$V_L$)<br>Anti-human EGFR $V_{HH}$ sequence from 7D12 sequence from Schmitz KR et al, Structure. 2013 July 2; 21(7): 1214-24; residues 1-124)-30-mer tris(tetraglycyl-seryl) linker (125-154)-scFv anti-CD3ε [humanized VH (Homo sapiens IGHV1-46*01 (82.50%)-(IGHD)-IGHJ6*01)[8.8.12](155-273)-18-mer linker (274-291) -V-KAPPA (Mus musculus IGKV4-59*01 (81.70%)-IGKJ1*01 L124 > V (394) [5.3.9](292-397)]-hexahistidine (398-403)<br>Anti-human CD3ε sequence from Brischwein K et al, Mol. Immunol. (2006) 43: 1129-43<br>U.S. Pat. No. US7919089 | QVKLEESGGGSVQTGGSLRLTCAASG RTSRSYGMGWFRQAPGKEREFVSGIS WRGDSTGYADSVKGRFTISRDNAKNT VDLQMNSLKPEDTAIYYCAAAAGSAW YGTLYEYDYWGQGTQVTVSSGGGGSG GGGSGGGGSGGGGSGGGGSGGGGSDV QLVQSGAEVKKPGASVKVSCKASGYT FTRYTMHWVRQAPGQGLEWIGYINPS RGYTNYADSVKGRFTITTDKSTSTAY MELSSLRSEDTATYYCARYYDDHYCL DYWGQGTTVTVSSGEGTSTGSGGSGG SGGADDIVLTQSPATLSLSPGERATL SCRASQSVSYMNWYQQKPGKAPKRWI YDTSKVASGVPARFSGSGSGTDYSLT INSLEAEDAATYYCQQWSSNPLTFGG GTKVEIKHHHHHH | 174 |
| Construct 9333<br>EGFR $V_{HH}$-CD3ε ($V_H$-$V_L$)<br>Anti-human EGFR $V_{HH}$ sequence from 9G8 sequence from Schmitz KR et al, Structure. 2013 July 2; 21(7): 1214-24; residues 1-127)-30-mer tris(tetraglycyl-seryl) linker (128-157)-scFv anti-CD3ε [humanized VH (Homo sapiens IGHV1-46*01 (82.50%)-(IGHD)-IGHJ6*01)[8.8.12](158-276)-18-mer linker (277-294)-V-KAPPA (Mus musculus IGKV4-59*01 | EVQLVESGGGLVQAGGSLRLSCAASG RTFSSYAMGWFRQAPGKEREFVVAIN WSSGSTYYADSVKGRFTISRDNAKNT MYLQMNSLKPEDTAVYYCAAGYQINS GNYNFKDYEYDYWGQGTQVTVSSGGG GSGGGGSGGGGSGGGGSGGGGSGGGG SDVQLVQSGAEVKKPGASVKVSCKAS GYTFTRYTMHWVRQAPGQGLEWIGYI NPSRGYTNYADSVKGRFTITTDKSTS TAYMELSSLRSEDTATYYCARYYDDH YCLDYWGQGTTVTVSSGEGTSTGSGG SGGSGGADDIVLTQSPATLSLSPGER ATLSCRASQSVSYMNWYQQKPGKAPK | 175 |

TABLE 1B-continued

Description of Construct Sequences and SEQ ID NOs

| Description | Sequence | # |
|---|---|---|
| (81.70%)-IGKJ1*01 L124 > V (394) [5.3.9](292-397)]-hexahistidine (401-406) | RWIYDTSKVASGVPARFSGSGSGTDY SLTINSLEAEDAATYYCQQWSSNPLT FGGGTKVEIKHHHHHH | |
| Construct 9334 EGFR $V_{HH}$-CD3ε($V_H$-MMP2-$V_L$) Anti-human EGFR $V_{HH}$ sequence from 7D12 sequence from Schmitz KR et al, Structure. 2013 July 2; 21(7): 1214-24; residues 1-124)- 30-mer tris(tetraglycyl-seryl) linker (125-154)- scFv anti-CD3E [humanized VH (Homo sapiens IGHV1-46*01 (82.50%)-(IGHD)- IGHJ6*01)[8.8.12](155-273)-25- mer linker (274-298 containing MMP2 cleavage site AIPVSLR (SEQ ID NO: 46))-V-KAPPA (Homo sapiens V-KAPPA from gantenerumab, CAS: 1043556-46-2; 299-406); -hexahistidine (407-412) | QVKLEESGGGSVQTGGSLRLTCAASG RTSRSYGMGWFRQAPGKEREFVSGIS WRGDSTGYADSVKGRFTISRDNAKNT VDLQMNSLKPEDTAIYYCAAAAGSAW YGTLYEYDYWGQGTQVTVSSGGGGSG GGGSGGGGSGGGGSGGGGSGGGGSDV QLVQSGAEVKKPGASVKVSCKASGYT FTRYTMHWVRQAPGQGLEWIGYINPS RGYTNYADSVKGRFTITTDKSTSTAY MELSSLRSEDTATYYCARYYDDHYCL DYWGQGTTVTVSSGEGTSTGSGAIPV SLRGSGGSGGADDIVLTQSPATLSLS PGERATLSCRASQSVSSSYLAWYQQK PGQAPRLLIYGASSRATGVPARFSGS GSGTDFTLTISSLEPEDFATYYCLQI YNMPITFGQGTKVEIKHHHHHH | 176 |
| Construct 9335 Anti-human EGFR $V_{HH}$ sequence from 9G8 sequence from Schmitz KR et al, Structure. 2013 July 2; 21(7): 1214-24; residues 1-127)- 30-mer tris(tetraglycyl-seryl) linker (128-157)- scFv anti-CD3E V-KAPPA (Mus musculus IGKV4- 59*01 (81.70%)-IGKJ1*01 L124 > V (493)[5.3.9](158-263)]-25-mer linker (264-288 containing MMP2 cleavage site AIPVSLR (SEQ ID NO: 46))-Ig heavy chain V region (clone alpha-MUC1-1, GenBank Accession S36265; 289-406)- hexahistidine (307-412) | EVQLVESGGGLVQAGGSLRLSCAASG RTFSSYAMGWFRQAPGKEREFVVAIN WSSGSTYYADSVKGRFTISRDNAKNT MYLQMNSLKPEDTAVYYCAAGYQINS GNYNFKDYEYDYWGQGTQVTVSSGGG GSGGGGSGGGGSGGGGSGGGGSGGGG SDIVLTQSPATLSLSPGERATLSCRA SQSVSYMNWYQQKPGKAPKRWIYDTS KVASGVPARFSGSGSGTDYSLTINSL EAEDAATYYCQQWSSNPLTFGGGTKV EIKGEGTSTGSGAIPVSLRGSGGSGG ADDVQLVQSGAEVKKPGASVKVSCKA SGYTFTGYYMHWVRQAPGQGLEWMGW INPNSGGTNYAQKFQGRVTITRDTSA STAYMELSSLRSEDTAVYYCARDFLS GYLDYWGQGTLVTVSSHHHHHH | 177 |

DESCRIPTION OF THE EMBODIMENTS

I. A Two-Component System Comprising at Least One Targeted T-Cell Engaging Agent A variety of targeted T-cell engaging agents are described in different embodiments, and in some embodiment as part of a two-component system comprising a first component and a second component. In each of the embodiments, however, a targeting moiety may be used to deliver the targeted T-cell engaging agent to an area of unwanted cells, allowing for a therapeutic effect to be delivered locally. The targeted T-cell engaging agent also contains a first T-cell engaging domain capable of activity when binding a second T-cell engaging domain, but the second T-cell engaging domain is not part of the targeted T-cell engaging agent. In other words, without the second T-cell engaging domain that is not part of the targeted T-cell engaging agent, the first T-cell engaging domain is not capable of T-cell engaging activity. The targeted T-cell engaging agent also comprises an inert binding partner capable of binding the first T-cell engaging domain and preventing it from binding to a second T-cell engaging domain. In other words, the inert binding partner binds to the first T-cell engaging domain such that the first T-cell engaging domain does not bind to the second T-cell engaging domain unless the inert binding partner is removed. By does not bind, the application does not exclude nonspecific binding or low levels of binding (for example, ≤1%, ≤5%, ≤10%). The concept is one of functional insufficiency with the de novo VH/VL complementation insufficient for T-cell target binding. Proteolytic cleavage liberates the inert VH or VL groups allowing the opportunity for re-pairing of active VH and VL pairs at the cell surface. Furthermore, the targeted T-cell engaging agent includes a cleavage site separating the first T-cell engaging domain and the inert binding partner. The cleavage site is cleaved when the targeted T-cell engaging agent is in the microenvironment of the unwanted cells.

In some embodiments, the second T-cell engaging domain is part of a second targeted T-cell engaging agent. Thus, in some embodiments, a kit or composition may comprise two targeted T-cell engaging agents, one with a first T-cell engaging domain and another with a second T-cell engaging domain. In such a kit or composition, the inert binding partners may be capable of dissociation once the cleavage site in each agent has been cleaved; after dissociation, the two T-cell engaging domains may be capable of binding to each other and exhibiting activity.

In some embodiments with two targeted T-cell engaging agents, the two-component system comprises one T-cell engaging domain that may be a VH domain and another T-cell engaging domain that may be a VL domain. In embodiments with two targeted T-cell engaging agents, the targeting moieties in the first component and the second component may be the same or they may be different.

In embodiments with two targeted T-cell engaging agents, the cleavage sites in the first component and the second component may be the same or they may be different.

FIG. 1 shows one embodiment of a targeted T-cell engaging agent construct comprising (a) an scFv targeting domain comprising a VH domain and a VL domain that bind the target, wherein the VH and VL domain are connected by a flexible linker; (b) an inactive T-cell engaging domain comprising a VL domain that binds to an inert VH domain, wherein the VH and VL domains are connected by a flexible linker having a cleavage site, and (c) a flexible linker joining the targeting domain and the inactive T-cell engaging domain.

Figure 2:
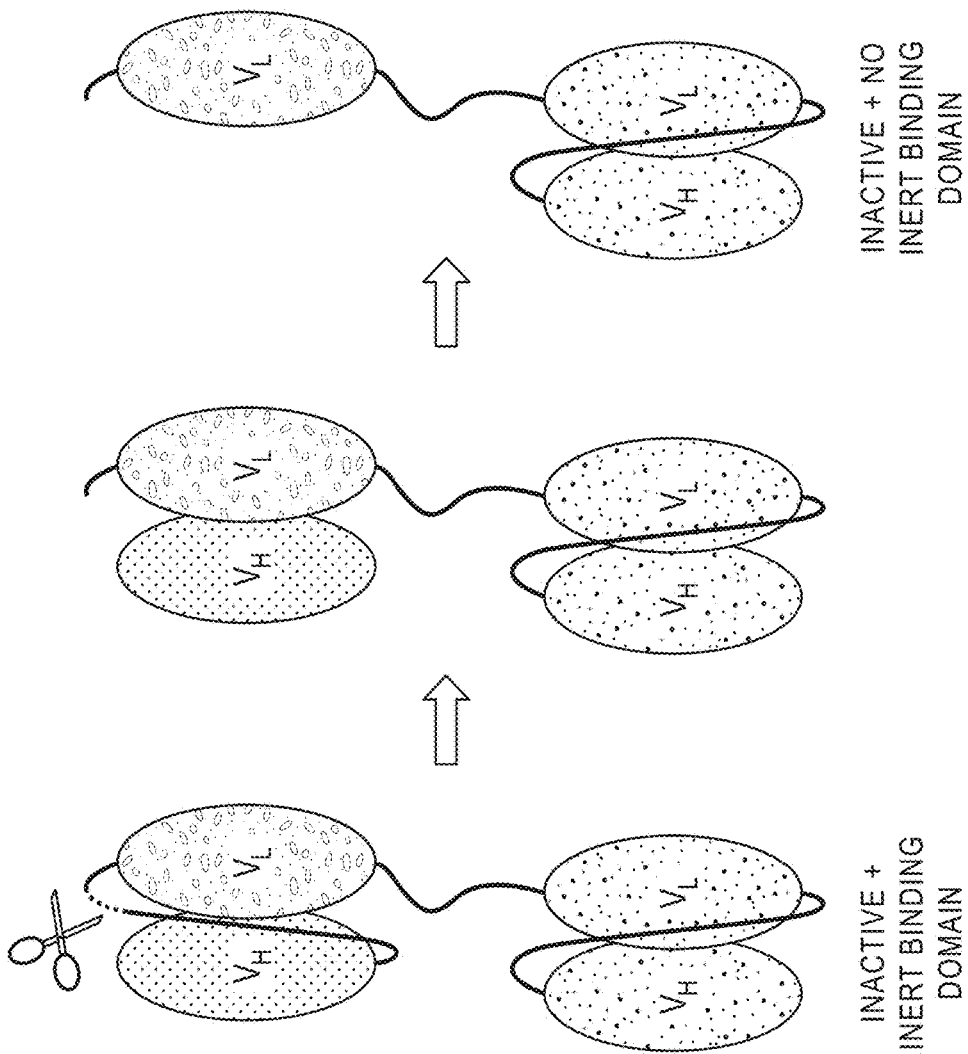
FIG. 2 shows the process by which the cleavable linker is cleaved and the inert binding partner is released to create an active entity.

In some embodiments, FIG. 2 shows the process by which the cleavable linker is cleaved and the inert binding partner is released to create an entity without an inert binding partner. This entity is still inactive because the VL domain in the T-cell engaging domain is not active on its own.

Figure 3:
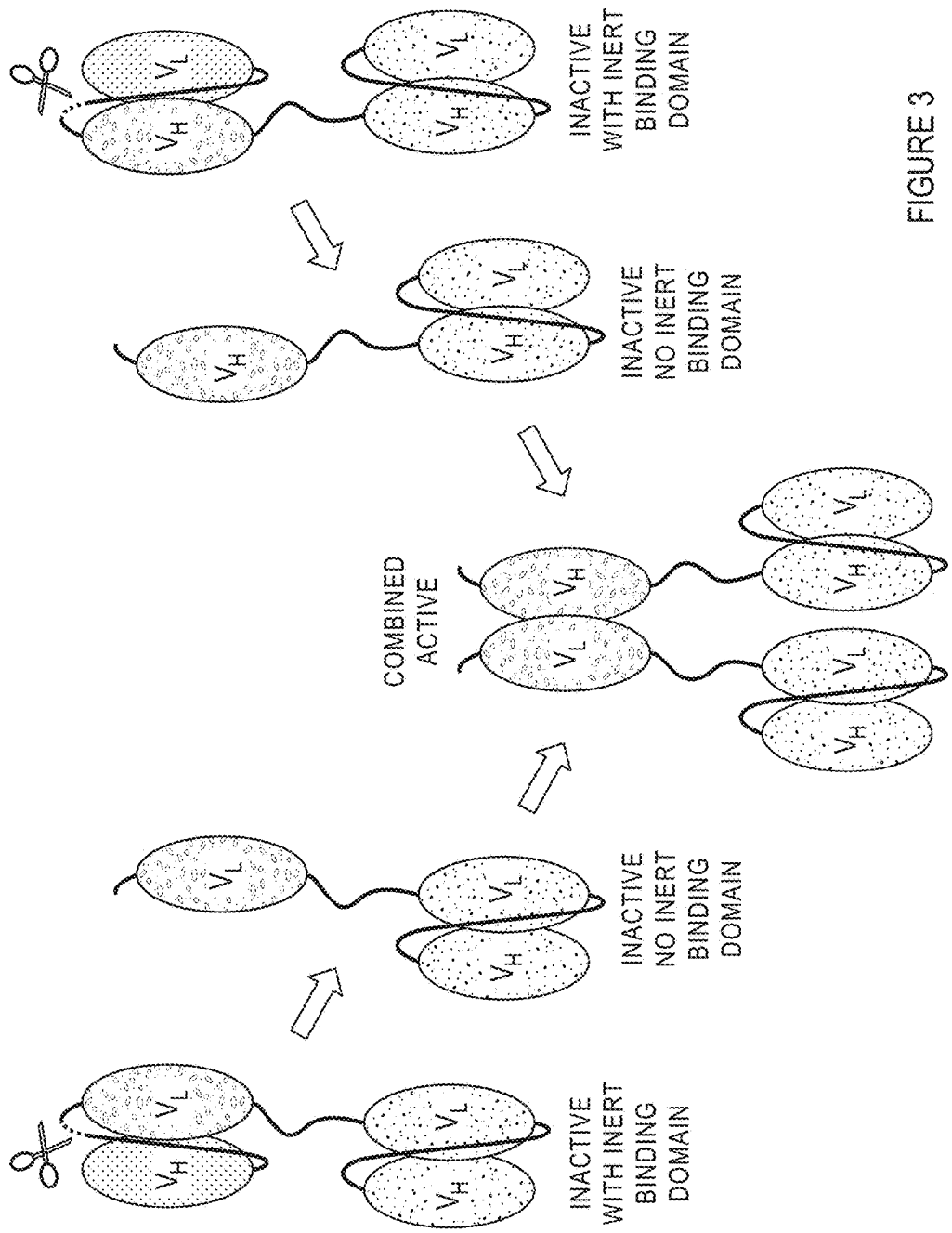
FIG. 3 illustrates the creation of an active targeted, T-cell engaging agent after the inert binding partner is released from a pair of complementary components in a two-component system.

In some embodiments, FIG. 3 illustrates the creation of an active targeted T-cell engaging agent after the inert binding partner is released from a pair of complementary targeted T-cell engaging agents.

Figure 4B:
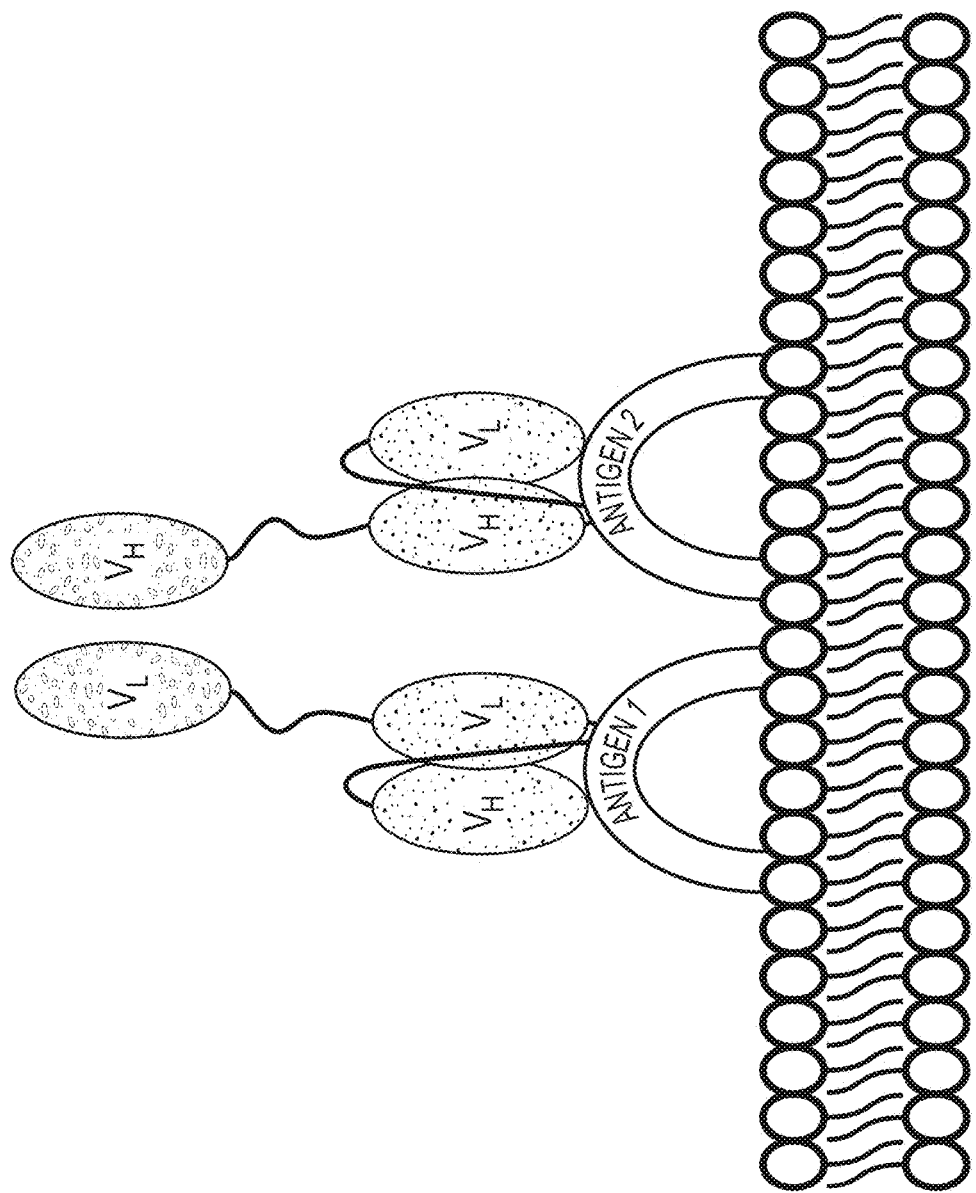
Figure 4C:
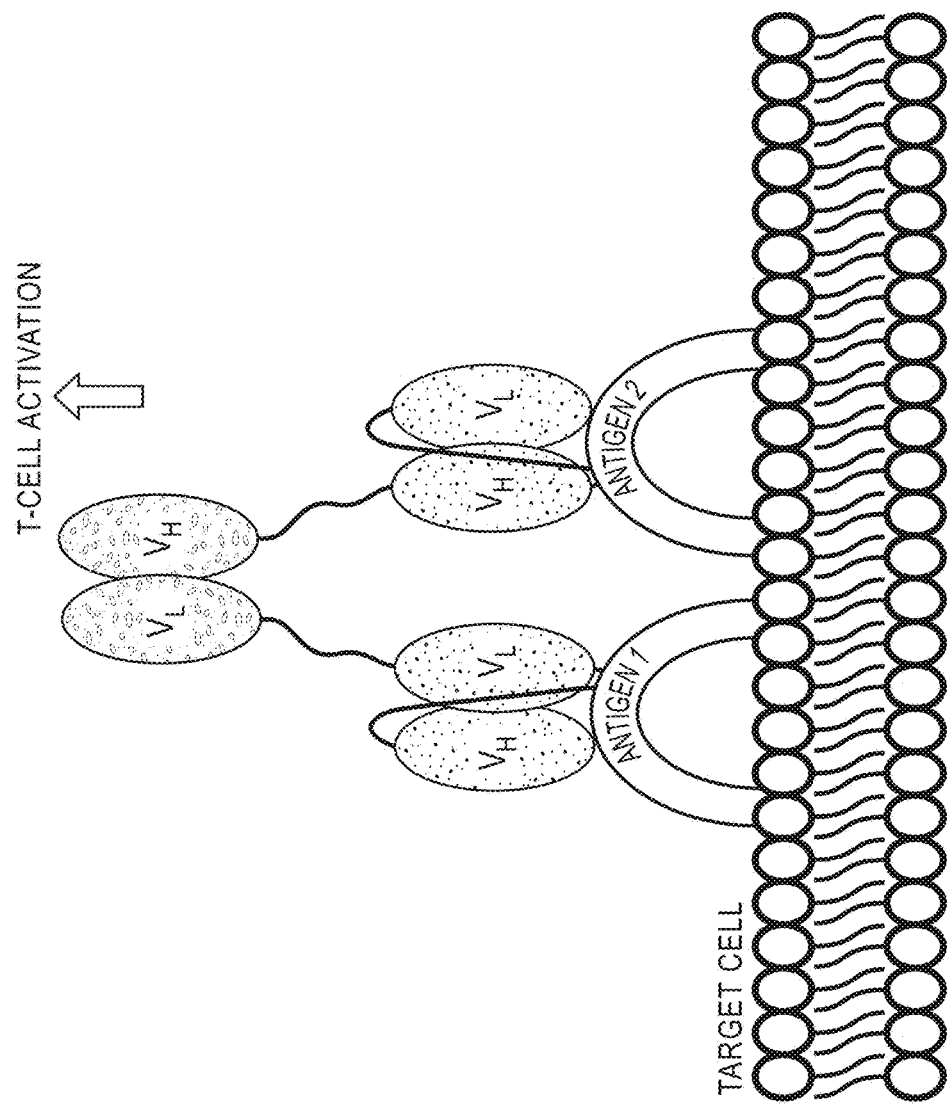

In some embodiments, FIGS. 4A-C illustrate the cleavage of the stepwise process of the targeted T-cell engaging agents binding to the target cell (4A), cleavage of the inert binding partners (4A and 4B), and binding to create an active targeted T-cell engaging agent (4C).

In some alternative embodiments, the second T-cell engaging domain may not be bound to a targeting moiety and/or may not comprise a cleavage site and inert binding partner. In some instances, the second T-cell engaging domain may be conjugated or linked to a targeting moiety (either the same targeting moiety or a different targeting moiety), but in such an embodiment it would not be conjugated or linked to an inert binding partner. In such an embodiment, only the first T-cell engaging domain is bound to an inert binding partner. In another embodiment, the second T-cell engaging domain may also comprise a targeting moiety, a cleavage site, and an inert binding partner, each as described herein.

In some embodiments, the structural arrangement from N-terminus to C-terminus of the first component comprises IBVL-L1-TCEVH-L2-TVL-L3-TVH. In some embodiments, the structural arrangement from N-terminus to C-terminus of the second component comprises TCEVL-L2-TVH-L3-TVL. In some embodiments, the structural arrangement from N-terminus to C-terminus of the second component comprises IBVH-L1-TCEVL-L2-TBVH-L3-TBVL. In each of these embodiments IB stands for inert binding partner and IBVL is a VL inert binding partner, whereas IBVH is a VH insert binding domain. TCE stands for T-cell engaging and an TCEVL is a VL portion of a T-cell engaging domain and a TCEVH is a VH portion of a T-cell engaging domain. TB stand for target binding domain and a TBVH is a VH portion of a target binding domain and a TBVL is a VL portion of a target binding domain. L1 is a linker with a protease cleavage site, while L2 and L3 are optionally linkers that optionally are not cleavable by the same protease as L1.

A. Targeting Moiety

The targeting moiety functions in the targeted T-cell engaging agent by delivering the agent to the local environment of the unwanted cells, enabling a localized treatment strategy. In certain embodiments, the targeting moiety targets the unwanted cells by specifically binding to the unwanted cells. In some instances, the targeting moiety specifically binds the unwanted cells even while the inert binding partner is binding the first T-cell engaging domain.

In some embodiments, a first targeting moiety is bound, optionally by a linker, to a first T-cell engaging domain and, as part of a separate construct, a second targeting moiety is bound, optionally by a linker, to a second T-cell engaging domain. In this way, each complementary part of the T-cell engaging domain is delivered to the unwanted cells by a separate targeting moiety. In some embodiments, the targeting moieties are of the same type and, in some embodiments, the targeting moieties are different. When the targeting moieties are of different types, they can either target different epitopes (either overlapping or nonoverlapping) on the same target protein of the unwanted cell or they can target different target proteins. In situations when the targeting moieties target different proteins, the unwanted cell will express an antigen corresponding to each of the two types of targeting moieties, providing additional specificity for this approach.

In certain embodiments, the targeting moiety is an antibody or functional part thereof. By functional part, we mean any antibody fragment that retains its binding activity to the target on the unwanted cell, such as an scFv or VHH or other functional fragment including an immunoglobulin devoid of light chains, Fab, Fab', F(ab')$_2$, Fv, antibody fragment, diabody, scAB, single-domain heavy chain antibody, single-domain light chain antibody, Fd, CDR regions, or any portion or peptide sequence of the antibody that is capable of binding antigen or epitope. Unless specifically noted as "full length antibody," when the application refers to antibody it inherently includes a reference to a functional part thereof.

Certain antibody targets (with examples of unwanted cell types in parentheses) may include: Her2/Neu (Epithelial malignancies); CD22 (B cells, autoimmune or malignant); EpCAM (CD326) (Epithelial malignancies); EGFR (epithelial malignancies); PMSA (Prostate Carcinoma); CD30 (B cell malignancies); CD20 (B cells, autoimmune, allergic or malignant); CD33 (Myeloid malignancies); membrane 1gE (Allergic B cells); 1gE Receptor (CD23) (Mast cells or B cells in allergic disease), CD80 (B cells, autoimmune, allergic or malignant); CD86 (B cells, autoimmune, allergic or malignant); CD2 (T cell or NK cell lymphomas); CA125 (multiple cancers including Ovarian carcinoma); Carbonic Anhydrase IX (multiple cancers including Renal Cell Carcinoma); CD70 (B cells, autoimmune, allergic or malignant); CD74 (B cells, autoimmune, allergic or malignant); CD56 (T cell or NK cell lymphomas); CD40 (B cells, autoimmune, allergic or malignant); CD19 (B cells, autoimmune, allergic or malignant); c-met/HGFR (Gastrointestinal tract and hepatic malignancies; TRAIL-R1 (multiple malignancies including ovarian and colorectal carcinoma); DR5 (multiple malignancies including ovarian and colorectal carcinoma); PD-1 (B cells, autoimmune, allergic or malignant); PD1L (Multiple malignancies including epithelial adenocarcinoma); IGF-1R (Most malignancies including epithelial adenocarcinoma); VEGF-R2 (The vasculature associated with the majority of malignancies including epithelial adenocarcinomas; Prostate stem cell antigen (PSCA) (Prostate Adenocarcinoma); MUC1 (Epithelial malignancies); CanAg (tumors such as carcinomas of the colon and pancreas); Mesothelin (many tumors including mesothelioma and ovarian and pancreatic adenocarcinoma); P-cadherin (Epithelial malignancies, including breast adenocarcinoma); Myostatin (GDF8) (many tumors including sarcoma and ovarian and pancreatic adenocarcinoma); Cripto (TDGF1) (Epithelial malignancies including colon, breast, lung, ovarian, and pancreatic cancers); ACVRL 1/ALK1 (multiple malignancies including leukemias and lymphomas); MUC5AC (Epithelial malignancies, including breast adenocarcinoma); CEACAM (Epithelial malignancies, including breast adenocarcinoma); CD137 (B cells or T cells, autoimmune, allergic or malignant); CXCR4 (B cells or T cells, autoimmune, allergic or malignant); Neuropilin 1 (Epithelial malignancies, including lung cancer); Glypicans (multiple cancers including liver, brain and breast cancers); HER3/EGFR (Epithelial malignancies); PDGFRa (Epithelial malignancies); EphA2 (multiple cancers including neuroblastoma, melanoma, breast cancer, and small cell lung carcinoma); CD38 (Myeloma); CD138 (Myeloma); α4-integrin (AML, myeloma, CLL, and most lymphomas).

In certain modes, antibodies include an anti-epidermal growth factor receptor antibody such as Cetuximab, an anti-Her2 antibody, an anti-CD20 antibody such as Rituximab, an anti-CD22 antibody such as Inotuzumab, G544 or BU59, an anti-CD70 antibody, an anti-CD33 antibody such as hp67.6 or Gemtuzumab, an anti-MUC1 antibody such as GP1.4 and SM3, an anti-CD40 antibody, an anti-CD74 antibody, an anti-P-cadherin antibody, an anti-EpCAM antibody, an anti-CD138 antibody, an anti-E-cadherin antibody, an (anti-CEA antibody, an anti-FGFR3 antibody, and an anti α4-integrin antibody such as natalizumab.

Table 2A provides nonlimiting examples of cancer types, possible targeting moieties, and proteases that are expressed by those cancer types. In order to prepare a two-component system, the cancer may be identified from column 1, one or two targets chosen for the targeting moiety (as desired), and one or two proteases chosen for the cancer type, as well (as desired). Other sections of this application discuss when to use one versus two targeting moieties and one versus two protease cleavage sites.

TABLE 2A

Coordination of Cancer Type, Targets for Targeting Moiety, and Proteases that Can Cleave Cleavage Sites

| Cancer | Targets for Targeting Moiety | Proteases that can Cleave Cleavage Site |
|---|---|---|
| Prostate Cancer | ADAM17, CD59, EpCAM, HER2, Integrin αV, Integrin αVβ3, MCP-1, PCLA, PSCA, PSMA, RANKL, RG1, SLC44A4 STEAP-1, VEGF-C | KLK3 (PSA), KLK4, ADAM17, Cathepsin B, uPA, uPAR, HPN, ST14, TMPRSS2 |
| Breast Cancer | CA125, CCN1, CD44, CD98, c-RET, DLL4, EpCAM, Episialin, GPNMB, HER2/neu, HER3, IGF-1R, Integrin α6β4, LFL2, LIV-1, Ly6E, MUC1, MUC18, NRP1, Phosphatidylserine, PRLR, TACSTD-2, Tenascin C, TWEAKR, VANGL2, PD-L1, PD-L2 | MMP2, MMP9, Cathepsin L, Cathepsin K, Cathepsin B, MMP11, HPN, ST14, ADAM28 |
| Myeloma | BCMA, IGF-1R, DKK-1, ICAM-1, CD138/Syndecan1, CD38, GRP78, FGFR3, SLAMF6, CD48, TfR(CD71) APRIL, CD40, CD19, DR5, CXCR4 | MMP2, MMP9, MMP1, MMP7, TMPRSS2, PRSS22, KLK11 |
| B-cell Lymphoma | CD20, CD22, CD19, CD37, CD70, HLA-DR, CD70b | ADAM28, Cathepsin B, MMP9 |
| Renal Cell carcinoma | PD-L, PD-L2, CAIX, TPBG, CD70, ENPP3, FGFR1 | ST14, MMP9 |
| Gastric Carcinoma | VEGFR-2, CLDN18, GCC, C242, HER2/neu, FGFR2, EpCAM, GPR49, HER3, IGFR | MMP2, MMP9, Cathepsin B, uPA, uPAR |
| Glioblastoma | HER2/neu, EGFR, ALK, EphA2, GD2, EGFRvIII, ALK | MMP2, MMP9, |
| T-cell lymphoma | CD2, CD4, CD5, CD71, CD30 | Cathepsin B, Cathepsin D, MMP9 |
| Hodgkin Lymphoma | CD30, CD40, IL-3Ra, CD30 | Cathepsin B |
| Lung Cancer | EGFR, IGF-1R, HER3, Integrin α5β1, Lewis y/b antigen, EGFL7, TPBG, DKK-1, NaPi2b, flt4, cMet, CD71 | Cathepsin B, MMP2, MMP9, ST14, ADAM17 |
| Pancreatic Carcinoma | SLC44A4, uPAR, MUC1, MUCH16, TACSTD-2, CEA, EphhA4, mesothelin, EGFR, MUC13, MU5AC, AGF-1R, HER3, CD71 | Cathepsin B, ST14, ADAM28 |
| Head and Neck cancer | EGFR, EpCAM, HER2 | Cathepsin B, ST14, ADAM17 |
| Acute myeloid leukemia | CD33, CD133, CD123, CD45, CD98, c-Kit, Lewis Y, Siglec-15, FLT-3 | ADAM17, Cathepsin B, uPA, uPAR |
| Melanoma | MUC18, CD40, GD2, CEACAM1, Cadherin-19, GM3, Integrin α5β1, TYRP1, GD3, Integrin αV | Cathepsin B, MMP9 |
| Ovarian Cancer | HER2/neu, EpCAM, CA125, DLL4, Integrin αVβ3, MUC5A, NaPi2B, Mesothelin, CLDN6 | Cathepsin B, MMP2, MMP9 |
| Liver Cancer | Glypican-3, FGFR4, ENPP3, PIVKA-II, PLVAP, cMet, EpCAM | Cathepsin B, MMP9 |

TABLE 2A-continued

Coordination of Cancer Type, Targets for Targeting Moiety, and Proteases that Can Cleave Cleavage Sites

| Cancer | Targets for Targeting Moiety | Proteases that can Cleave Cleavage Site |
| --- | --- | --- |
| Colorectal Carcinoma | EGFR, Lewis y/b, Progastrin, GPR49, CEA, CLDN1, A33, CK8, Integrin αV, EpCAM, DLL4, EGFL7, FAP, | Cathepsin S, Cathepsin L, Cathepsin B, uPA, uPAR, MMP2, MMP9, ST14 |

For example, when targeting moieties in the first and second components are different, Table 2B provides a non-limiting list of potential targeting moieties to use in combination with particular cancer types. In a two-component system, a targeting moiety for the first component would be present and a second targeting moiety for the second component may optionally be present. If only the first component has a targeting moiety or if the first and second components have the same targeting moiety, either the targeting moiety listed in column 1 or column 2 of the table may be used when the cancer type is listed in column 3.

TABLE 2B

Targeting Moieties for Use in Two-Component System

| Targeting Moiety for First Component | Optional Targeting Moiety for Second Component | Cancer Type |
| --- | --- | --- |
| Antibody against CD20 (such as Rituximab) | Antibody against CD80 | Lymphoma |
| Antibody against CD20 (such as Rituximab) | Antibody against CD22 (such as Inotuzumab) | Lymphoma |
| Antibody against CD20 (such as Rituximab) | Antibody against CD70 | Lymphoma |
| Antibody against HER2 | Antibody against EpCAM | Epithelial malignancies |
| Antibody against EGFR (such as Cetuximab) | Antibody against mucin protein core | Breast cancer |
| Antibody against EGFR (such as Cetuximab) | Antibody against HER2 | Epithelial malignancies |
| Antibody against EGFR (such as Cetuximab) | Antibody against transferrin receptor | Gliomas |
| Antibody against gp95/gp97 | Antibody against p-glycoprotein | Drug-resistant melanomas |
| Antibody against TRAIL-R1 | Antibody against DR5 | Multiple malignancies, including ovarian and colorectal carcinoma |
| Antibody against IL-4 | Antibody against IL-6 | Lymphomas and leukemias |
| Antibody against CD19 | Antibody against CD22 | Lymphoma |
| Antibody against PMSA | Antibody against PSCA | Prostate carcinoma |
| Antibody against P-cadherin | Antibody against Cripto (TDGF1) | Epithelial malignancies |
| Antibody against CD74 | Antibody against CD40 | Lymphomas |
| Antibody against PD1L | Antibody against IGF-1R | Epithelial adenocarcinoma |
| Antibody against CD38 | Antibody against CD138 | Myeloma |
| Antibody against BCMA | Antibody against CD138 or CD38 | Myeloma |
| Antibody against CD33 | Antibody against CD133 | Myeloid Malignancies, e.g. AML |
| Antibody against CD33 | Antibody against CD123 | Myeloid Malignancies such as AML |
| Antibody against CD49d | Antibody against CD33 | Myeloid Malignancies |
| Antibody against PSMA | Antibody against PSCA | Prostate Cancer |
| Antibody against Glypican 3 | Antibody against cMet or EpCAM | Hepatocellular carcinoma |
| Antibody against EpCAM | Antibody against EGFR | Lung Cancer |
| Antibody against EpCAM | Antibody against MUC1 | Pancreatic Cancer |
| Antibody against EpCAM | Antibody against EGFR | Colorectal Carcinoma |
| Antibody against MUC1 | Antibody against EGFR | Ovarian Carcinoma |
| Antibody against GD2 | Antibody against HER2 | Sarcoma |
| Antibody against HER2 | Antibody against HER3 | Breast Cancer |
| Antibody against IL-13R | Antibody against EGFR | Brain Cancer |

In some embodiments, the targeting moiety is not an antibody, but is another type of targeting moiety. For example, a targeting moiety may be a binding partner for a protein known to be expressed on the unwanted cell. Such expression levels may include overexpression. For example, the following binding partners may bind to the following targets on an unwanted cell:

TABLE 3

Non-Antibody Binding Partners and Corresponding Targets

| Binding Partner | Target on Unwanted Cell |
|---|---|
| IL-2 | IL-2 receptor |
| IL-4 | IL-4 receptor |
| IL-6 | IL-6 receptor |
| α-MSH | MSH receptor (melanocyte stimulating hormone receptor) |
| Transferrin | TR (transferrin receptor) |
| Folic acid | FOLR (folate receptor 1) and/or FOLH1 (folate hydroxylase) |
| EGF and/or TGFα | EGFR (EGF receptor) |
| PD1 | PD-L1 and/or PD-L2 |
| IL13 | IL-13R (Glioblastoma) |
| Stem cell factor | CXCR4 |
| Insulin-like growth factor (IGF) | IGFR |
| CD40 | CD40L |

The binding partner need not comprise the full length or wildtype sequence for the binding partners listed in Table 3. All that is required is that the binding partner bind to the target on the unwanted cell and can thus include truncated forms, analogs, variants, and derivatives that are well known in the art.

Additionally, in some embodiments, the binding partner may be an aptamer that is capable of binding to a protein known to be expressed on the unwanted cell. Aptamers that bind unwanted cells, such as cancer cells, are well known and methods for designing them are known.

Cell-based SELEX systems may be used to select a panel of target cell-specific aptamers from a random candidate library. A ssDNA pool may be dissolved in binding buffer and denatured and then incubated with target cells. After washing the bound DNAs may be eluted by heating and then incubated with negative cells (if desired), centrifuged, and the supernatant removed. The supernatant may be amplified by PCR with biotin labeled primers. The selected sense ssDNA may be separated from the antisense biotinylated strand using streptavidin coated beads. To increase affinity, washing strength may be increased through increasing washing time, volume of buffer, and number of washes. After the desired rounds of selection, the selected ssDNA pool may be PCR amplified and cloned into *E. coli* and sequenced. See Shangguan et al., Aptamers evolved from live cells as effective molecular probes for cancer study, PNAS 103(32): 11838-11843 (2006); Lyu et al, Generating Cell Targeting Aptamers for Nanotherapeutics Using Cell-SELEX, Theranostics 6(9):1440-1452 (2016); see also Li et al., Inhibition of Cell Proliferation by an Anti-EGFR Aptamer, PLoS One 6(6):e20229 (2011). The specific approaches for designing aptamers and specific aptamers binding to cancer cells in these references are hereby incorporated by reference.

For example, an aptamer may comprise SEQ ID NO: 94 to 164. In some embodiments, an aptamer may comprise SEQ ID NO: 95. These aptamers are directed to EGFR and are provided only as representative of the aptamers that can bind to targets presented on unwanted cells. Other aptamers against other targets on unwanted cells are equally part of the description herein and incorporated by reference as described in Zhu et al., Progress in Aptamer Mediated Drug Delivery Vehicles for Cancer Targeting, Theranostics 4(9): 931-944 (2014).

In some embodiments, aptamers for use herein bind to the target on the unwanted cell with a $K_d$ in the nanomolar to picomolar range (such as 1 picomolar to 500 nanomolar or 1 picomolar to 100 nanomolar).

B. T-Cell Engaging Domain

The targeted T-cell engaging agent comprises a first T-cell engaging domain that is unable of engaging a T-cell alone. Instead, the first T-cell engaging domain is capable of activity when binding a second T-cell engaging domain, which is not part of the targeted T-cell engaging agent. Thus, the first and second T-cell engaging domains may be any two moieties that do not possess T-cell engaging activity alone, but do possess it when paired with each other. In other words, the first and second T-cell engaging domains are complementary halves of a functional active protein.

When the two T-cell engaging domains are associated together in the two-component system, they may bind to the CD3 antigen and/or T-cell receptor on the surface of the T-cell as these activate T cells. CD3 is present on all T cells and consists of subunits designated γ, δ, ε, ζ, and η. The cytoplasmic tail of CD3 is sufficient to transduce the signals necessary for T cell activation in the absence of the other components of the TCR receptor complex. Normally, activation of T cell cytotoxicity depends first on binding of the TCR with a major histocompatibility complex (MHC) protein, itself bound to a foreign antigen, located on a separate cell. In a normal situation, only when this initial TCR-MHC binding has taken place can the CD3 dependent signally cascade responsible for T cell clonal expansion and, ultimately, T cell cytotoxicity ensue. In some of the present embodiments, however, when the two-component system binds to CD3 and/or the TCR, activation of cytotoxic T cells in the absence of independent TCR-MHC can take place by virtue of the crosslinking of the CD3 and/or TCR molecules mimicking an immune synapse formation. This means that T cells may be cytotoxically activated in a clonally independent fashion, i.e. in a manner that is independent of the specific TCR clone carried by the T cell. This allows for activation of the entire T cell compartment rather than only specific T cells of a certain clonal identity.

In some embodiments, the first T-cell engaging domain is a VH domain and the second T-cell engaging domain is a VL domain. In other embodiments, the first T-cell engaging domain is a VL domain and the second T-cell engaging domain is a VH domain. In such embodiments, when paired together the first and second T-cell engaging domains may comprise an scFv.

If the first and second T-cell engaging domains are a pair of VH and VL domains, the VH and VL domains may be specific for an antigen expressed on the surface of a T cell, such as CD3 or TCR. If the antigen is CD3, one potential T-cell engaging domain may be derived from muromonab.

C. Inert Binding Partner

The targeted T-cell engaging agent also comprises at least one inert binding partner capable of binding the first T-cell engaging domain and preventing it from binding to a second T-cell engaging domain unless certain conditions occur. When the first T-cell engaging domain is bound to the at least one inert binding partner, it does not possess a T-cell engaging activity. In other words, the at least one inert binding partner cripples the function of the first T-cell engaging domain by blocking it from binding its complementary pair (the second T-cell engaging domain) and preventing the two domains from joining together to have a T-cell engaging activity. In other words, the inert binding partner binds to the first T-cell engaging domain such that the first T-cell engaging domain does not bind to the second T-cell engaging domain unless the inert binding partner is removed. By does not bind, the application does not exclude nonspecific binding or low levels of binding (for example, ≤1%, ≤5%, ≤10%).

In some embodiments, the inert binding partner binds specifically to the T-cell engaging domain.

In some embodiments, the at least one inert binding partner is a VH or VL domain. In some embodiments, when the T-cell engaging domain in the targeted T-cell engaging agent is a VH domain, the inert binding partner may be a VL domain and when the first T-cell engaging domain is a VL domain, the inert binding partner may be a VH domain.

If a first component comprises a targeting moiety and a VL T-cell engaging domain and a VH inert binding partner, in some embodiments, the VH inert binding partner has an equilibrium dissociation constant for binding to the VL T-cell engaging domain, which is greater than the equilibrium dissociation constant of the VL T-cell engaging domain for its partner VH T-cell engaging domain in the second component. In some embodiments, the prior sentence is equally true when VH is switched for VL and vice versa.

Based on empirical evidence in the examples, it is believed that using the inert binding partner as a mispairing partner with the T-cell engaging domain in the construct results in constructs that are more stable and easier to manufacture.

D. Cleavage Site

By way of overview, the cleavage site may be (i) cleaved by an enzyme expressed by the unwanted cells; (ii) cleaved through a pH-sensitive cleavage reaction inside the unwanted cell; (iii) cleaved by a complement-dependent cleavage reaction; or (iv) cleaved by a protease that is colocalized to the unwanted cell by a targeting moiety that is the same or different from the targeting moiety in the agent. In some embodiments, the cleavage site is a protease cleavage site.

The cleavage sites function to release the inert binding partner from the first T-cell engaging domain. The cleavage sites can function in different ways to release the inert binding partner from the first T-cell engaging domain T-cell epitopes in the microenvironment of the unwanted cells. The cleavage may occur inside the unwanted cell or outside the unwanted cell, depending on the strategy employed. If cleavage occurs outside the unwanted cell, the T-cell engaging domain can be presented without first being internalized into a cell and being engaged in the classical antigen-processing pathways.

In certain embodiments, at least one cleavage site may be cleaved by an enzyme expressed by the unwanted cells. Cancer cells, for instance, are known to express certain enzymes, such as proteases, and these may be employed in this strategy to cleave the targeted T-cell engaging agent's cleavage site. By way of nonlimiting example, cathepsin B cleaves FR, FK, VA and VR amongst others; cathepsin D cleaves PRSFFRLGK (SEQ ID NO: 42), ADAM28 cleaves KPAKFFRL (SEQ ID NO: 1), DPAKFFRL (SEQ ID NO: 2), KPMKFFRL (SEQ ID NO: 3) and LPAKFFRL (SEQ ID NO: 4); and MMP2 cleaves AIPVSLR (SEQ ID NO: 46), SLPLGLWAPNFN (SEQ ID NO: 47), HPVGLLAR (SEQ ID NO: 48), GPLGVRGK (SEQ ID NO: 49), and GPLGL-WAQ (SEQ ID NO: 50), for example. Other cleavage sites listed in Table 1A or 2A may also be employed. Protease cleavage sites and proteases associated with cancer are well known in the art. Oncomine (www.oncomine.org) is an online cancer gene expression database, so when the agent of the invention is for treating cancer, the skilled person may search the Oncomine database to identify a particular protease cleavage site (or two protease cleavage sites) that will be appropriate for treating a given cancer type. Alternative databases include the European Bioinformatic Institute (www.ebi.ac.uk), in particular (www.ebi.ac.uk/gxa). Protease databases include PMAP (www.proteolysis.org), ExPASy Peptide Cutter (ca.expasy.org/tools/peptidecutter) and PMAP.Cut DB (cutdb.burnham.org).

In some embodiments, at least one cleavage site may be cleaved through a pH-sensitive cleavage reaction inside the unwanted cell. If the targeted T-cell engaging agent is internalized into the cell, the cleavage reaction may occur inside the cell and may be triggered by a change in pH between the microenvironment outside the unwanted cell and the interior of the cell. Specifically, some cancer types are known to have acidic environments in the interior of the cancer cells. Such an approach may be employed when the interior unwanted cell type has a characteristically different pH from the extracellular microenvironment, such as particularly the glycocalyx. Because pH cleavage can occur in all cells in the lysozymes, selection of a targeting agent when using a pH-sensitive cleavage site may require, when desired, more specificity. For example, when a pH-sensitive cleavage site is used, a targeting agent that binds only or highly preferably to cancer cells may be desired (such as, for example, an antibody binding to mesothelin for treatment of lung cancer).

In certain embodiments, at least one cleavage site may be cleaved by a complement-dependent cleavage reaction. Once targeted T-cell engaging agents bind to the unwanted cell, the patient's complement cascade may be triggered. In such a case, the complement cascade may also be used to cleave the inert binding partner from the first T-cell engaging domain by using a cleavage site sensitive to a complement protease. For example, C1r and C1s and the C3 convertases (C4B, 2a and C3b,Bb) are serine proteases. C3/C5 and C5 are also complement proteases. Mannose-associated binding proteins (MASP), serine proteases also involved in the complement cascade and responsible for cleaving C4 and C2 into C4b2b (a C3 convertase) may also be used. For example, and without limitation, C1s cleaves YLGRSYKV (SEQ ID NO: 73) and MQLGRX (SEQ ID NO: 74). MASP2 is believed to cleave SLGRKIQI (SEQ ID NO: 75). Complement component C2a and complement factor Bb are believed to cleave GLARSNLDE (SEQ ID NO: 76).

In some embodiments, at least one cleavage site may be cleaved by a protease that is colocalized to the unwanted cell by a targeting moiety that is the same or different from the targeting moiety in the targeted T-cell engaging agent. For example, any protease may be simultaneously directed to the microenvironment of the unwanted cells by conjugating the protease to a targeting agent that delivers the protease to that location. The targeting agent may be any targeting agent described herein. The protease may be affixed to the targeting agent through a peptide or chemical linker and may maintain sufficient enzymatic activity when bound to the targeting agent.

In some embodiments, both the first component and second component are mispaired with an inert binding partner. In some embodiments, the protease cleavage site in the first component and the second component are the same. In other embodiments, the protease cleavage sites in the first component and the second component are different cleavage sites for the same protease. In other embodiments, the protease cleavage sites in the first component and the second component are cleavage sites for different proteases. In some embodiments employing two different proteases, the unwanted cell expresses both proteases.

In some embodiments, in a first component, the inert binding partner in an uncleaved state interferes with the specific binding of a VL or VH T-cell engaging domain to its partner VH or VL, respectively, T-cell engaging domain in a second component. In some embodiments, the inert binding partner in an uncleaved state inhibits the binding of the VL or VH T-cell engaging domain to its partner VH or VL, respectively, T-cell engaging domain in a second component such that the dissociation constant (Kd) of the VL or VH T-cell engaging domain to its partner VH or VL, respectively, T-cell engaging domain in a second component in an uncleaved state is at least 100 times greater than the Kd of the VL or VH T-cell engaging domain to its partner VH or VL, respectively, T-cell engaging domain in a second component in a cleaved state.

E. Linkers

In addition to the cleavage site, linkers may optionally be used to attach the separate parts of the targeted T-cell engaging agents together. By linker, we include any chemical moiety that attaches these parts together. In some embodiments, the linkers may be flexible linkers. Linkers include peptides, polymers, nucleotides, nucleic acids, polysaccharides, and lipid organic species (such as polyethylene glycol). In some embodiments, the linker is a peptide linker. Peptide linkers may be from about 2-100, 10-50, or 15-30 amino acids long. In some embodiments, peptide linkers may be at least 10, at least 15, or at least 20 amino acids long and no more than 80, no more than 90, or no more than 100 amino acids long. In some embodiments, the linker is a peptide linker that has a single or repeating GGGGS (SEQ ID NO: 85), GGGS (SEQ ID NO: 86), GS (SEQ ID NO: 87), GSGGS (SEQ ID NO: 88), GGSG (SEQ ID NO: 89), GGSGG (SEQ ID NO: 90), GSGSG (SEQ ID NO: 91), GSGGG (SEQ ID NO: 92), GGGSG (SEQ ID NO: 93), and/or GSSSG (SEQ ID NO: 94) sequence(s).

In some embodiments, the linker is a maleimide (MPA) or SMCC linker.

F. Methods of Making

The targeted T-cell engaging agents as described herein can be made using genetic engineering techniques. Specifically, a nucleic acid may be expressed in a suitable host to produce a targeted T-cell engaging agent. For example, a vector may be prepared comprising a nucleic acid sequence that encodes the targeted T-cell engaging agent including all of its component parts and linkers and that vector may be used to transform an appropriate host cell.

Various regulatory elements may be used in the vector as well, depending on the nature of the host and the manner of introduction of the nucleic acid into the host, and whether episomal maintenance or integration is desired.

Chemical linkage techniques, such as using maleimide or SMCC linkers, may also be employed.

In instances where the binding partner is an aptamer, a person of ordinary skill in the art would appreciate how to conjugate an aptamer to a protein, namely the T-cell engaging domain. Aptamers may be conjugated using a thiol linkage or other standard conjugation chemistries. A maleimide, succinimide, or SH group may be affixed to the aptamer to attach it to the T-cell engaging domain.

II. Pharmaceutical Compositions

The targeted T-cell engaging agents may be employed as pharmaceutical compositions. As such, they may be prepared along with a pharmaceutically acceptable carrier. If parenteral administration is desired, for instance, the targeted T-cell engaging agents may be provided in sterile, pyrogen-free water for injection or sterile, pyrogen-free saline. Alternatively, the targeted T-cell engaging agents may be provided in lyophilized form for resuspension with the addition of a sterile liquid carrier.

III. Methods of Treatment

A. Reduction of Unwanted Cells, Targeting of Immune Response, and Treatment of Cancer The targeted T-cell engaging agents described herein may be used in a method of treating a disease in a patient characterized by the presence of unwanted cells comprising administering a two-component system comprising at least one targeted T-cell engaging agent and a second component to the patient, as each of the components have been described in detail in various embodiments above. Additionally, the agents described herein may also be used in a method of targeting a patient's own immune response to unwanted cells comprising administering a two-component system to the patient.

The amount of the agent administered to the patient may be chosen by the patient's physician so as to provide an effective amount to treat the condition in question. The first component and the second component of the two-component system may be administered in the same formulation or two different formulations within a sufficiently close period of time to be active in the patient.

The patient receiving treatment may be a human. The patient may be a primate or any mammal. Alternatively, the patient may be an animal, such as a domesticated animal (for example, a dog or cat), a laboratory animal (for example, a laboratory rodent, such as a mouse, rat, or rabbit), or an animal important in agriculture (such as horses, cattle, sheep, or goats).

The condition characterized by unwanted cells may include cancer. The cancer may be a solid or non-solid malignancy. The cancer may be a solid tumor wherein the solid tumor is not a lymphoma. The cancer may be any cancer such as breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease and premalignant disease.

The two-component system may be administered alone or in conjunction with other forms of therapy, including surgery, radiation, or traditional chemotherapy.

EXAMPLES

Example 1. Preparation of Constructs

Various constructs, both control and experimental, were prepared and used in the examples.

A. Single Chain scFv Bispecific Constructs

A single chain scFv construct was used in this application in order to serve as a positive control. Construct 6245 (SEQ ID NO: 165) was prepared as a bispecific antibody comprising an anti-EPCAM scFv and anti-CD3E scFv. This construct does not comprise any mispairing with an inert binding partner and has both active targeting and T-cell engaging moieties.

B. Precleaved Two-Component System Constructs Using a Targeting scFv

Construct 6246 (SEQ ID NO: 166) and 6247 (SEQ ID NO: 167) are complementary precleaved constructs in a two-component system. By precleaved, the description refers to a construct with a functional targeting moiety and an unpaired T-cell engaging moiety (i.e., one that is not mispaired to an inert binding partner and one that is also not yet paired with its correct partner to form a functional T-cell engaging complex). Both constructs comprise an anti-EP-CAM scFv. Construct 6246 comprises an anti-CD3E VH domain, whereas construct 6247 comprises an anti-CD3E VL domain. Neither construct contains an inert binding partner as a mispairing partner.

C. Two-Component System Constructs Using a Targeting scFv and a T-Cell Engaging Domain Mispaired to an Inert Binding Partner, as Well as a Protease Cleavage Site for Releasing the Inert Binding Partner Construct 6248 (SEQ ID NO: 168) and 6249 (SEQ ID NO: 169) are complementary constructs in a two-component system. Both constructs comprise an anti-EPCAM scFv. Construct 6248 comprises an anti-CD3E VH domain linked through a 25-mer linker having an MMP2 cleavage site (AIPVSLR (SEQ ID NO: 46)) to an inert binding partner VL domain from gantenerumab. Construct 6249 comprises an anti-CD3E VL domain linked through a 25-mer linker having an MMP2 cleavage site (AIPVSLR (SEQ ID NO: 46)) to an inert binding partner VH domain from clone alpha-MUC1-1 antibody.

D. Two-Component System Constructs with a Targeting Moiety, and a T-Cell Engaging Domain Mispaired with an Inert Binding Partner without a Protease Cleavage Site for Releasing the Inert Binding Partner Constructs 9327 (SEQ ID NO: 170) and 9328 (SEQ ID NO: 171) are two-component system constructs using an scFv targeting domain; however, they do not have a protease cleavage site for releasing the inert binding partner that serves as a mispairing moiety. Both constructs comprise an anti-EpCAM scFv for targeting the constructs to the unwanted cells expressing EpCAM. Construct 9327 comprises an anti-CD3E VH domain linked by a 25-mer linker that does not have a protease cleavage site corresponding to a protease used in the examples to an inert binding partner VL domain from gantenerumab. Construct 9328 comprises an anti-CD3E VL domain linked by a 25-mer linker that does not have a protease cleavage site corresponding to a protease used in the examples to an inert binding partner VH domain from clone alpha-MUC1-1 antibody.

Because these constructs do not have a protease cleavage site corresponding to a protease used in the examples, the inert binding partner will remain attached to the construct, preventing the two would-be complementary components of the two-component system from coming together to create an active anti-CD3E scFv.

E. Constructs Providing Different Targeting Moieties

Constructs 9329 (SEQ ID NO: 172) and 9330 (SEQ ID NO: 173) provide different targeting moieties. These constructs were intended to be used in two-component systems where one construct targets a first antigen on a cancer cell and the second construct targets a second antigen on the same cancer cell. Because the relative size of scFv and VHH targeting moieties are similar, these constructs were intended to "mix-and-match" with the pairable constructs having an anti-CD3E VL domain.

Construct 9329 comprises an anti-glypican-3 VHH sequence. It also comprises an anti-CD3E VH domain attached by a 25-mer linker comprising an MMP2 cleavage site (AIPVSLR (SEQ ID NO: 46)) to an inert binding partner VL domain from gantenerumab.

Construct 9330 comprises an anti-SDC1 scFv from indatuximab as the targeting moiety. It also comprises an anti-CD3E VH domain attached by a 25-mer linker comprising an MMP2 cleavage site (AIPVSLR (SEQ ID NO: 46)) to an inert binding partner VL domain from gantenerumab.

F. VHH/scFv Bispecific Constructs

Construct 9332 (SEQ ID NO: 174) and 9333 (SEQ ID NO: 175) are both VHH/scFv bispecific constructs comprising an anti-EGFR VHH portion and an anti-CD3E scFv portion. These two constructs do not comprise any insert binding domain.

G. Two-Component System Constructs Using a Targeting VHH Domain, a T-Cell Engaging Domain Mispaired to an Inert Binding Partner and Comprising a Protease Cleavage Site for Releasing the Inert Binding Partner Constructs 9334 (SEQ ID NO: 176) and 9335 (SEQ ID NO: 177) are complementary two-component system constructs using a targeting VHH domain. Both constructs comprise an anti-EGFR VHH domain for targeting to the unwanted cells expressing EGFR. Construct 9334 comprises an anti-CD3E VH domain linked by a 25-mer linker having an MMP2 cleavage site (AIPVSLR (SEQ ID NO: 46)) to an inert binding partner VL domain from gantenerumab. Construct 9335 was prepared comprising an anti-CD3E VH domain linked by a 25-mer linker having an MMP2 cleavage site (AIPVSLR (SEQ ID NO: 46)) to an inert binding partner VH domain from clone alpha-MUC1-1 antibody.

Thus, as a summary, the constructs are as provided in Table 4, with more detail and sequences provided above in Table 1B, with IBD standing for Inert binding partner.

TABLE 4

Construct Summary

| No. | Targeting Moiety | T-Cell Engaging Moiety? | IBD? Cleavage? | Pair with? |
|---|---|---|---|---|
| 6245 | anti-EpCAM scFv | anti-CD3E scFv | no IBD, no cleavage | no pairing necessary for TCE activity (positive control) |
| 6246 | anti-EPCAM scFv | anti-CD3E VH | no IBD, no cleavage | pairs with at least 6247 |
| 6247 | anti-EPCAM scFv | anti-CD3E VL | no IBD, no cleavage | pairs with at least 6246 |
| 6248 | anti-EPCAM scFv | anti-CD3E VH | MMP2 cleavage site and inert VL | pairs with at least 6249 |
| 6249 | anti-EPCAM scFv | anti-CD3E VL | MMP2 cleavage site and inert VH | pairs with at least 6248 |
| 9327 | anti-EpCAM scFv | anti-CD3E VH | no cleavage site and inert VL | cannot easily pair with 9328 because no cleavage site (negative control) |
| 9328 | anti-EpCAM scFv | anti-CD3E VL | no cleavage site and inert VH | cannot easily pair with 9327 because no cleavage site (negative control) |
| 9329 | anti-Glypican-3 VHH | anti-CD3E VH | MMP2 cleavage site and inert VL | "mix-and-match" with pairable constructs having an anti-CD3E VL domain |
| 9330 | anti-SDC1 scFv from indatuximab | anti-CD3E VH | MMP2 cleavage site and inert VL | "mix-and-match" with pairable constructs having an anti-CD3E VL domain |
| 9332 | anti-EGFR VHH (7D12) | anti-CD3E scFv | no IBD, no cleavage | no pairing necessary for TCE activity (positive control) |
| 9333 | anti-EGFR VHH (9D8) | anti-CD3E scFv | no IBD, no cleavage | no pairing necessary for TCE activity (positive control) |
| 9334 | anti-EGFR VHH | anti-CD3E VH | MMP2 cleavage site and inert VL | pairs with at least 9335 |

TABLE 4-continued

Construct Summary

| No. | Targeting Moiety | T-Cell Engaging Moiety? | IBD? Cleavage? | Pair with? |
|---|---|---|---|---|
| 9335 | anti-EGFR VHH | anti-CD3E VL | MMP2 cleavage site and inert VH | pairs with at least 9334 |

H. Preparation and Storage of all Constructs

Constructs were generated by DNA2.0 (Newark, Calif.) and expressed in HEK293T cells. Single-stranded oligonucleotides were designed to cover a specified sequence with a C-terminal hexahistidine tag to aid with down-stream purification. The oligonucleotides were chemically synthesized, then assembled using a variety of proprietary protocols depending on the sequence characteristics. In some instances, template independent PCR was used. In some instances, smaller sequences were assembled to create larger sequences by use of standard restriction enzyme digestion and ligase-mediated assembly. The assembled oligonucleotides were then cloned into standard E. coli plasmids and the complete double strand sequence verified by automated Sanger sequencing on ABI hardware. Constructs were expressed by transient transfection in HEK293T cells at the 150 ml scale and antibody fragments purified using affinity chromatography.

Before experiments began, constructs were thawed on ice and aliquoted under sterile conditions into low protein-binding tubes. Aliquots were stored at −80° C. until required. Aliquots were thawed on ice immediately prior to use. Aliquots were used for a maximum of five freeze-thaw cycles.

Example 2. Evaluation Construct Manufacturing

Figure 5A:
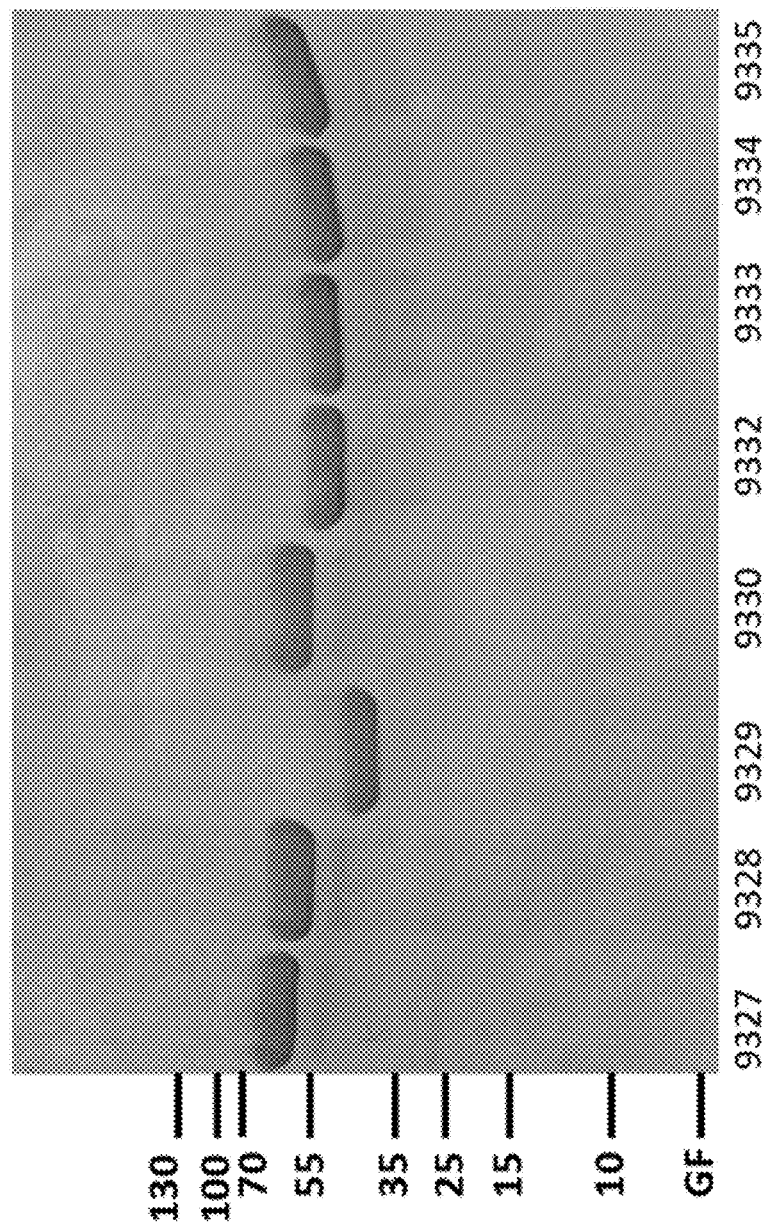
Figure 6:
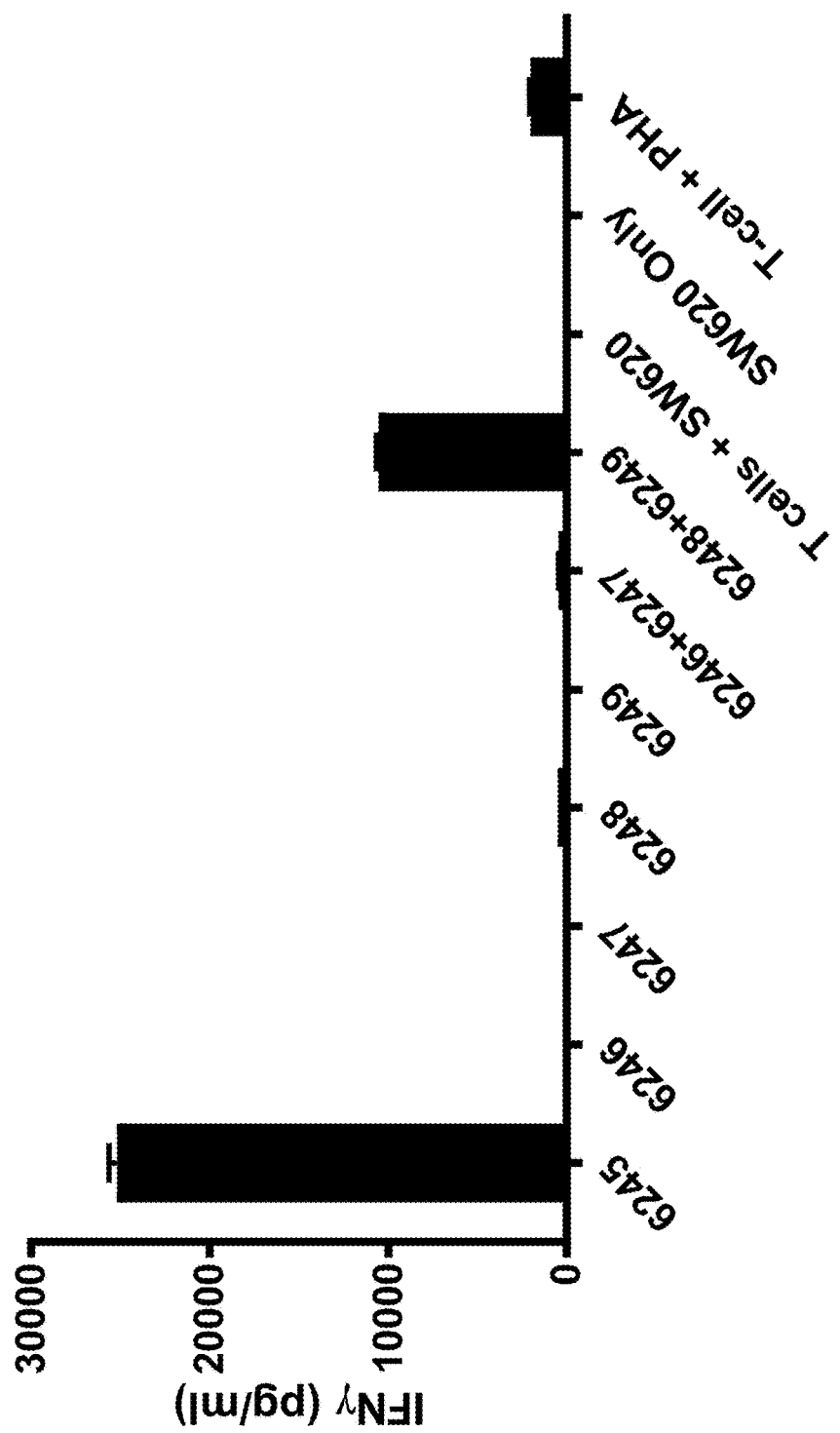
FIG. 6 shows IFNγ expression as a proxy for T cell response when cancer cells were treated with various individual constructs and combinations, with 6245 serving as a positive control and the combination of 6248 and 6249 showing beneficial results.
Figure 7:
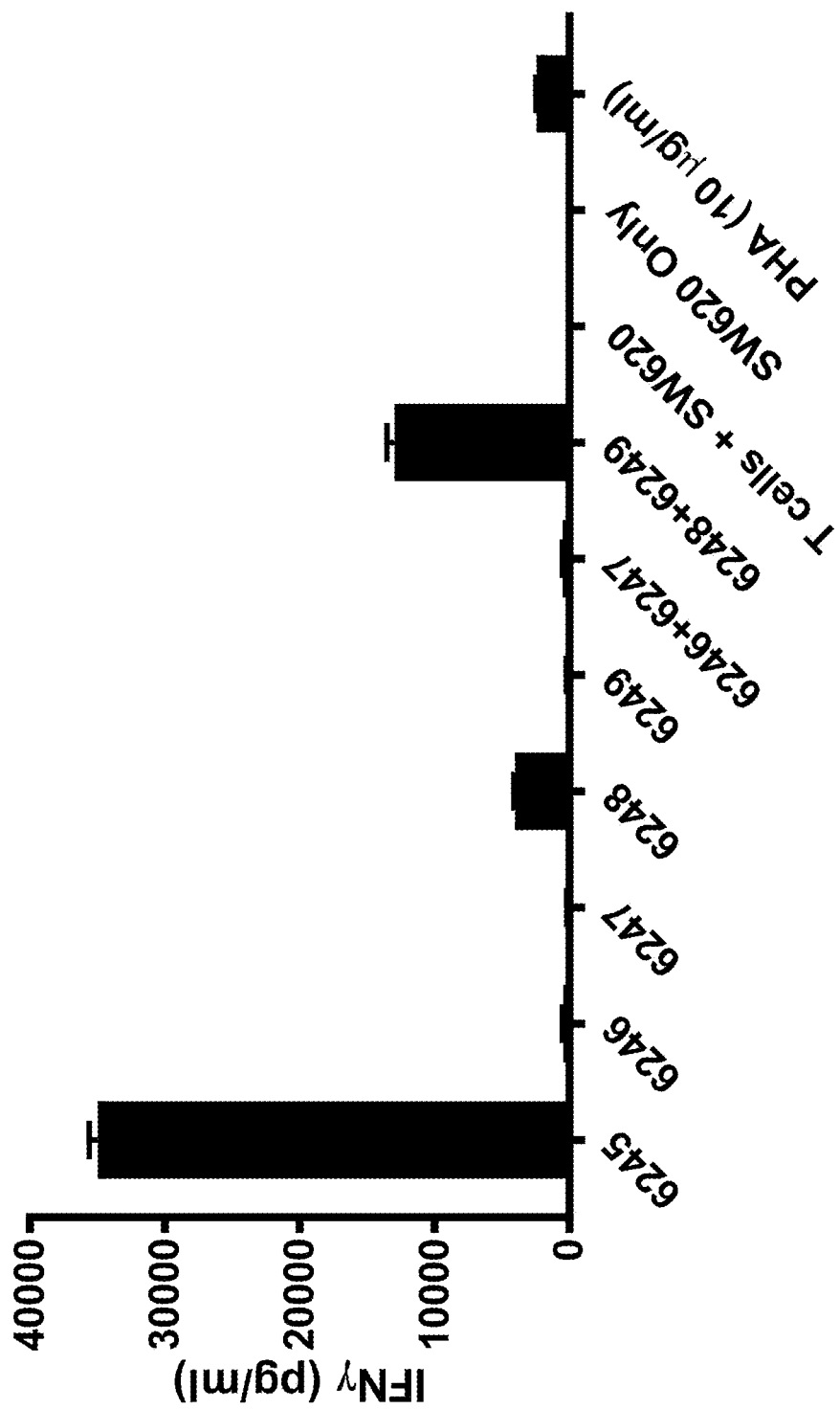
FIG. 7 shows IFNγ expression as a proxy for T cell response when cancer cells were treated with various individual constructs and combinations, with 6245 as a positive control and the combination of 6248 and 6249 showing beneficial results.

A. FIG. 5A: Evaluation of Constructs by SDS PAGE and Coomassie Blue Staining

Aliquots of antibody were thawed on ice, and diluted in 25 mM Tris pH7.4 to a final concentration of 2.0 mg/ml. If the constructs were already more dilute than this, the dilution step was omitted. An appropriate volume of 6× gel sample buffer (0.5 M Tris pH 6.8, 12% (w/v) SDS, 25% (v/v) glycerol, 5 mM EDTA, 200 mM N-ethylmaleimide) was added to each sample, which was then heated to 90° C. for 10 minutes.

10 μg of each construct was run on a 4-20% pre-cast gradient gel. Once run, gels were fixed for 30 minutes in stain buffer (10% (v/v) acetic acid, 50% (v/v) methanol and 40% (v/v) dH$_2$O) and then stained for 2 hours in Coomassie blue R-250 (0.25% in stain buffer), followed by de-staining for 2 to 3 hours in stain buffer with several changes of buffer as required. Gels were stored in 7% (v/v) acetic acid before documentation.

Results are shown in FIG. 5A. This shows that the proteins have been made and have very high purity, along with the correct molecular mass predicted by their sequence.

B. FIG. 5B

Additional constructs were evaluated in FIG. 5B. The method used for FIG. 5A was used for 5B.

Constructs 6245 (the bispecific construct not requiring pairing), 6248 (pairable constructs with an inert binding partner and an MMP2 cleavage site) were produced adequately. Constructs 6246 and 6247 (not containing an inert binding partner) were produced at low yields and are believed to be unstable. It is likely that the VH/VL pairing is important for fragment stability.

Thus, we believe that the constructs mispaired with an inert binding partner are more stable and easier to manufacture.

C. Yield

The yield of the constructs assessed in FIG. 5B was as follows:

TABLE 5

| Yields | |
|---|---|
| Construct | Yield (mg) |
| 6245 | 13.29 |
| 6246 | 0.57 |
| 6247 | 3.24 |
| 6248 | 17.54 |
| 6249 | 43.52 |

Example 3. Evaluation of IFNγ Expression in T-Cells Cells Mixed with Tumor Cell Lines and Treated with Various Constructs Preparations of single constructs and mixed constructs were tested for their IFNγ expression in order to test the ability of the complementary constructs in a two-component system to elicit a T-cell response.

Background of IFNγ Assays Generally:

Expression of cytokine markers in vitro, such as IFNγ expression, is known to have a predictive value for T cell responses and, thus, predicts in vivo results. As described in Ghanekar et al., Clin Diag Lab Immunol j8(3):628-31 (2001), IFNγ expression in CD8+ T cells measured by cytokine flow cytometry (CFC) is a surrogate marker for the response of cytotoxic T lymphocytes. Ghanekar at 628. Prior work showed that there is a strong correlation between the expression of IFNγ by CD8+ T cells and the activity of CTL effector cells. Ghanekar at 630. Prior work shows that the use of data on IFNγ expression allows greater accuracy in assessing CD8+ T-cell responses in a clinical setting. Id. at 631. This demonstrates that the cytokine expression assays herein were known to have predictive value for in vivo and clinical responses. While the methods herein do not follow the exact method steps of Ghanekar because there are multiple ways to assess IFNγ expression, Ghanekar demonstrates that IFNγ expression is a proxy for T-cell activity.

T Cell Line Culture:

Cytotoxic T cells were used in the IFNγ assays and cultured in RPMI-1640 medium containing 4.0 mM L-glutamine, 1% penicillin and streptomycin, 10% heat-inactivated FBS, 1% heat-inactivated human serum (pooled AB serum, TCS Bioscience) and 1,000 U/ml IL-2. Cells were kept at a density of 1-2×10$^6$ cells/ml, and were fed by replacement of three quarters of the medium every 48 hours. They were originally generated by adding 10 ug HLA-A*0201-restricted viral peptide NLVPMVATV (SEQ ID NO: 178) to 10 million peripheral blood mononuclear cells (PBMCs) from an HLA-A*0201+ donor. Cells were cultured in RPMI-1640 medium containing 4.0 mM L-glutamine, 1% penicillin and streptomycin, 10% heat-inactivated FBS and 1% heat-inactivated human serum (pooled AB serum, TCS Bioscience) for four days before the media was changed to include 1000 U/ml IL-2. The T cells were predominantly CD8+ T cells with a small amount of CD4+ T cells as well.

Tumor Cell Line Culture:

The following cell lines were used: SW620, MCF-7, SNU398, and U266. Cells were cultured in DMEM containing 10% FBS, and 1% penicillin/streptomycin solution except SNU398 and U266 cells which were cultured in RPMI-1640 medium containing 10% heat-inactivated FBS, 2 mM glutamine and 1% penicillin/streptomycin solution. SW620 cells are derived from a human colon cancer metastasis. MCF-7 cells are derived from a human breast cancer metastatic site (pleural effusion). SNU398 cells are derived from a human anaplastic hepatocellular carcinoma patient in 1990. U266 cells are derived from a human male multiple myeloma patient secreting IgE.

Impact of Constructs on IFNγ Production:

Adherent cell lines were plated in a 96 well plate (100,000 cells per well) for at least 16 hours. Non-adherent cells (100,000 cells per well) were plated on the day of the experiment by centrifuging the culture at 400×g for 5 minutes and resuspending the cells in T cell medium. 20,000 T cells per well in T cell medium were added. Constructs were made up in T cell medium and added to the cultures. Where mixtures of constructs were used, these were pre-mixed before addition to the cultures. The final volume in the culture was 200 µl per well. Cultures were incubated for 24 hours at 37° C., 5% $CO_2$ and 100% relative humidity. The cultures were centrifuged at 400×g for 5 minutes and the supernatants aspirated and placed in a separate plate. Supernatants were stored at −20° C. until analyzed for IFNγ.

IFNγ ELISA:

IFNγ levels in tissue culture supernatants were assayed using either an eBioscience Ready-Set-Go ELISA kit (cat. no. 88-7316-88) or a BioLegend Human IFNγ ELISA Max kit (cat. no. 430106) as per the manufacturer's instructions.

A. FIG. 6

IFNγ was evaluated for various single constructs and mixed constructs. The IFNγ production and ELISA assay protocols provided above were used, except as noted. SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/ml) were made up in T cell medium and added to the culture. Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% CO2 and 100% relative humidity. The culture was centrifuged at 400×g for 5 minutes and the supernatants aspirated and placed in a separate plate. Supernatants were stored at −20° C. until analyzed for IFNγ.

IFNγ was evaluated for various single constructs and mixed constructs. Single constructs were assessed, with construct 6425 (a bispecific scFv for EpCAM and CD3E) was serving as a positive control. Baseline IFNγ was assessed in T-cells with SW620 cancer cells, SW620 cancer cells alone, and T-cells stimulated nonspecifically with phytohaemagglutinin (PHA) to show the capacity of T-cells for IFNγ expression.

In SW620 tumor cells, constructs were used at a final concentration of 1 µg/ml. Cultures were incubated for 4 hours and the supernatants were assayed for IFNγ. Mean±standard deviation of triplicates are provided. was evaluated for various single constructs and mixed constructs. Cultures were incubated for 4 hours and the supernatants were assayed for IFNγ. Mean±standard deviation of triplicates are provided. Constructs were used at a final concentration of 1 µg/ml. Cultures were incubated for 24 hours and the supernatants were assayed for IFNγ. Mean±standard deviation of triplicates are provided.

Construct 6245 serves as a positive control because this construct has both a targeting anti-EpCAM scFv and an anti-CD3E scFv; thus, it is a bispecific construct not requiring pairing for T-cell engaging (TCE) activity.

Constructs 6248 and 6249 (pairs of a two-component system each having an inert binding partner separated from the anti-CD3E T-cell engaging VL or VH, respectively, by a linker with an MMP2 cleavage site) showed more IFNγ expression when paired together than when administered alone. The combination of 6246 and 6247 (pairs of a two-component system without any mispairing to an inert binding partner or protease cleavage site required for them to associate) yield a much lower response than the combination of 6248 and 6249 likely because the 6246 and 6247 are not protected during manufacturing by the inert binding partner, which is believed to stabilize the unpaired anti-CD3E VH and VL domains in each construct, respectively. Thus, we believe that the mispaired constructs having an inert binding partner are more stable and easier to manufacture than precleaved constructs having an unpaired anti-CD3E VH or VL domain.

B. FIG. 7

IFNγ was evaluated for various single constructs and mixed constructs. SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/ml) were made up in T cell medium and added to the culture. Where mixtures of constructs were used, these were pre-mixed before addition to the cultures (final concentration of constructs was 1 µg/ml per construct). Controls were PHA-M (final concentration 10 µg/m), SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ. Mean±standard deviation of triplicates are provided.

Construct 6245 serves as a positive control because this construct has both a targeting anti-EpCAM scFv and an anti-CD3E scFv; thus, it is a bispecific construct not requiring pairing for T-cell engaging (TCE) activity.

Constructs 6248 and 6249 (pairs of a two-component system each having an inert binding partner separated from the anti-CD3E T-cell engaging VL or VH, respectively, by a linker with an MMP2 cleavage site) showed more IFNγ expression when paired together than when administered alone. The combination of 6246 and 6247 (pairs of a two-component system without any binding domain or protease cleavage site required for them to associate) yield a much lower response than the combination of 6248 and 6249 likely because the 6246 and 6247 are not protected during manufacturing by the inert binding partner, which is believed to stabilize the unpaired anti-CD3E VH and VL domains in each construct, respectively. Thus, we believe that the mispaired constructs having an inert binding partner are more stable and easier to manufacture than constructs with an unpaired anti-CD3E VH or VL domain.

C. FIG. 8

Figure 8:
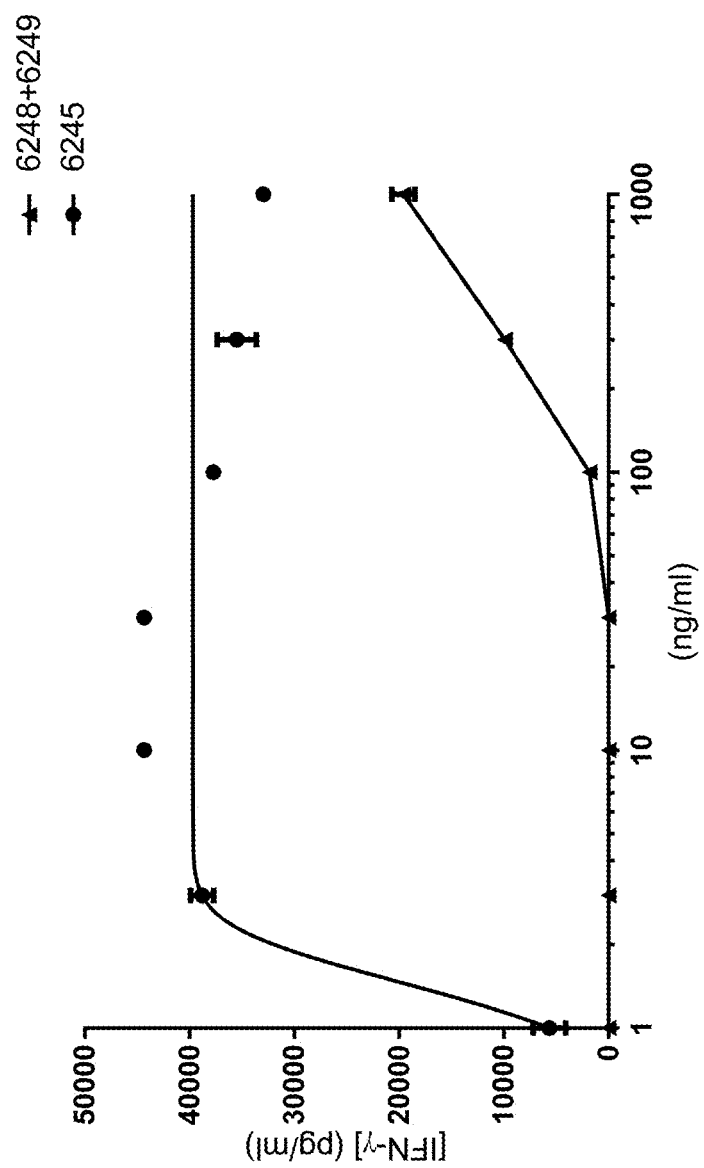
FIG. 8 shows IFNγ expression as a proxy for T cell response when cancer cells were treated with different concentrations of constructs, with 6245 as a positive control and the combination of 6248 and 6249 showing beneficial results.

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration ranging from 1 ng/ml to 1 µg/ml) were made up in T cell medium and added to the culture. Where mixtures of constructs were used, these were pre-mixed before addition to the cultures (final concentration of constructs ranged from 1 ng/ml to 1 µg/ml per construct). Controls were SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ. Mean±standard deviation of triplicates were shown in FIG. 8.

Construct 6245 served as a positive control and paired constructs 6248 and 6249 were assessed. Both the control construct and the paired two-component system showed IFNγ expression. This demonstrates that the inert VL and VH domains are being cleaved from constructs 6248 and 6249, respectively, and that these two constructs are pairing to create a complete anti-CD3E scFv, which is capable of engaging T cells.

The two-component system (6248 and 6249) has a lower potency than the bispecific 6245 construct, yet is still in an acceptable range and may actually offer dosing advantages in avoiding side effects.

D. FIGS. 9A-B

Figure 9:
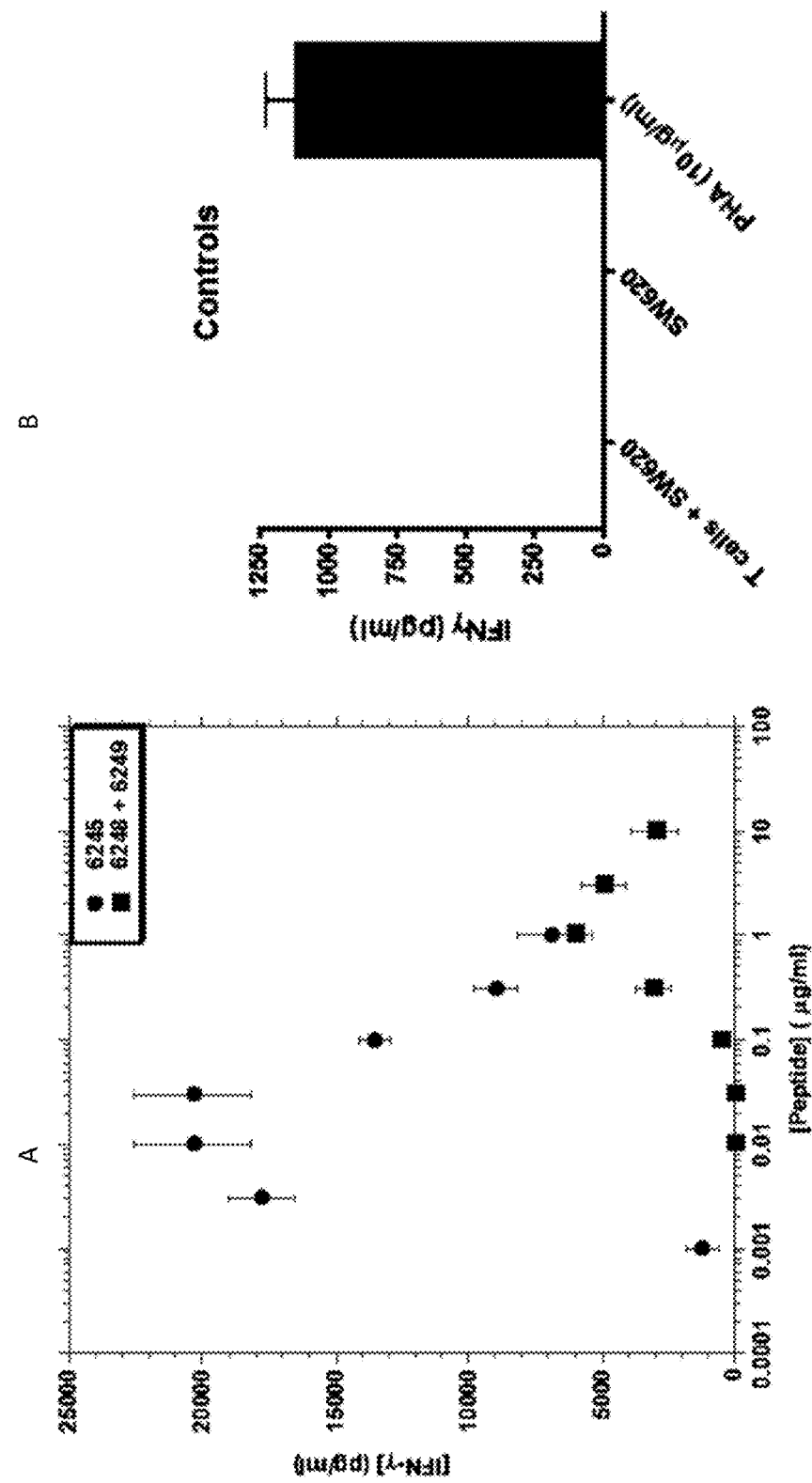
FIGS. 9A-B shows IFNγ expression as a proxy for T cell response when cancer cells were treated with controls or different concentrations of constructs, with 6245 as a positive control and the combination of 6248 and 6249 showing beneficial results. PHA also served as a positive control for nonspecific T-cell activation.

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration ranging from 1 ng/ml to 1 µg/ml) were made up in T cell medium and added to the culture. Where mixtures of constructs were used, these were pre-mixed before addition to the cultures (final concentration of constructs ranged from 10 ng/ml to 10 µg/ml per construct). Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% CO2 and 100% relative humidity. The culture was centrifuged at 400×g for 5 minutes and the supernatants aspirated and placed in a separate plate. Supernatants were stored at −200° C. until analyzed for IFNγ. Mean±standard deviation of triplicates were shown in FIGS. 9A-B.

Both the control construct and the paired two-component system showed IFNγ expression. This demonstrates that the inert VL and VH domains are being cleaved from constructs 6248 and 6249, respectively, and that these two constructs are pairing to create a complete anti-CD3E scFv, which is capable of engaging T cells.

The two-component system (6248 and 6249) has a lower potency than the bispecific 6245 construct, yet is still in an acceptable range and may actually offer dosing advantages in avoiding side effects.

E. FIG. 10

Figure 10:
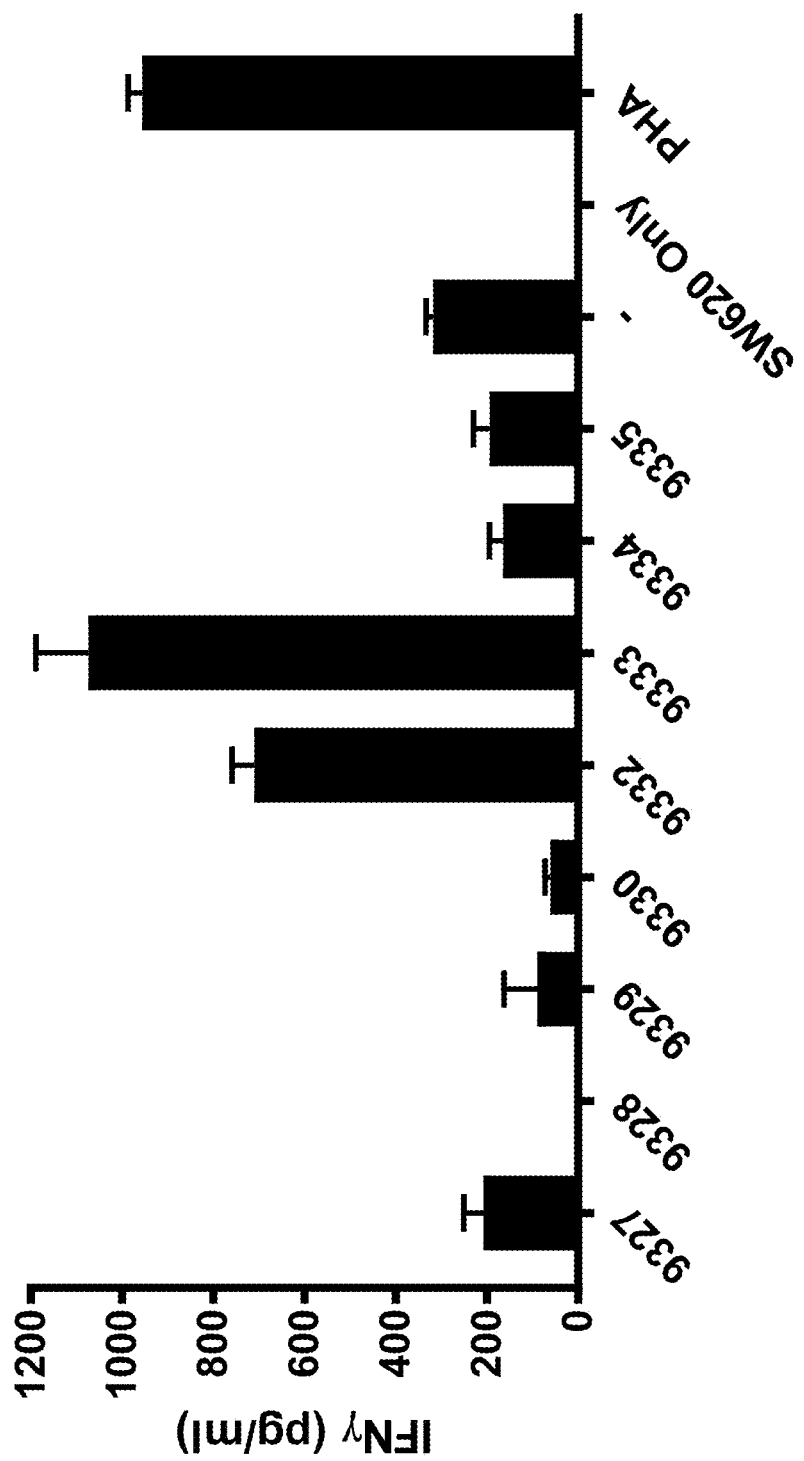
FIG. 10 shows IFNγ expression as a proxy for T cell response when cancer cells were treated with controls or different concentrations of constructs, with very low levels with constructs having only a VH or VL for the anti-CDE3 scFv, but positive control bispecific constructs (both 9332 and 9333) showed higher levels of activity.

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/ml) were made up in T cell medium and added to the culture. Where mixtures of constructs were used, these were pre-mixed before addition to the cultures (final concentration of constructs was 1 µg/ml per construct). Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ. FIG. 10 provides mean±standard deviation of triplicates.

FIG. 10 shows a very low level of IFNγ expression for constructs with only a VH or VL for the anti-CD3E scFv; however, positive bispecific constructs with a full scFv (9332 and 9333) showed higher IFNγ expression levels.

F. Stoichiometric Assessment of Complementary Constructs of a Two-Component System (FIG. 11)

Figure 11:
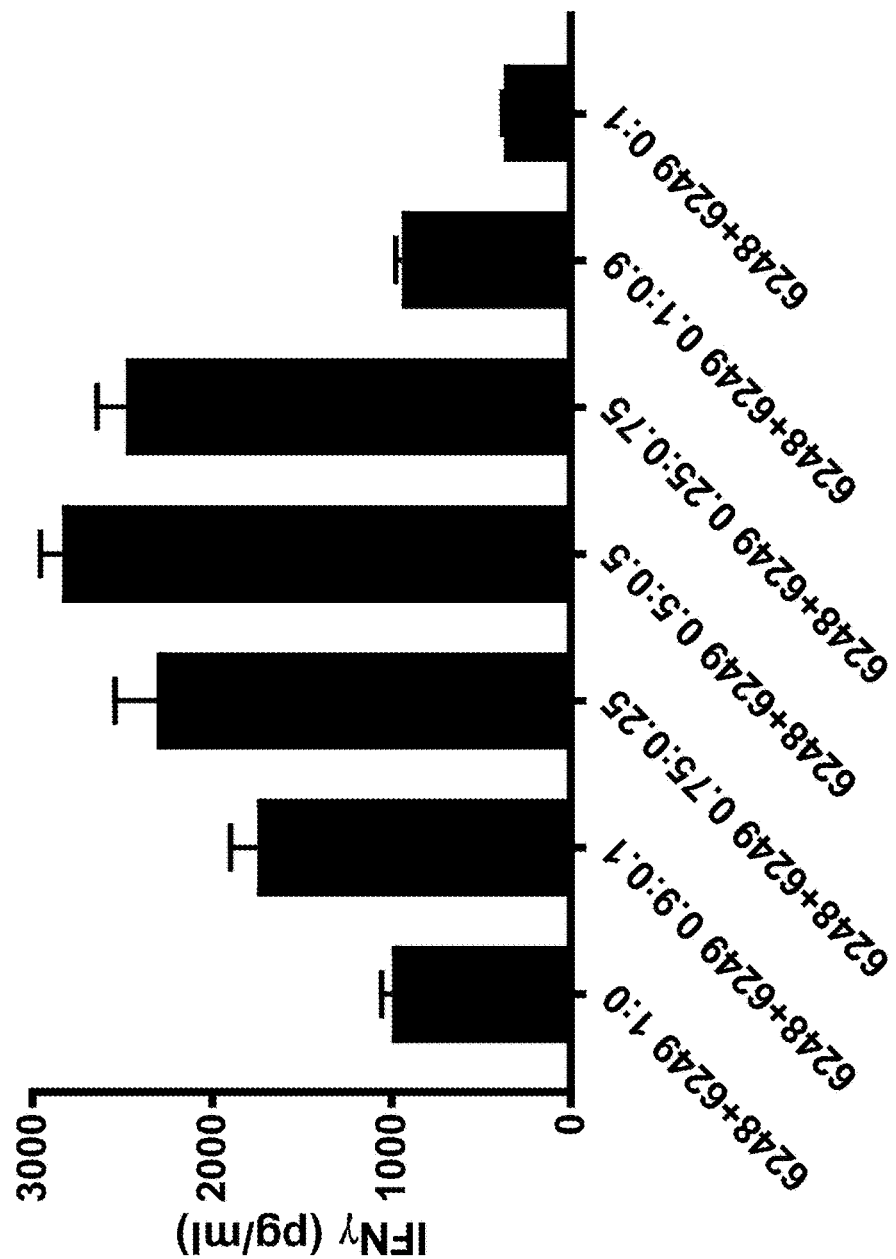
FIG. 11 provides a stoichiometric assessment of complementary constructs of a two-component system.

Complementary constructs of a two-component system (6248 and 6249) were added together in varying ratios, as shown in FIG. 11.

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs were pre-mixed in the specified ratios in T cell medium and added to the culture (final concentration of constructs was 1 µg/ml in total). The two components 6248 and 6249, one containing the VH domain of the CD3 activating moiety (6249) and the other containing the VL domain of the CD3 activating moiety (6248), were pre-mixed at ratios 100:0, 90:10, 75:25, 50:50, 25:75, 10:90 and 0:100. The mixtures of the two components were added to 100,000 unwanted tumor cells and 20,000 T cells. Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ.

The results in FIG. 11 demonstrate an increasing activation of T cells as the ratio of the two components reaches equilibrium. When there is an excess of either the component containing the VH domain of the CD3 activating moiety (6249) or the other component containing the VL domain of the CD3 activating moiety (6248), the activation of T cells is decreased as the activation is reliant on both the VH and VL of the CD3 activating moiety coming together. Therefore, IFNγ expression levels were much lower when all or nearly all of the constructs provided were of one type or the other. The highest IFNγ expression level corresponds to the scenario where an equal amount of each of the two complementary constructs were provided. This provides further evidence demonstrating that the IFNγ expression is caused by the two halves of the anti-CD3E scFv coming together from the two constructs in the two-component system.

G. Use of MCF-7 Cells (FIG. 12)

Figure 12:
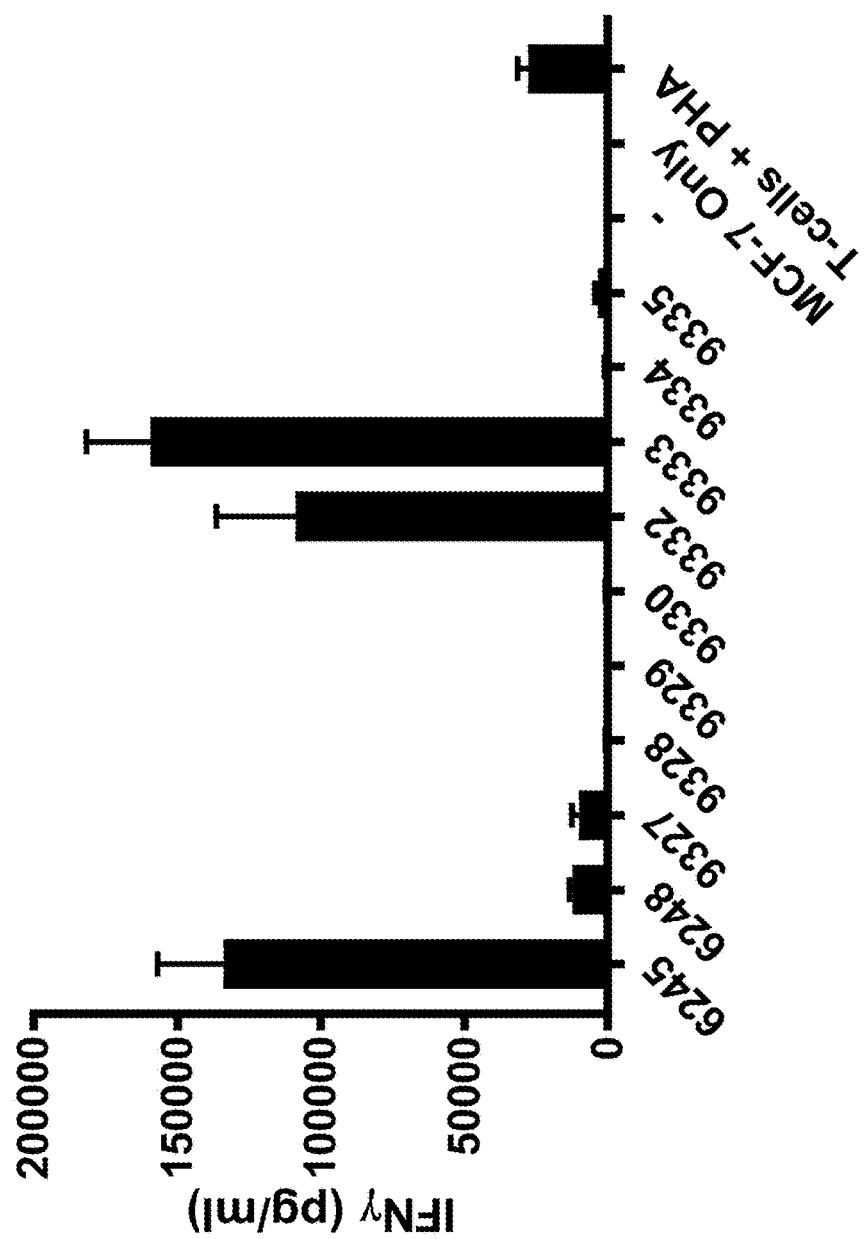
FIG. 12 shows IFNγ expression as a proxy for T cell response when MCF-7 cancer cells were treated with controls or different concentrations of constructs.

FIG. 12 shows experiments conducted in the MCF-7 tumor cell line. MCF-7 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/ml) were made up in T cell medium and added to the culture. Controls were PHA-M (final concentration 10 µg/ml), MCF-7 cells plus T cells with no additions, and MCF-7 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ.

Similar results were achieved to the other cell lines used. In FIG. 12, positive control constructs 6245, 9332, and 9333 (each having a full anti-CD3E scFv) showed much higher IFNγ expression levels than any of the single components comprising only a VH or VL domain from the anti-CD3E antibody. FIG. 12 also provides baseline IFNγ expression levels for MCF-7 cells alone or T-cells stimulated nonspecifically with PHA.

H. FIGS. 13-14

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/m) were made up in T cell medium and added to the culture. Where mixtures of constructs were used, these were pre-mixed before addition to the cultures (final concentration of constructs was 1 µg/ml per construct). Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ.

Figure 13:
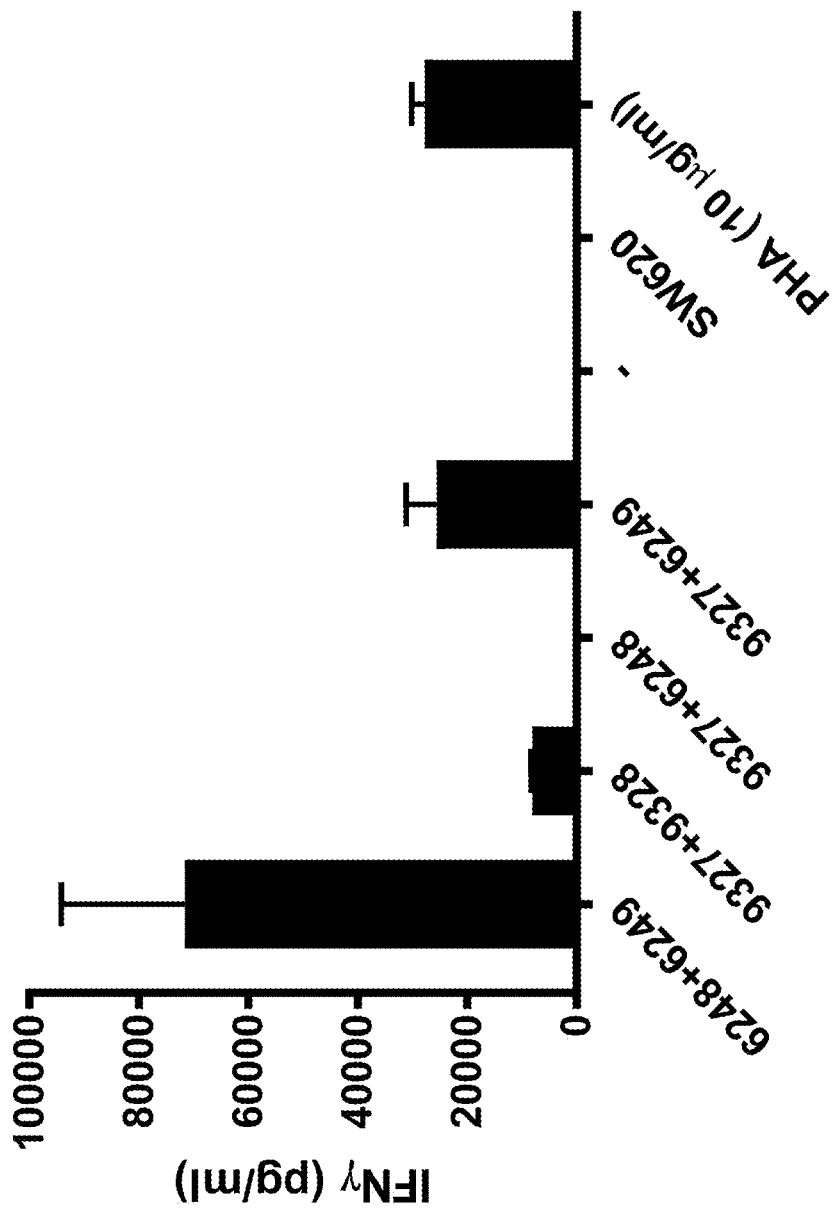
FIG. 13 shows IFNγ expression as a proxy for T cell response when cancer cells were treated with controls or different concentrations of constructs targeting EpCAM.

In FIG. 13, the data show that the two-component system of 6248 and 6249 functions as expected because these constructs have an inert binding partner that can be cleaved by an MMP2 cleavage site and pairable anti-CD3E variable domains (one VH in 6248 and one VL in 6249). Constructs 9327 and 9328 do not generate a strong IFNγ signal because neither of these constructs has a cleavage site between the inert binding partner and the anti-CD3E variable domain.

Constructs 9327 and 6248 do not show any activity because they both have VH domains for the anti-CD3E antibody and cannot make a functional anti-CD3E scFv; additionally, 9327 does not have a cleavage site. 9327 and 6249 show a very low level of activity because 9327 has no cleavage site and 6249 has a cleavage site, but the two together can make an anti-CD3E scFv if some low level of spontaneous cleavage occurs.

Figure 14:
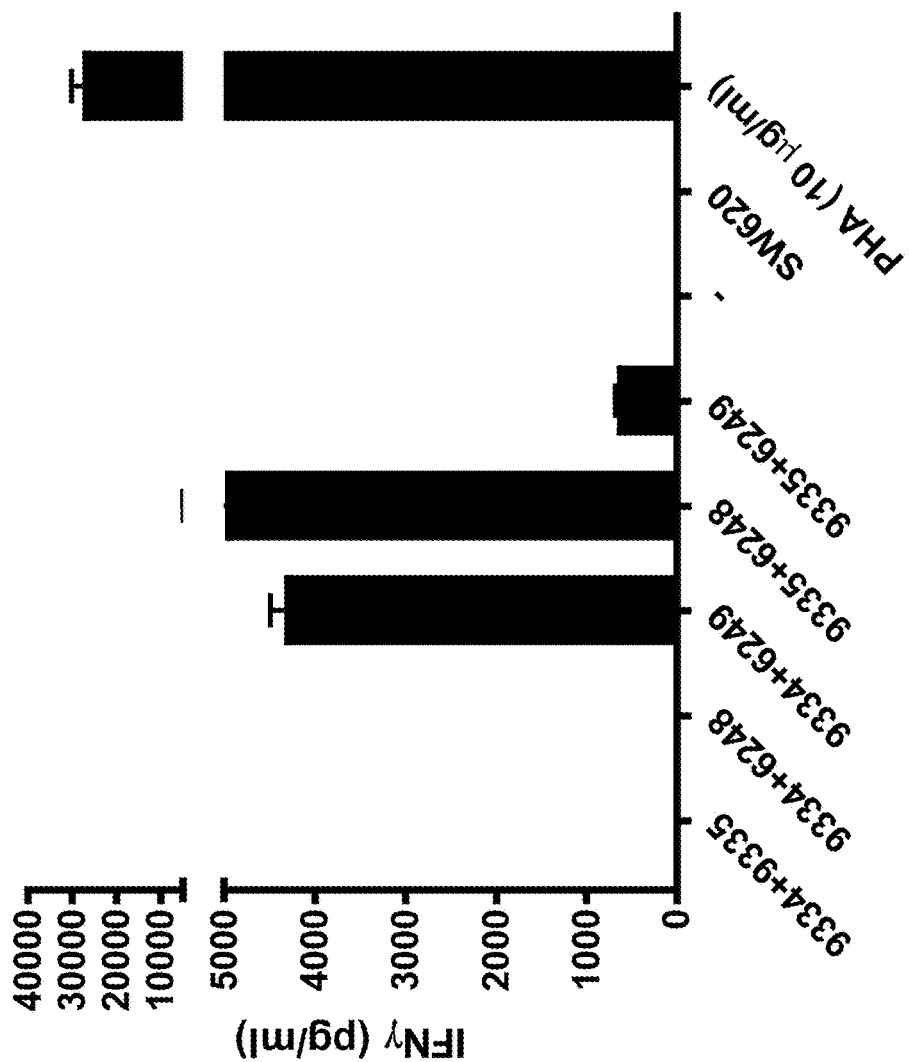
FIG. 14 shows IFNγ expression as a proxy for T cell response when cancer cells were treated with controls or different concentrations of constructs targeting either biparatopic EGFR epitopes or a combination of EpCAM and EGFR targeting.

In FIG. 14, the pairing of constructs 9334 and 9335 (providing biparatopic approach to targeting EFGR, with targeting antibody scFvs to different epitopes on EGFR) did not create an IFNγ signal. It is believed that either the epitopes on EGFR were too far apart for the two anti-CD3E variable domains to reach each other or the epitopes were too close and creating steric hindrance for binding on the antibody side. It is, however, very reasonable to test biparatopic combinations. Another antibody for EGFR can be identified and tested for combinations in this approach.

FIG. 14 also shows targeting two different proteins expressed on the same cancer cell. Construct 6248 binds EpCAM and is successfully paired with 9335, which binds EGFR. Construct 6249 also binds EpCAM and is successfully paired with 9334. This establishes that different molecules on a cancer cell may be targeted, providing yet a further layer of specificity for some embodiments of the two-component system described herein. This also provides further evidence that components 9335 and 9334 work in other contexts and further suggests these components were either too close or too far from each other in their combination with each other described above.

The combination of 9334 and 6249 provides useful information in this figure, demonstrating that dual targeting can be achieved because construct 9334 targets EGFR and 9249 targets EpCAM.

The combination of 9334 and 6248 was not expected to have activity because both constructs comprise a VH from the anti-CD3E antibody and neither construct comprises a VL from that antibody.

I. FIG. 15

SNU398 cells were cultured in RPMI1640 containing 10% FBS, 2 mM glutamine and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/ml) were made up in T cell medium and added to the culture. Where mixtures of constructs were used, these were pre-mixed before addition to the cultures (final concentration of constructs was 1 µg/ml per construct). Controls were PHA-M (final concentration 10 gig/ml), SNU398 cells plus T cells with no additions, and SNU398 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ.

Figure 15:
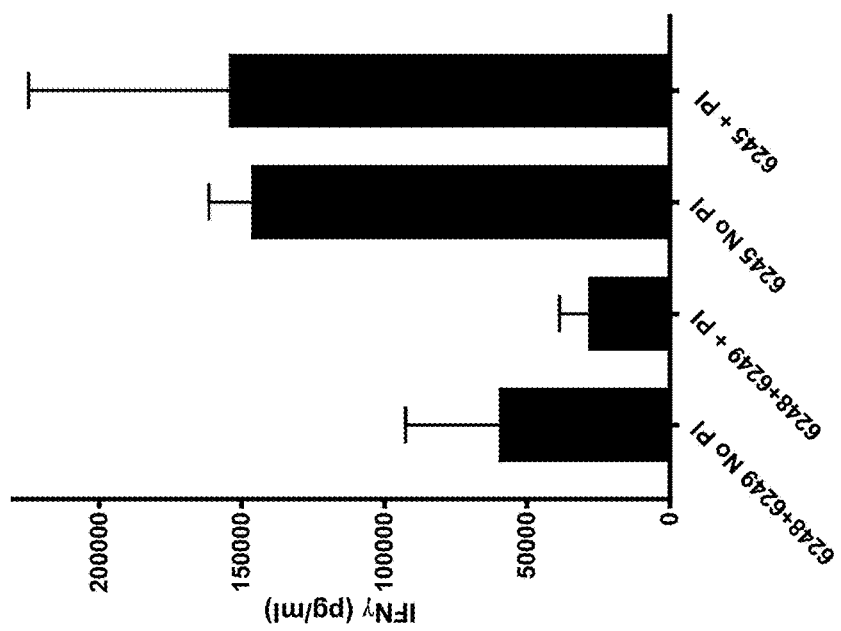
FIG. 15 shows the impact of protease inhibitors on constructs either containing protease cleavage sites or not containing protease cleavage sites.
Figure 16:
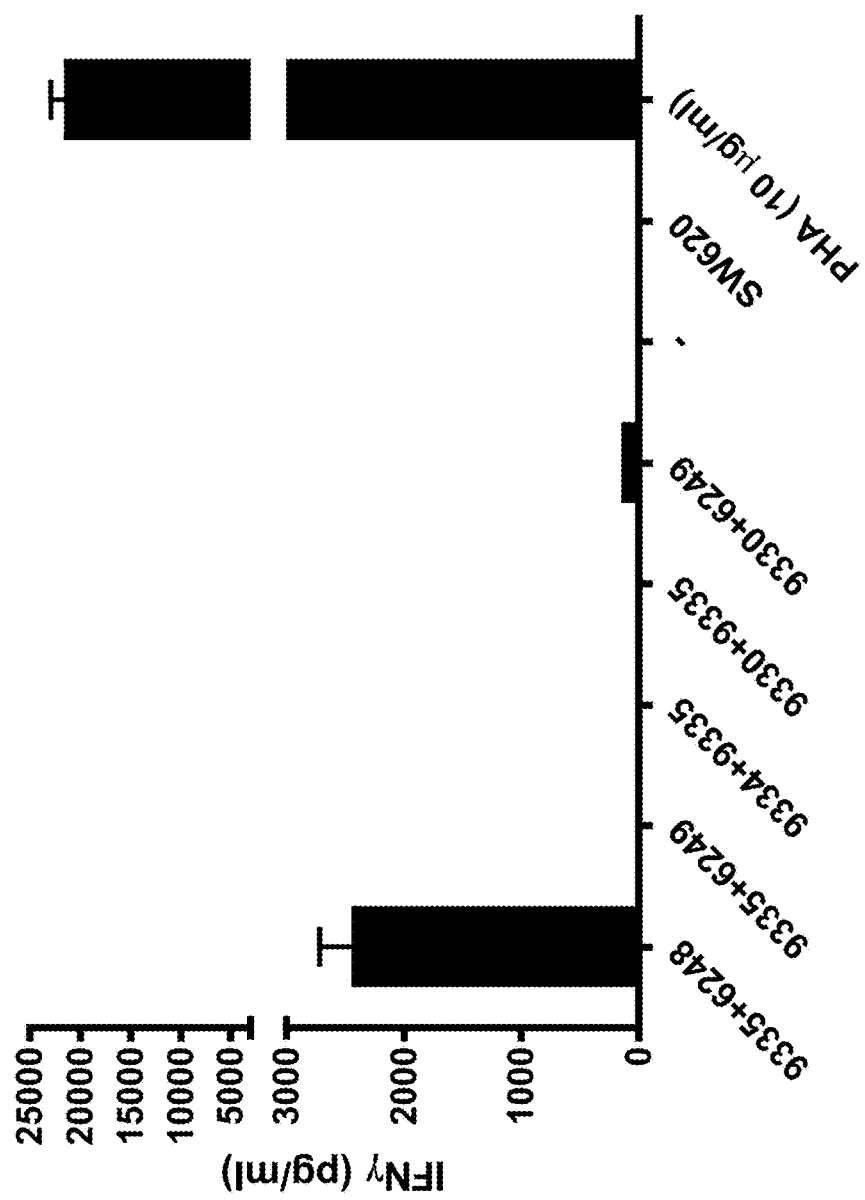
FIG. 16 shows that different types of targeting moieties may be used, by successfully pairing a construct having a VHH targeting moiety with a construct having an scFv moiety.

FIG. 15 shows that adding a protease inhibitor reduces the IFNγ expression of the two-component system having a protease cleavage site (constructs 6248 and 6249). The protease inhibitor does not impact the 6245 bispecific construct as cleavage and pairing are not required for activity.

J. FIG. 16

SW620 cells were cultured in DMEM containing 10% FBS, and 1% penicillin/streptomycin solution. Cells were plated in a 96 well plate (100,000 cells per well) on the day prior to the experiment. On the day of the experiment the medium was aspirated and discarded. 20,000 T cells per well in T cell medium were added. Constructs (final concentration of 1 µg/m) were made up in T cell medium and added to the culture. Where mixtures of constructs were used, these were pre-mixed before addition to the cultures (final concentration of constructs was 1 µg/ml per construct). Controls were PHA-M (final concentration 10 µg/ml), SW620 cells plus T cells with no additions, and SW620 cells without T cells or other additions. Each condition was run in triplicate. The final volume in the culture was 200 µl per well. The culture was incubated for 24 hours at 37° C., 5% $CO_2$ and 100% relative humidity. The culture was centrifuged at 400×g for 5 minutes and the supernatants aspirated and placed in a separate plate. Supernatants were stored at −20° C. until analyzed for IFNγ.

The functional combination of 9335 and 6248 shows that different kinds of antibody fragments may be combined in a first component and second component, respectively. 9335 employs an anti-EGFR VHH as the targeting moiety and 6248 employs an anti-EPCAM scFv as the targeting moiety.

Example 4. In Vivo Targeting of B Cell Lymphoma Using a Two-Component System A two-component system comprising a first component and a second component are administered to a patient having lymphoma. The first component comprises Rituximab or an anti-CD22 antibody as a targeting moiety, a VH domain from an antibody binding CD3 as a T-cell engaging domain, a VL domain as an inert binding partner, and the ADAM28 cleavage site KPAKFFRL (SEQ ID NO: 1). The second component also comprises Rituximab or an anti-CD22 antibody as a targeting moiety, the complementary VL domain from an antibody binding CD3 as a T-cell engaging domain, VH as an inert binding partner, and the ADAM28 cleavage site KPAKFFRL (SEQ ID NO: 1). The VH domain from an antibody binding CD3 as a T-cell engaging domain of the first component and the VL domain from an antibody binding CD3 as a T-cell engaging domain of the second component are capable of binding to each other when not bound to an inert binding partner and possessing the activity to engage a T-cell.

The patient is infused with the agent, which targets all B cells, healthy and malignant. Upon binding malignant cells, the agent comes into contact with proteases whereby cleavage of the protease recognition domain releases the inert binding partners from both the first and the second T-cell engaging domains.

The malignant B cells that are bound by the now-activated two-component system complex attracts the host immune system for cytolysis by T-cells due to the presence and activity of the complex of the first and second T-cell engaging domains.

Example 5. Specific Embodiments of Two-Component Systems

A two-component system chosen from System A-E is prepared according to Table 3 and administered to a patient having cancer. If an item is described as optional, the row of the table describes both two-component systems having or not having that item.

TABLE 6

Certain Embodiments of the Two-Component System

| | | First Component | | | | |
|---|---|---|---|---|---|---|
| | Targeting Moiety | T-Cell Engaging Moiety | Cleavage Site | Inert binding partner | Optional Linker(s) & Location(s) | |
| A | Antibody targeting HER2 | $V_H$ of antibody targeting CD3 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). | |

| | | Second Component | | | | |
|---|---|---|---|---|---|---|
| | Optional Targeting Moiety | T-Cell Engaging Moiety | Optional Cleavage Site | Optional Inert binding partner | Optional Linker(s) & Location(s) | |
| | Antibody targeting HER2 | $V_L$ of antibody targeting CD3 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). | |

| | | First Component | | | | |
|---|---|---|---|---|---|---|
| | Targeting Moiety | T-Cell Engaging Moiety | Cleavage Site | Inert binding partner | Optional Linker(s) & Location(s) | |
| B | antibody targeting EGFR, such as Cetuximab | $V_H$ of antibody targeting CD4 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). | |

TABLE 6-continued

Certain Embodiments of the Two-Component System

Second Component

| | Optional Targeting Moiety | T-Cell Engaging Moiety | Optional Cleavage Site | Optional Inert binding partner | Optional Linker(s) & Location(s) |
|---|---|---|---|---|---|
| | antibody targeting EGFR, such as Cetuximab | $V_L$ of antibody targeting CD4 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

First Component

| | Targeting Moiety | T-Cell Engaging Moiety | Cleavage Site | Inert binding partner | Optional Linker(s) & Location(s) |
|---|---|---|---|---|---|
| C | antibody targeting CD20, such as Rituximab | $V_H$ of antibody targeting CD8 | Any ADAM28 cleavage site | Any VH domain that binds to the VL domain of the T-cell engaging domain without creating any binding specificity | For example, GGGGS (SEQ ID No: 45). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

Second Component

| | Optional Targeting Moiety | T-Cell Engaging Moiety | Optional Cleavage Site | Optional Inert binding partner | Optional Linker(s) & Location(s) |
|---|---|---|---|---|---|
| | antibody targeting CD20, such as Rituximab | $V_L$ of antibody targeting CD8 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

First Component

| | Targeting Moiety | T-Cell Engaging Moiety | Cleavage Site | Inert binding partner | Optional Linker(s) & Location(s) |
|---|---|---|---|---|---|
| D | antibody targeting CD22, such as Inotuzumab | $V_H$ of antibody targeting CD28 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

Second Component

| | Optional Targeting Moiety | T-Cell Engaging Moiety | Optional Cleavage Site | Optional Inert binding partner | Optional Linker(s) & Location(s) |
|---|---|---|---|---|---|
| | antibody targeting CD22, such as Inotuzumab | $V_L$ of antibody targeting CD28 | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

TABLE 6-continued

Certain Embodiments of the Two-Component System

First Component

| | Targeting Moiety | T-Cell Engaging Moiety | Cleavage Site | Inert binding partner | Optional Linker(s) & Location(s) |
|---|---|---|---|---|---|
| E | antibody targeting CD33, such as Gemtuzumab | $V_H$ of antibody targeting T cell receptor (TCR) | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

Second Component

| Optional Targeting Moiety | T-Cell Engaging Moiety | Optional Cleavage Site | Optional Inert binding partner | Optional Linker(s) & Location(s) |
|---|---|---|---|---|
| antibody targeting CD33, such as Gemtuzumab | $V_L$ of antibody targeting T cell receptor (TCR) | Any ADAM28 cleavage site | Any VH domain that binds to the VL domain of the T-cell engaging domain without creating any binding specificity | For example, GGGGS (SEQ ID No: 85). Located between the $V_H$ and $V_L$ of the targeting moiety, between the targeting moiety and the inactive T-cell engaging domain, and/or between the $V_H$ and $V_L$ of the inactive T-cell engaging domain (See FIG. 1). |

Example 6. Embodiments

The following numbered items provide embodiments as described herein, though the embodiments recited here are not limiting.

Item 1. A two-component system for treating a condition characterized by the presence of unwanted cells comprising:
  a. a first component comprising a targeted T-cell engaging agent comprising:
    i. a first targeting moiety that is capable of targeting the unwanted cells;
    ii. a first T-cell engaging domain capable of T-cell engaging activity when binding a second T-cell engaging domain, wherein the second T-cell engaging domain is not part of the first component;
    iii. a first inert binding partner for the first T-cell engaging domain binding to the first T-cell engaging domain such that the first T-cell engaging domain does not bind to the second T-cell engaging domain unless the inert binding partner is removed; and
    iv. a cleavage site separating the first T-cell engaging domain and the first inert binding partner, wherein the cleavage site is:
      (1) cleaved by an enzyme expressed by the unwanted cells;
      (2) cleaved through a pH-sensitive cleavage reaction inside the unwanted cell;
      (3) cleaved by a complement-dependent cleavage reaction; or
      (4) cleaved by a protease that is colocalized to the unwanted cell by a targeting moiety that is the same or different from the targeting moiety in the agent,
  b. a second component comprising a second T-cell engaging domain capable of T-cell engaging activity when binding the first T-cell engaging domain,
wherein the first and second T-cell engaging domains are capable of binding when neither is bound to an inert binding partner.

Item 2. The two-component system of item 1, wherein the second component further comprises a second targeting moiety that is capable of targeting the unwanted cells.

Item 3. The two-component system of any one of items 1-2, wherein the second component further comprises a second inert binding partner for the second T-cell engaging domain binding to the second T-cell engaging domain such that the second T cell engaging domain does not bind to the first T-cell engaging domain unless the inert binding partner is removed and
  a. a cleavage site separating the second T-cell engaging domain and the second inert binding partner, wherein the cleavage site is:
    i. cleaved by an enzyme expressed by the unwanted cells;
    ii. cleaved through a pH-sensitive cleavage reaction inside the unwanted cell;
    iii. cleaved by a complement-dependent cleavage reaction; or
    iv. cleaved by a protease that is colocalized to the unwanted cell by a targeting moiety that is the same or different from the targeting moiety in the agent,
wherein cleavage of the cleavage site causes loss of the inert binding partner and complementation with the first T-cell engaging domain of the two-component system.

Item 4. The two-component system of any one of items 1-3, wherein the first and the second targeting moieties are the same.

Item 5. The two-component system of any one of items 1-3, wherein the first and the second targeting moieties are different.

Item 6. The two-component system of any one of items 1-5, wherein the first and second cleavage site are the same.

Item 7. The two-component system of any one of items 1-5, wherein the first and second cleavage site are different.

Item 8. The two-component system of any one of items 1-7, wherein at least one cleavage site is a protease cleavage site.

Item 9. The two-component system of any one of items 1-8, wherein at least one cleavage site is capable of being cleaved outside the unwanted cells.

Item 10. The two-component system of any one of items 1-9, wherein at least one enzyme expressed by the unwanted cells is a protease.

Item 11. The two-component system of any one of items 1-10, wherein at least one inert binding partner specifically binds the T-cell engaging domain.

Item 12. The two-component system of any one of items 1-11, wherein at least one inert binding partner is a VH or VL domain.

Item 13. The two-component system of any one of items 1-12, wherein
- a. when the T-cell engaging domain is a VH domain, the inert binding partner is a VL domain and
- b. when the T-cell engaging domain is VL domain, the inert binding partner is a VH domain.

Item 14. The two-component system of any one of items 1-13, wherein at least one targeting moiety is an antibody or functional fragment thereof.

Item 15. The two-component system of any one of items 1-14, wherein the at least one inert binding partner is capable of dissociation once at least one cleavage site has been cleaved and after dissociation the two T-cell engaging domains are capable of binding to each other and exhibiting T-cell engaging activity.

Item 16. The two-component system of item 1-15, wherein one T-cell engaging domain is a VH domain and the other T-cell engaging domain is a VL domain.

Item 17. A component for use in a two-component system for treating a condition characterized by the presence of unwanted cells comprising a first targeted T-cell engaging agent comprising:
- a. a targeting moiety that is capable of targeting the unwanted cells;
- b. a first T-cell engaging domain capable of T-cell engaging activity when binding a second T-cell engaging domain, wherein the second T-cell engaging domain is not part of the first targeted T-cell engaging agent;
- c. an inert binding partner for the first T-cell engaging domain binding to the first T-cell engaging domain such that the first T-cell engaging domain does not bind to the second T-cell engaging domain unless the inert binding partner is removed; and
- d. a cleavage site separating the first T-cell engaging domain and the inert binding partner, wherein the cleavage site is:
  - i. cleaved by an enzyme expressed by the unwanted cells;
  - ii. cleaved through a pH-sensitive cleavage reaction inside the unwanted cell;
  - iii. cleaved by a complement-dependent cleavage reaction; or
  - iv. cleaved by a protease that is colocalized to the unwanted cell by a targeting moiety that is the same or different from the targeting moiety in the agent, wherein cleavage of the cleavage site causes loss of the inert binding partner and allows for complementation with the second T-cell engaging domain that is not part of the agent.

Item 18. The component for use in a two-component system of item 17, wherein the cleavage site is a protease cleavage site.

Item 19. The component for use in a two-component system of any one of items 17-18, wherein the cleavage site is capable of being cleaved outside the unwanted cells.

Item 20. The component for use in a two-component system of any one of items 17-19, wherein the enzyme expressed by the unwanted cells is a protease.

Item 21. The component for use in a two-component system of any one of items 17-20, wherein at least one inert binding partner specifically binds the T-cell engaging domain.

Item 22. The component for use in a two-component system of any one of items 17-21, wherein the inert binding partner is a VH or VL domain.

Item 23. The component for use in a two-component system of any one of items 17-22, wherein
- a. when the T-cell engaging domain is a VH domain, the inert binding partner is a VL domain and
- b. when the T-cell engaging domain is VL domain, the inert binding partner is a VH domain.

Item 24. The component for use in a two-component system of any one of items 17-23, wherein the targeting moiety is an antibody or functional fragment thereof.

Item 25. A set of nucleic acid molecules encoding the first and second component of the two component system of any one of items 1-16.

Item 26. A nucleic acid molecule encoding the component for use in a two-component system of any one of items 17-24.

Item 27. A method of treating a disease in a patient characterized by the presence of unwanted cells comprising administering the two-component system of any one of items 1-16 to the patient.

Item 28. A method of targeting an immune response of a patient to unwanted cells comprising administering the two-component system of any one of items 1-16 to the patient.

Item 29. The method of any one of items 27-28, wherein the unwanted cells are cancer cells.

Item 30. The method of item 29, wherein the cancer is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A kit or composition for treating cancer in a patient comprising:
   a. a first component comprising a targeted T-cell binding agent comprising:
      i. a first targeting moiety that is an antibody or antigen binding fragment thereof that binds a tumor antigen expressed by the cancer;
      ii. a first T-cell binding domain capable of T-cell binding activity when binding a second T-cell binding domain, wherein the second T-cell binding domain is not part of the first component, and wherein the first T-cell binding domain is either a VH domain or VL domain;
      iii. a first inert binding partner for the first T-cell binding domain binding to the first T-cell binding domain such that the first T-cell binding domain does not bind to the second T-cell binding domain unless the inert binding partner is removed, wherein if the first T-cell binding domain is a VH domain, the inert binding partner is a VL domain and if the first T-cell binding domain is a VL domain, the inert binding partner is a VH domain; and
      iv. a protease cleavage site separating the first T-cell binding domain and the first inert binding partner, wherein the protease cleavage site is capable of releasing the inert binding domain from the T-cell binding domain in the presence of a protease:
         (1) expressed by the cancer;
         (2) colocalized to the cancer by a targeting moiety that is an antibody or antigen binding fragment thereof that binds a tumor antigen expressed by the cancer and that is the same or different from the targeting moiety in the agent,
   a second component comprising a second T-cell binding domain capable of T-cell binding activity when binding the first T-cell binding domain, wherein the first and second T-cell binding domains are capable of binding CD3 or the T cell receptor (TCR) when neither is bound to an inert binding partner, and further wherein if the first T-cell binding domain is a VH domain, the second T-cell binding domain is a VL domain and if the first T-cell binding domain is a VL domain, the second T-cell binding domain is a VH domain.

2. The kit or composition of claim 1, wherein the second component further comprises a second targeting moiety that is an antibody or antigen binding fragment thereof that binds a tumor antigen expressed by the cancer.

3. The kit or composition of claim 2, wherein the second component further comprises a second inert binding partner for the second T-cell binding domain binding to the second T-cell binding domain such that the second T cell binding domain does not bind to the first T-cell binding domain unless the inert binding partner is removed, wherein if the second T-cell binding domain is a VH domain, the inert binding partner is a VL domain and if the second T-cell binding domain is a VL domain, the inert binding partner is a VH domain and
   a. a protease cleavage site separating the second T-cell binding domain and the second inert binding partner, wherein the protease cleavage site is
      (i) cleaved by a protease expressed by the cancer
      (ii) cleaved by a protease that is colocalized to the cancer by a targeting moiety that is an antibody or antigen binding fragment thereof that binds a tumor antigen expressed by the cancer and that is the same or different from the targeting moiety in the agent,
   wherein cleavage of the protease cleavage site causes loss of the inert binding partner and complementation with the first T-cell binding domain of the kit or composition.

4. The kit or composition of claim 3, wherein the first and the second targeting moieties are different.

5. The kit or composition of claim 3, wherein the protease cleavage sites of the first component and second component are different.

6. The kit or composition of claim 3, wherein the protease cleavage sites of the first component and second component are cleaved by a protease expressed by the cancer.

7. The kit or composition of claim 3, wherein the protease cleavage sites of the first component and/or second component are cleaved by a protease that is colocalized to the cancer by a targeting moiety that is an antibody or antigen binding fragment thereof that binds a tumor antigen expressed by the cancer and that is the same or different from the targeting moiety in the agent.

8. The kit or composition of claim 3, wherein each inert binding partner is capable of dissociation once at least one protease cleavage site for each inert binding partner has been cleaved and after dissociation the two T-cell binding domains are capable of binding to each other and exhibiting T-cell binding activity.

9. A component for use in a kit or composition for treating cancer in a patient comprising a first targeted T-cell binding agent comprising:

a. a targeting moiety that is an antibody or antigen binding fragment thereof that binds a tumor antigen expressed by the cancer;
b. a first T-cell binding domain capable of T-cell binding activity when binding a second T-cell binding domain, wherein the second T-cell binding domain is not part of the first targeted T-cell binding agent, and wherein the first T-cell binding domain is either a VH domain or VL domain and wherein the first T-cell binding domain and the second T-cell binding domain are capable of binding CD3 or TCR;
c. an inert binding partner for the first T-cell binding domain binding to the first T-cell binding domain such that the first T-cell binding domain does not bind to the second T-cell binding domain unless the inert binding partner is removed, wherein if the first T-cell binding domain is a VH domain, the inert binding partner is a VL domain and if the first T-cell binding domain is a VL domain, the inert binding partner is a VH domain; and a protease cleavage site separating the first T-cell binding domain and the inert binding partner, wherein the cleavage site is cleaved by a protease that is colocalized to the cancer by a targeting moiety that is an antibody or antigen binding fragment thereof that binds a tumor antigen expressed by the cancer and that is the same or different from the targeting moiety in the agent, wherein cleavage of the protease cleavage site causes loss of the inert binding partner and allows for complementation with the second T-cell binding domain that is not part of the agent, further wherein if the first T-cell binding domain is a VH domain, the second T-cell binding domain is a VL domain and if the first T-cell binding domain is a VL domain, the second T-cell binding domain is a VH domain.

10. A set of nucleic acid molecules encoding the first and second components of the kit or composition of claim 1.

11. A nucleic acid molecule encoding the first targeted T-cell binding agent of claim 9.

12. A method of treating cancer expressing a tumor antigen that binds the first targeting moiety in a patient comprising administering the composition of claim 1 to the patient.

13. A method of treating cancer expressing a tumor antigen that binds the first targeting moiety in a patient comprising administering the composition of claim 3 to the patient.

14. The method of claim 13, wherein the cancer expressing a tumor antigen that binds the first targeting moiety is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

15. A method of targeting T cells expressing CD3 or TCR to cancer expressing a tumor antigen that binds the first targeting moiety in a patient comprising administering the composition of claim 3 to the patient.

16. The kit or composition of claim 1, wherein the first and second T-cell binding domains are capable of forming an scFv when not bound to an inert binding domain.

* * * * *

SEQUENCE LISTING

<160> NUMBER OF SEQ ID NOS: 178

<210> SEQ ID NO 1
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 1

Lys Pro Ala Lys Phe Phe Arg Leu
1               5

<210> SEQ ID NO 2
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 2

Asp Pro Ala Lys Phe Phe Arg Leu
1               5

<210> SEQ ID NO 3
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 3

Lys Pro Met Lys Phe Phe Arg Leu
1               5

<210> SEQ ID NO 4
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 4

Leu Pro Ala Lys Phe Phe Arg Leu
1               5

<210> SEQ ID NO 5
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 5

Leu Pro Met Lys Phe Phe Arg Leu
1               5

<210> SEQ ID NO 6
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 6

Lys Pro Ala Met Phe Phe Arg Leu
1               5

```
<210> SEQ ID NO 7
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 7

Tyr Pro Ala Lys Phe Phe Arg Leu
1               5

<210> SEQ ID NO 8
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 8

Lys Trp Ala Lys Phe Phe Arg Leu
1               5

<210> SEQ ID NO 9
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 9

Asp Pro Met Lys Phe Phe Arg Leu
1               5

<210> SEQ ID NO 10
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 10

Asp Pro Ala Met Phe Phe Arg Leu
1               5

<210> SEQ ID NO 11
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 11

Asp Pro Met Met Phe Phe Arg Leu
1               5

<210> SEQ ID NO 12
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 12

Lys Met Ala Met Phe Phe Arg Leu
1               5
```

<210> SEQ ID NO 13
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 13

Lys Met Ala Met Phe Phe Ile Met
1               5

<210> SEQ ID NO 14
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 14

Lys Pro Ala Met Phe Phe Ile Met
1               5

<210> SEQ ID NO 15
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 15

Leu Pro Ala Met Phe Phe Arg Leu
1               5

<210> SEQ ID NO 16
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 16

Leu Pro Met Met Phe Phe Arg Leu
1               5

<210> SEQ ID NO 17
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 17

Leu Met Ala Met Phe Phe Arg Leu
1               5

<210> SEQ ID NO 18
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 18

Leu Met Ala Met Phe Phe Ile Met
1               5

```
<210> SEQ ID NO 19
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 19

Leu Pro Ala Met Phe Phe Ile Met
1               5

<210> SEQ ID NO 20
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 20

Leu Pro Ala Met Phe Phe Tyr Met
1               5

<210> SEQ ID NO 21
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 21

Lys Pro Met Met Phe Phe Arg Leu
1               5

<210> SEQ ID NO 22
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 22

Lys Pro Ala Lys Phe Phe Tyr Met
1               5

<210> SEQ ID NO 23
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 23

Lys Pro Ala Lys Phe Phe Ile Met
1               5

<210> SEQ ID NO 24
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 24

Ile Pro Met Lys Phe Phe Arg Leu
1               5

<210> SEQ ID NO 25
```

```
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 25

Ile Pro Ala Met Phe Phe Arg Leu
1               5

<210> SEQ ID NO 26
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 26

Ile Pro Met Met Phe Phe Arg Leu
1               5

<210> SEQ ID NO 27
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 27

Ile Met Ala Met Phe Phe Arg Leu
1               5

<210> SEQ ID NO 28
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 28

Ile Met Ala Met Phe Phe Ile Met
1               5

<210> SEQ ID NO 29
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 29

Ile Pro Ala Met Phe Phe Ile Met
1               5

<210> SEQ ID NO 30
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 30

Ile Pro Ala Met Phe Phe Tyr Met
1               5

<210> SEQ ID NO 31
<211> LENGTH: 2
```

```
<212> TYPE: PRT
<213> ORGANISM: Artificial Sequence
<220> FEATURE:
<223> OTHER INFORMATION: cathepsin B cleavage site

<400> SEQUENCE: 31

Phe Arg
1

<210> SEQ ID NO 32
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 32

Phe Lys
1

<210> SEQ ID NO 33
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 33

Val Ala
1

<210> SEQ ID NO 34
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 34

Val Arg
1

<210> SEQ ID NO 35
<211> LENGTH: 2
<212> TYPE: PRT
<213> ORGANISM: Artificial Sequence
<220> FEATURE:
<223> OTHER INFORMATION: cathepsin B cleavage site
<220> FEATURE:
<221> NAME/KEY: MISC_FEATURE
<222> LOCATION: (2)..(2)
<223> OTHER INFORMATION: X = {Cit}

<400> SEQUENCE: 35

Val Xaa
1

<210> SEQ ID NO 36
<211> LENGTH: 8
<212> TYPE: PRT
<213> ORGANISM: Artificial Sequence
<220> FEATURE:
<223> OTHER INFORMATION: cathepsin B cleavage site

<400> SEQUENCE: 36

His Leu Val Glu Ala Leu Tyr Leu
1               5
```

```
<210> SEQ ID NO 37
<211> LENGTH: 12
<212> TYPE: PRT
<213> ORGANISM: Artificial Sequence
<220> FEATURE:
<223> OTHER INFORMATION: cathepsin B cleavage site

<400> SEQUENCE: 37

Ser Leu Leu Lys Ser Arg Met Val Pro Asn Phe Asn
1               5                   10

<210> SEQ ID NO 38
<211> LENGTH: 12
<212> TYPE: PRT
<213> ORGANISM: Artificial Sequence
<220> FEATURE:
<223> OTHER INFORMATION: cathepsin B cleavage site

<400> SEQUENCE: 38

Ser Leu Leu Ile Ala Arg Arg Met Pro Asn Phe Asn
1               5                   10

<210> SEQ ID NO 39
<211> LENGTH: 4
<212> TYPE: PRT
<213> ORGANISM: Artificial Sequence
<220> FEATURE:
<223> OTHER INFORMATION: cathepsin B cleavage site

<400> SEQUENCE: 39

Lys Lys Phe Ala
1

<210> SEQ ID NO 40
<211> LENGTH: 4
<212> TYPE: PRT
<213> ORGANISM: Artificial Sequence
<220> FEATURE:
<223> OTHER INFORMATION: cathepsin B cleavage site

<400> SEQUENCE: 40

Ala Phe Lys Lys
1

<210> SEQ ID NO 41
<211> LENGTH: 3
<212> TYPE: PRT
<213> ORGANISM: Artificial Sequence
<220> FEATURE:
<223> OTHER INFORMATION: cathepsin B cleavage site

<400> SEQUENCE: 41

Gln Gln Gln
1

<210> SEQ ID NO 42
<211> LENGTH: 9
<212> TYPE: PRT
<213> ORGANISM: Artificial Sequence
<220> FEATURE:
<223> OTHER INFORMATION: cathepsin D cleavage site

<400> SEQUENCE: 42

Pro Arg Ser Phe Phe Arg Leu Gly Lys
1               5
```

```
<210> SEQ ID NO 43
<211> LENGTH: 12
<212> TYPE: PRT
<213> ORGANISM: Artificial Sequence
<220> FEATURE:
<223> OTHER INFORMATION: cathepsin D cleavage site

<400> SEQUENCE: 43

Ser Gly Val Val Ile Ala Thr Val Ile Val Ile Thr
1               5                   10

<210> SEQ ID NO 44
<211> LENGTH: 3
<212> TYPE: PRT
<213> ORGANISM: Artificial Sequence
<220> FEATURE:
<223> OTHER INFORMATION: cathepsin K cleavage site

<400> SEQUENCE: 44

Gly Gly Pro
1

<210> SEQ ID NO 45
<211> LENGTH: 12
<212> TYPE: PRT
<213> ORGANISM: Artificial Sequence
<220> FEATURE:
<223> OTHER INFORMATION: MMP1 cleavage site

<400> SEQUENCE: 45

Ser Leu Gly Pro Gln Gly Ile Trp Gly Gln Phe Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: MMP2 cleavage site

<400> SEQUENCE: 46

Ala Ile Pro Val Ser Leu Arg
1               5

<210> SEQ ID NO 47
<211> LENGTH: 12
<212> TYPE: PRT
<213> ORGANISM: Artificial Sequence
<220> FEATURE:
<223> OTHER INFORMATION: MMP2 cleavage site

<400> SEQUENCE: 47

Ser Leu Pro Leu Gly Leu Trp Ala Pro Asn Phe Asn
1               5                   10

<210> SEQ ID NO 48
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 48

His Pro Val Gly Leu Leu Ala Arg
1               5

<210> SEQ ID NO 49
```

```
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 49

Gly Pro Leu Gly Val Arg Gly Lys
1               5

<210> SEQ ID NO 50
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 50

Gly Pro Leu Gly Leu Trp Ala Gln
1               5

<210> SEQ ID NO 51
<211> LENGTH: 8
<212> TYPE: PRT
<213> ORGANISM: Artificial Sequence
<220> FEATURE:
<223> OTHER INFORMATION: MMP3 cleavage site

<400> SEQUENCE: 51

Ser Thr Ala Val Ile Val Ser Ala
1               5

<210> SEQ ID NO 52
<211> LENGTH: 8
<212> TYPE: PRT
<213> ORGANISM: Artificial Sequence
<220> FEATURE:
<223> OTHER INFORMATION: MMP7 cleavage site

<400> SEQUENCE: 52

Gly Pro Leu Gly Leu Ala Arg Lys
1               5

<210> SEQ ID NO 53
<211> LENGTH: 8
<212> TYPE: PRT
<213> ORGANISM: Artificial Sequence
<220> FEATURE:
<223> OTHER INFORMATION: MMP7 cleavage site

<400> SEQUENCE: 53

Arg Pro Leu Ala Leu Trp Arg Ser
1               5

<210> SEQ ID NO 54
<211> LENGTH: 12
<212> TYPE: PRT
<213> ORGANISM: Artificial Sequence
<220> FEATURE:
<223> OTHER INFORMATION: MMP7 cleavage site

<400> SEQUENCE: 54

Ser Leu Arg Pro Leu Ala Leu Trp Arg Ser Phe Asn
1               5                   10

<210> SEQ ID NO 55
<211> LENGTH: 6
```

```
<212> TYPE: PRT
<213> ORGANISM: Artificial Sequence
<220> FEATURE:
<223> OTHER INFORMATION: MMP2/9 cleavage site

<400> SEQUENCE: 55

Gly Ile Leu Gly Val Pro
1               5

<210> SEQ ID NO 56
<211> LENGTH: 8
<212> TYPE: PRT
<213> ORGANISM: Artificial Sequence
<220> FEATURE:
<223> OTHER INFORMATION: MMP2/9 cleavage site

<400> SEQUENCE: 56

Gly Pro Leu Gly Ile Ala Gly Gln
1               5

<210> SEQ ID NO 57
<211> LENGTH: 8
<212> TYPE: PRT
<213> ORGANISM: Artificial Sequence
<220> FEATURE:
<223> OTHER INFORMATION: MMP9 cleavage site

<400> SEQUENCE: 57

Ala Val Arg Trp Leu Leu Thr Ala
1               5

<210> SEQ ID NO 58
<211> LENGTH: 7
<212> TYPE: PRT
<213> ORGANISM: Artificial Sequence
<220> FEATURE:
<223> OTHER INFORMATION: MMP9 cleavage site

<400> SEQUENCE: 58

Pro Leu Gly Leu Tyr Ala Leu
1               5

<210> SEQ ID NO 59
<211> LENGTH: 9
<212> TYPE: PRT
<213> ORGANISM: Artificial Sequence
<220> FEATURE:
<223> OTHER INFORMATION: MMP9 cleavage site

<400> SEQUENCE: 59

Gly Pro Gln Gly Ile Ala Gly Gln Arg
1               5

<210> SEQ ID NO 60
<211> LENGTH: 8
<212> TYPE: PRT
<213> ORGANISM: Artificial Sequence
<220> FEATURE:
<223> OTHER INFORMATION: MMP9 cleavage site

<400> SEQUENCE: 60

Lys Pro Val Ser Leu Ser Tyr Arg
1               5

<210> SEQ ID NO 61
<211> LENGTH: 8
<212> TYPE: PRT
```

<213> ORGANISM: Artificial Sequence
<220> FEATURE:
<223> OTHER INFORMATION: MMP11 cleavage site

<400> SEQUENCE: 61

Ala Ala Ala Thr Ser Ile Ala Met
1               5

<210> SEQ ID NO 62
<211> LENGTH: 8
<212> TYPE: PRT
<213> ORGANISM: Artificial Sequence
<220> FEATURE:
<223> OTHER INFORMATION: MMP11 cleavage site

<400> SEQUENCE: 62

Ala Ala Gly Ala Met Phe Leu Glu
1               5

<210> SEQ ID NO 63
<211> LENGTH: 12
<212> TYPE: PRT
<213> ORGANISM: Artificial Sequence
<220> FEATURE:
<223> OTHER INFORMATION: MMP13 cleavage site

<400> SEQUENCE: 63

Gly Pro Gln Gly Leu Ala Gly Gln Arg Gly Ile Val
1               5                   10

<210> SEQ ID NO 64
<211> LENGTH: 5
<212> TYPE: PRT
<213> ORGANISM: Artificial Sequence
<220> FEATURE:
<223> OTHER INFORMATION: MMP14 cleavage site

<400> SEQUENCE: 64

Pro Arg His Leu Arg
1               5

<210> SEQ ID NO 65
<211> LENGTH: 12
<212> TYPE: PRT
<213> ORGANISM: Artificial Sequence
<220> FEATURE:
<223> OTHER INFORMATION: MMP14 cleavage site

<400> SEQUENCE: 65

Pro Gln Gly Leu Leu Gly Ala Pro Gly Ile Leu Gly
1               5                   10

<210> SEQ ID NO 66
<211> LENGTH: 8
<212> TYPE: PRT
<213> ORGANISM: Artificial Sequence
<220> FEATURE:
<223> OTHER INFORMATION: MMP14 cleavage site

<400> SEQUENCE: 66

Pro Arg Ser Ala Lys Glu Leu Arg
1               5

<210> SEQ ID NO 67
<211> LENGTH: 6
<212> TYPE: PRT
<213> ORGANISM: Artificial Sequence

```
<220> FEATURE:
<223> OTHER INFORMATION: PSA / KLK3

<400> SEQUENCE: 67

His Ser Ser Lys Leu Gln
1               5

<210> SEQ ID NO 68
<211> LENGTH: 5
<212> TYPE: PRT
<213> ORGANISM: Artificial Sequence
<220> FEATURE:
<223> OTHER INFORMATION: PSA / KLK3

<400> SEQUENCE: 68

Ser Ser Lys Leu Gln
1               5

<210> SEQ ID NO 69
<211> LENGTH: 4
<212> TYPE: PRT
<213> ORGANISM: Artificial Sequence
<220> FEATURE:
<223> OTHER INFORMATION: KLK4

<400> SEQUENCE: 69

Arg Gln Gln Arg
1

<210> SEQ ID NO 70
<211> LENGTH: 3
<212> TYPE: PRT
<213> ORGANISM: Artificial Sequence
<220> FEATURE:
<223> OTHER INFORMATION: TMPRSS2

<400> SEQUENCE: 70

Gly Gly Arg
1

<210> SEQ ID NO 71
<211> LENGTH: 3
<212> TYPE: PRT
<213> ORGANISM: Artificial Sequence
<220> FEATURE:
<223> OTHER INFORMATION: Legumain

<400> SEQUENCE: 71

Ala Ala Asn
1

<210> SEQ ID NO 72
<211> LENGTH: 3
<212> TYPE: PRT
<213> ORGANISM: Artificial Sequence
<220> FEATURE:
<223> OTHER INFORMATION: ST14 (Matriptase)

<400> SEQUENCE: 72

Gln Ala Arg
1

<210> SEQ ID NO 73
<211> LENGTH: 8
<212> TYPE: PRT
<213> ORGANISM: Artificial Sequence
<220> FEATURE:
```

<223> OTHER INFORMATION: C1s cleavage site

<400> SEQUENCE: 73

Tyr Leu Gly Arg Ser Tyr Lys Val
1               5

<210> SEQ ID NO 74
<211> LENGTH: 6
<212> TYPE: PRT
<213> ORGANISM: Artificial Sequence
<220> FEATURE:
<223> OTHER INFORMATION: C1s cleavage site
<220> FEATURE:
<221> NAME/KEY: misc_feature
<222> LOCATION: (6)..(6)
<223> OTHER INFORMATION: Xaa can be any naturally occurring amino acid

<400> SEQUENCE: 74

Met Gln Leu Gly Arg Xaa
1               5

<210> SEQ ID NO 75
<211> LENGTH: 8
<212> TYPE: PRT
<213> ORGANISM: Artificial Sequence
<220> FEATURE:
<223> OTHER INFORMATION: MASP2 cleavage site

<400> SEQUENCE: 75

Ser Leu Gly Arg Lys Ile Gln Ile
1               5

<210> SEQ ID NO 76
<211> LENGTH: 9
<212> TYPE: PRT
<213> ORGANISM: Artificial Sequence
<220> FEATURE:
<223> OTHER INFORMATION: C2a and Bb cleavage site

<400> SEQUENCE: 76

Gly Leu Ala Arg Ser Asn Leu Asp Glu
1               5

<210> SEQ ID NO 77
<211> LENGTH: 8
<212> TYPE: PRT
<213> ORGANISM: Artificial Sequence
<220> FEATURE:
<223> OTHER INFORMATION: uPa cleavage site

<400> SEQUENCE: 77

Thr Tyr Ser Arg Ser Arg Tyr Leu
1               5

<210> SEQ ID NO 78
<211> LENGTH: 12
<212> TYPE: PRT
<213> ORGANISM: Artificial Sequence
<220> FEATURE:
<223> OTHER INFORMATION: uPa cleavage site

<400> SEQUENCE: 78

Lys Lys Ser Pro Gly Arg Val Val Gly Gly Ser Val
1               5                   10

<210> SEQ ID NO 79
<211> LENGTH: 8

-continued

<212> TYPE: PRT
<213> ORGANISM: Artificial Sequence
<220> FEATURE:
<223> OTHER INFORMATION: uPa cleavage site

<400> SEQUENCE: 79

Asn Ser Gly Arg Ala Val Thr Tyr
1               5

<210> SEQ ID NO 80
<211> LENGTH: 3
<212> TYPE: PRT
<213> ORGANISM: Artificial Sequence
<220> FEATURE:
<223> OTHER INFORMATION: uPa cleavage site

<400> SEQUENCE: 80

Ala Phe Lys
1

<210> SEQ ID NO 81
<211> LENGTH: 12
<212> TYPE: PRT
<213> ORGANISM: Artificial Sequence
<220> FEATURE:
<223> OTHER INFORMATION: tissue-type plasminogen activator (tPA)

<400> SEQUENCE: 81

Gly Gly Ser Gly Gln Arg Gly Arg Lys Ala Leu Glu
1               5                   10

<210> SEQ ID NO 82
<211> LENGTH: 10
<212> TYPE: PRT
<213> ORGANISM: Artificial Sequence
<220> FEATURE:
<223> OTHER INFORMATION: ADAM10

<400> SEQUENCE: 82

Pro Arg Tyr Glu Ala Tyr Lys Met Gly Lys
1               5                   10

<210> SEQ ID NO 83
<211> LENGTH: 5
<212> TYPE: PRT
<213> ORGANISM: Artificial Sequence
<220> FEATURE:
<223> OTHER INFORMATION: ADAM12

<400> SEQUENCE: 83

Leu Ala Gln Ala Phe
1               5

<210> SEQ ID NO 84
<211> LENGTH: 11
<212> TYPE: PRT
<213> ORGANISM: Artificial Sequence
<220> FEATURE:
<223> OTHER INFORMATION: ADAM17

<400> SEQUENCE: 84

Glu His Ala Asp Leu Leu Ala Val Val Ala Lys
1               5                   10

<210> SEQ ID NO 85
<211> LENGTH: 5
<212> TYPE: PRT

```
<213> ORGANISM: Artificial Sequence
<220> FEATURE:
<223> OTHER INFORMATION: flexible amino acid linker (may be presented
      in repeating fashion)

<400> SEQUENCE: 85

Gly Gly Gly Gly Ser
1               5

<210> SEQ ID NO 86
<211> LENGTH: 4
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 86

Gly Gly Gly Ser
1

<210> SEQ ID NO 87
<211> LENGTH: 2
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 87

Gly Ser
1

<210> SEQ ID NO 88
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 88

Gly Ser Gly Gly Ser
1               5

<210> SEQ ID NO 89
<211> LENGTH: 4
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 89

Gly Gly Ser Gly
1

<210> SEQ ID NO 90
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 90

Gly Gly Ser Gly Gly
1               5
```

<210> SEQ ID NO 91
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 91

Gly Ser Gly Ser Gly
1               5

<210> SEQ ID NO 92
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 92

Gly Ser Gly Gly Gly
1               5

<210> SEQ ID NO 93
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 93

Gly Gly Gly Ser Gly
1               5

<210> SEQ ID NO 94
<211> LENGTH: 5
<212> TYPE: PRT
<213> ORGANISM: Artificial Sequence
<220> FEATURE:
<223> OTHER INFORMATION: flexible amino acid linker (may be presented
      in repeating fashion)

<400> SEQUENCE: 94

Gly Ser Ser Ser Gly
1               5

<210> SEQ ID NO 95
<211> LENGTH: 51
<212> TYPE: RNA
<213> ORGANISM: Artificial Sequence
<220> FEATURE:
<223> OTHER INFORMATION: Anti-EGFR aptamer (tight binder with Kd=2.4 nM)

<400> SEQUENCE: 95
ugccgcuaua augcacggau uuaaucgccg uagaaaagca ugucaaagcc g          51

<210> SEQ ID NO 96
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 96
uggcgcuaaa uagcacggaa auaaucgccg uagaaaagca ugucaaagcc g     51

<210> SEQ ID NO 97
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 97
ugcuaguaua ucgcacggau uuaaucgccg uagaaaagca ugucaaagcc g     51

<210> SEQ ID NO 98
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 98
ugccgccaua ucacacggau uuaaucgccg uagaaaagca ugucaaagcc g     51

<210> SEQ ID NO 99
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 99
uuccgcugua uaacacggac uuaaucgccg uaguaaagca ugucaaagcc g     51

<210> SEQ ID NO 100
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 100
ugucgcucua uugcacggau uuaaucgccg uagaaaagca ugucaaagcc g     51

<210> SEQ ID NO 101
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 101
ugcugcuuua ucccacauau uuuuccccu cauaacaaua uuucucccccc c     51

<210> SEQ ID NO 102
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature

```
<222> LOCATION: (45)..(45)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u

<400> SEQUENCE: 102
ugcngcuaua ucgcncguau uuaaucgccg uagaaaagca ugucnangcc g          51

<210> SEQ ID NO 103
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 103
ugcaaagaaa acgcacguau uuaaucgccg uaguaaagca ugucaaagcc g          51

<210> SEQ ID NO 104
<211> LENGTH: 53
<212> TYPE: RNA
<213> ORGANISM: Artificial Sequence
<220> FEATURE:
<223> OTHER INFORMATION: Anti-EGFR aptamer

<400> SEQUENCE: 104
ugcaucacua ucgaaccuau uuaauccacc aaaauaauug caaguccaua cuc        53

<210> SEQ ID NO 105
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (5)..(6)
<223> OTHER INFORMATION: n is a, c, g, or u
<220> FEATURE:
<221> NAME/KEY: misc_feature
<222> LOCATION: (17)..(17)
<223> OTHER INFORMATION: n is a, c, g, or u
<220> FEATURE:
<221> NAME/KEY: misc_feature
<222> LOCATION: (48)..(48)
<223> OTHER INFORMATION: n is a, c, g, or u

<400> SEQUENCE: 105
ugccnnaaua acacacnuau auaaucgccg uacaaaauca ugucaaancc g          51

<210> SEQ ID NO 106
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 106
ugcagcugua uugcacguau uuaaucgccg uagaaaagca ugucaaagcc g          51

<210> SEQ ID NO 107
<211> LENGTH: 50
<212> TYPE: RNA
<213> ORGANISM: Artificial Sequence
<220> FEATURE:
<223> OTHER INFORMATION: Anti-EGFR aptamer
```

<400> SEQUENCE: 107
uuccgauaau cccgcguacu aaaucaccau agucaacaau uuccaaccuc                50

<210> SEQ ID NO 108
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 108
uccacuauau cacacguauu uaaucgccgu agaaaagcau gucaaagccg                50

<210> SEQ ID NO 109
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 109
ucccucaacc ucgcuacuau uuaaucgccg uagaaaagca ugucaaagcc u              51

<210> SEQ ID NO 110
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 110
ugccgcuaua ucacacgaau uuaaucgccg uagaaaagca ugucaaagcc g              51

<210> SEQ ID NO 111
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 111
agccccuaga acacacggau uuaaucgccg uagaaaagca ugucaaagcc g              51

<210> SEQ ID NO 112
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 112
ugccaauaua uaacacggaa uuaaucgccg uagaaaagca ugucaaagcc g              51

<210> SEQ ID NO 113
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 113
ugccgcuaua gcgcacggau uuaaucgccg uagaaaagca ugucaaagcc g              51

<210> SEQ ID NO 114
<211> LENGTH: 50

```
<212> TYPE: RNA
<213> ORGANISM: Artificial Sequence
<220> FEATURE:
<223> OTHER INFORMATION: Anti-EGFR aptamer

<400> SEQUENCE: 114
ugcagauaua ugucacucau uaaucccgu auaaaaacau aacuaagcuc                50

<210> SEQ ID NO 115
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 115
uguagcugua uugcacacau uaaaucgccg uaguaaagca ugucaaagcc g             51

<210> SEQ ID NO 116
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 116
uaccaauaua ucgccacaca uaaucgccgu agaaaagcau gucaaagccg              50

<210> SEQ ID NO 117
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 117
ugccgcuaug cccacggaau uuaaucgccg uagaaaaaca gucaaaguc g              51

<210> SEQ ID NO 118
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 118
ugccgcuauu uagcacggau uaaaucgccg uagaaaagca gucaaagcc g              51

<210> SEQ ID NO 119
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (45)..(45)
<223> OTHER INFORMATION: n is a, c, g, or u

<400> SEQUENCE: 119
ugccgcuauu uagcacggau uaaaucgccg uagaaaagca gucnaagcc g              51

<210> SEQ ID NO 120
<211> LENGTH: 51
<212> TYPE: RNA
<213> ORGANISM: Artificial Sequence
<220> FEATURE:
```

```
<223> OTHER INFORMATION: Anti-EGFR aptamer
<220> FEATURE:
<221> NAME/KEY: misc_feature
<222> LOCATION: (41)..(41)
<223> OTHER INFORMATION: n is a, c, g, or u

<400> SEQUENCE: 120
uguaguaaua ugacacggau uuaaucgccg uagaaaagca ngucaaagcc u          51

<210> SEQ ID NO 121
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 121
ugucgccauu acgcacggau uuaaucgccg uagaaaagca ugucaaagcc g          51

<210> SEQ ID NO 122
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 122
ugcccccaaa cuacacaaau uuaaucgccg uauaaaagca ugucaaagcc g          51

<210> SEQ ID NO 123
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 123
ugcacuaucu cacacguacu aaucgccgua uaaaagcaug ucaaagccg            49

<210> SEQ ID NO 124
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 124
ugucgcaaua auacacuaau uuaaucgccg uagaaaagca ugucaaagcc g          51

<210> SEQ ID NO 125
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 125
ugcaacaaua uagcacguau uuaaucgccg uaguaaagca ugucaaagg            49

<210> SEQ ID NO 126
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 126
```

```
cuaccacaaa ucccacauau uuaaucuccc aaucaaaucu uguccauucc c         51
```

<210> SEQ ID NO 127
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 127

```
ugcccuaaac ucacacggau auaaucgccg uagaaaagca ugucaaagcc g         51
```

<210> SEQ ID NO 128
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 128

```
uugucguaug ucacacguau uaaaucgccg uauaaaagca ugucaaagcc g         51
```

<210> SEQ ID NO 129
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 129

```
uuccgcuaua acacacggag aaaaucgccg uaguaaagca ugucaaagcc g         51
```

<210> SEQ ID NO 130
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 130

```
ugccgauaua acgcacggau auaaucgccg uagaaaagca ugucaaagcc g         51
```

<210> SEQ ID NO 131
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 131

```
ugccauuaua cagcacggau uuaaucgccg uagaaaagca ugucaaagcc g         51
```

<210> SEQ ID NO 132
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 132

```
uccagaaaua ugcacacauu uaaucgccgu agaaaagcau gucaaagccg          50
```

<210> SEQ ID NO 133
<211> LENGTH: 50
<212> TYPE: RNA

```
<213> ORGANISM: Artificial Sequence
<220> FEATURE:
<223> OTHER INFORMATION: Anti-EGFR aptamer

<400> SEQUENCE: 133
uccgcuaaac aacacggaua caaucgccgu agaaaagcau guccaagccg        50

<210> SEQ ID NO 134
<211> LENGTH: 49
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (46)..(48)
<223> OTHER INFORMATION: n is a, c, g, or u

<400> SEQUENCE: 134
ugcacuaucu cacacguacu aaucgccgua uaaaagcaug ucaaannng         49

<210> SEQ ID NO 135
<211> LENGTH: 50
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (8)..(10)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u

<400> SEQUENCE: 135
aungcnannn uacacguauu naaucgccgu agaaaagcau gucanagccg        50

<210> SEQ ID NO 136
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 136
ugcugcuaua uugcaauuuu uuaaacuaag uagaaaacca guacaaguc g       51

<210> SEQ ID NO 137
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 137
ugucgccaua uugcacggau uuaaucgccg uagaaaagca guccaagcc g       51
```

<210> SEQ ID NO 138
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 138
ugccguuaua acccacggaa uuuaaccucc guagaaaagc augucaaagc cg    52

<210> SEQ ID NO 139
<211> LENGTH: 52
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (40)..(40)
<223> OTHER INFORMATION: n is a, c, g, or u

<400> SEQUENCE: 139
ugugaauaua uaucacggau uuaaucgccg uauaaaagcn augucaaagc cg    52

<210> SEQ ID NO 140
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (10)..(11)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u

<400> SEQUENCE: 140
ugccgauaun nancacggau uuaaucgccg uagaaaagca uguccaagcc g    51

<210> SEQ ID NO 141
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 141
ugucacuaaa uugcacguau auaaucgccg uaguaagcau gucaaagccg    50

<210> SEQ ID NO 142
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 142
ugcaaccaua aagcacguaa uaaaucgccg uauauaagca gucaaagcc g    51

<210> SEQ ID NO 143
<211> LENGTH: 50
<212> TYPE: RNA
<213> ORGANISM: Artificial Sequence
<220> FEATURE:

```
<223> OTHER INFORMATION: Anti-EGFR aptamer

<400> SEQUENCE: 143
ugccgcuaua uagcacguau uaaucgccgu aguaaagcau gucaaagccg          50

<210> SEQ ID NO 144
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 144
ugccgcuaua gcacacggaa uuuaaucgcc guaguaaagc augucaaagc cg       52

<210> SEQ ID NO 145
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u

<400> SEQUENCE: 145
ugcagguaua uaacncggau uuaaucgccg uagaaaagca ugucnaagcc g        51

<210> SEQ ID NO 146
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 146
ugcuccuaua acacacggau uuaaucgccg uagaaaagca uguccaagcc g        51

<210> SEQ ID NO 147
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 147
ugcccguaau ugcacggauu uaaucgccgu agaaaagcau guccaagccg g        51

<210> SEQ ID NO 148
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: misc_feature
<222> LOCATION: (44)..(44)
<223> OTHER INFORMATION: n is a, c, g, or u

<400> SEQUENCE: 148
```
acucccuaua ungcaacuac auaaucgccg uaaauaagca uguncaagcc g        51

<210> SEQ ID NO 149
<211> LENGTH: 54
<212> TYPE: RNA
<213> ORGANISM: Artificial Sequence
<220> FEATURE:
<223> OTHER INFORMATION: Anti-EGFR aptamer

<400> SEQUENCE: 149
ugaagcuaga ucacacuaaa uuaaucgccg uagaaaagca ugucaaaaaa gccg    54

<210> SEQ ID NO 150
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 150
ugacucuuua uccccceguac auuauucacc gaaccaaagc auuaccaucc cc      52

<210> SEQ ID NO 151
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 151
ugacgcccua acacacguau auaaucgccg uagaaaagca ugucaaagcc g        51

<210> SEQ ID NO 152
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 152
ugucgcaaaa uagcacguau uuaaucgccg uagaaaagca uguccaagcc g        51

<210> SEQ ID NO 153
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 153
ugaguguaua auucacguau uuaaucgccg uagaaaagca ugucaaagcc g        51

<210> SEQ ID NO 154
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 154
ugcuacuaua ucguagguaa cuaaucgccc uacaaacuca cucuaaaacc g        51

<210> SEQ ID NO 155
<211> LENGTH: 53
<212> TYPE: RNA

-continued

```
<213> ORGANISM: Artificial Sequence
<220> FEATURE:
<223> OTHER INFORMATION: Anti-EGFR aptamer

<400> SEQUENCE: 155
uuacgcuaua ucacacggaa uuuuaaucgc cguagaaaag cauguccaag ccg          53

<210> SEQ ID NO 156
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 156
cccaucugua cuacaggaau uuaaucgccg uagaaaagca uguccaagcc g             51

<210> SEQ ID NO 157
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 157
ugcccauaaa uagcacggau uuaaucgccg uagaaaagca uguccaagcc g             51

<210> SEQ ID NO 158
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 158
ugccgcaaua acauacacau auaaucgccg uagaaaagca ugucaaagcc g             51

<210> SEQ ID NO 159
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 159
ugcaacuaua ucgcacguau guaaucgccg uagaaaaagc augucaaagc c             51

<210> SEQ ID NO 160
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 160
uuccgcuaua uagcacggaa uuaaucgccg uagaaaagca uguccaagcc g             51

<210> SEQ ID NO 161
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 161
uuccgcuaag ucacacgaaa uuaaucgccg uagaaaagca uguccaagcc g             51
```

<210> SEQ ID NO 162
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 162
uguagcaaua ucacacguaa uuaaucgccg uauauaagca gucaaagcc g      51

<210> SEQ ID NO 163
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 163
ugccguuaua uaucacggau uuaaucgccg uagaaaagca guccaagcc g      51

<210> SEQ ID NO 164
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 164
uaacacauau aucaaguaac uuaucuccuu aguaaccauc uccaagccg         49

<210> SEQ ID NO 165
<211> LENGTH: 502
<212> TYPE: PRT
<213> ORGANISM: Artificial Sequence
<220> FEATURE:
<223> OTHER INFORMATION: Construct

<400> SEQUENCE: 165

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Phe Glu Asp Ser Ala Val Tyr Phe
        210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Asp Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Arg Tyr Thr Met His
        275                 280                 285

Trp Val Arg Gln Ala Pro Gly Gln Gly Leu Glu Trp Ile Gly Tyr Ile
    290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
        355                 360                 365

Thr Val Ser Ser Gly Glu Gly Thr Ser Thr Gly Ser Gly Gly Ser Gly
    370                 375                 380

Gly Ser Gly Gly Ala Asp Asp Ile Val Leu Thr Gln Ser Pro Ala Thr
385                 390                 395                 400

Leu Ser Leu Ser Pro Gly Glu Arg Ala Thr Leu Ser Cys Arg Ala Ser
                405                 410                 415

Gln Ser Val Ser Tyr Met Asn Trp Tyr Gln Gln Lys Pro Gly Lys Ala
            420                 425                 430

Pro Lys Arg Trp Ile Tyr Asp Thr Ser Lys Val Ala Ser Gly Val Pro
        435                 440                 445

Ala Arg Phe Ser Gly Ser Gly Ser Gly Thr Asp Tyr Ser Leu Thr Ile
    450                 455                 460

Asn Ser Leu Glu Ala Glu Asp Ala Ala Thr Tyr Tyr Cys Gln Gln Trp
465                 470                 475                 480

Ser Ser Asn Pro Leu Thr Phe Gly Gly Gly Thr Lys Val Glu Ile Lys
                485                 490                 495

His His His His His His
            500

<210> SEQ ID NO 166
<211> LENGTH: 396
<212> TYPE: PRT
<213> ORGANISM: Artificial Sequence
<220> FEATURE:
<223> OTHER INFORMATION: Construct

<400> SEQUENCE: 166

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Gly Ser
            115                 120                 125

Glu Val Gln Leu Leu Glu Gln Ser Gly Ala Glu Leu Val Arg Pro Gly
130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Asp Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Arg Tyr Thr Met His
        275                 280                 285

Trp Val Arg Gln Ala Pro Gly Gln Gly Leu Glu Trp Ile Gly Tyr Ile
    290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
        355                 360                 365

Thr Val Ser Ser Gly Glu Gly Thr Ser Thr Gly Ser Gly Gly Ser Gly
    370                 375                 380

Gly Ser Gly Gly Ala Asp His His His His His
385                 390                 395

<210> SEQ ID NO 167
<211> LENGTH: 365
<212> TYPE: PRT
<213> ORGANISM: Artificial Sequence
<220> FEATURE:
<223> OTHER INFORMATION: Construct

<400> SEQUENCE: 167

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Asp Ile Val
                245                 250                 255

Leu Thr Gln Ser Pro Ala Thr Leu Ser Leu Ser Pro Gly Glu Arg Ala
            260                 265                 270

Thr Leu Ser Cys Arg Ala Ser Gln Ser Val Ser Tyr Met Asn Trp Tyr
        275                 280                 285

Gln Gln Lys Pro Gly Lys Ala Pro Lys Arg Trp Ile Tyr Asp Thr Ser
    290                 295                 300

Lys Val Ala Ser Gly Val Pro Ala Arg Phe Ser Gly Ser Gly Ser Gly
305                 310                 315                 320

Thr Asp Tyr Ser Leu Thr Ile Asn Ser Leu Glu Ala Glu Asp Ala Ala
                325                 330                 335

Thr Tyr Tyr Cys Gln Gln Trp Ser Ser Asn Pro Leu Thr Phe Gly Gly
            340                 345                 350

Gly Thr Lys Val Glu Ile Lys His His His His His
        355                 360                 365
```

<210> SEQ ID NO 168
<211> LENGTH: 511
<212> TYPE: PRT
<213> ORGANISM: Artificial Sequence
<220> FEATURE:
<223> OTHER INFORMATION: Construct

<400> SEQUENCE: 168

-continued

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Lys Pro Gly Gln
                35                  40                  45

Pro Pro Lys Leu Leu Ile Tyr Trp Ala Ser Thr Arg Glu Ser Gly Val
50                      55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys Gly Gly Gly Gly Ser Gly Gly Gly Gly Ser Gly Gly Gly Gly Ser
                115                 120                 125

Glu Val Gln Leu Leu Glu Gln Ser Gly Ala Glu Leu Val Arg Pro Gly
                130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
                180                 185                 190

Phe Lys Gly Lys Ala Thr Leu Thr Ala Asp Lys Ser Ser Ser Thr Ala
                195                 200                 205

Tyr Met Gln Leu Ser Ser Leu Thr Phe Glu Asp Ser Ala Val Tyr Phe
                210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Asp Val Gln
                245                 250                 255

Leu Val Gln Ser Gly Ala Glu Val Lys Lys Pro Gly Ala Ser Val Lys
                260                 265                 270

Val Ser Cys Lys Ala Ser Gly Tyr Thr Phe Thr Arg Tyr Thr Met His
                275                 280                 285

Trp Val Arg Gln Ala Pro Gly Gln Gly Leu Glu Trp Ile Gly Tyr Ile
                290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
                340                 345                 350

Tyr Asp Asp His Tyr Cys Leu Asp Tyr Trp Gly Gln Gly Thr Thr Val
                355                 360                 365

Thr Val Ser Ser Gly Glu Gly Thr Ser Thr Gly Ser Gly Ala Ile Pro
370                 375                 380

Val Ser Leu Arg Gly Ser Gly Ser Gly Gly Ala Asp Asp Ile Val
385                 390                 395                 400

Leu Thr Gln Ser Pro Ala Thr Leu Ser Leu Ser Pro Gly Glu Arg Ala
                405                 410                 415
```

```
Thr Leu Ser Cys Arg Ala Ser Gln Ser Val Ser Ser Tyr Leu Ala
            420                 425                 430

Trp Tyr Gln Gln Lys Pro Gly Gln Ala Pro Arg Leu Leu Ile Tyr Gly
        435                 440                 445

Ala Ser Ser Arg Ala Thr Gly Val Pro Ala Arg Phe Ser Gly Ser Gly
        450                 455                 460

Ser Gly Thr Asp Phe Thr Leu Thr Ile Ser Ser Leu Glu Pro Glu Asp
465                 470                 475                 480

Phe Ala Thr Tyr Tyr Cys Leu Gln Ile Tyr Asn Met Pro Ile Thr Phe
                485                 490                 495

Gly Gln Gly Thr Lys Val Glu Ile Lys His His His His His His
            500                 505                 510
```

<210> SEQ ID NO 169
<211> LENGTH: 508
<212> TYPE: PRT
<213> ORGANISM: Artificial Sequence
<220> FEATURE:
<223> OTHER INFORMATION: Construct

<400> SEQUENCE: 169

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys Gly Gly Gly Gly Ser Gly Gly Gly Gly Ser Gly Gly Gly Gly Ser
            115                 120                 125

Glu Val Gln Leu Leu Glu Gln Ser Gly Ala Glu Leu Val Arg Pro Gly
        130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
                180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Phe Glu Asp Ser Ala Val Tyr Phe
        210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Asp Ile Val
                245                 250                 255

Leu Thr Gln Ser Pro Ala Thr Leu Ser Leu Ser Pro Gly Glu Arg Ala
                260                 265                 270
```

```
Thr Leu Ser Cys Arg Ala Ser Gln Ser Val Ser Tyr Met Asn Trp Tyr
            275                 280                 285

Gln Gln Lys Pro Gly Lys Ala Pro Lys Arg Trp Ile Tyr Asp Thr Ser
        290                 295                 300

Lys Val Ala Ser Gly Val Pro Ala Arg Phe Ser Gly Ser Gly Ser Gly
305                 310                 315                 320

Thr Asp Tyr Ser Leu Thr Ile Asn Ser Leu Glu Ala Glu Asp Ala Ala
                325                 330                 335

Thr Tyr Tyr Cys Gln Gln Trp Ser Ser Asn Pro Leu Thr Phe Gly Gly
            340                 345                 350

Gly Thr Lys Val Glu Ile Lys Gly Glu Gly Thr Ser Thr Gly Ser Gly
        355                 360                 365

Ala Ile Pro Val Ser Leu Arg Gly Ser Gly Ser Gly Gly Ala Asp
    370                 375                 380

Asp Val Gln Leu Val Gln Ser Gly Ala Glu Val Lys Lys Pro Gly Ala
385                 390                 395                 400

Ser Val Lys Val Ser Cys Lys Ala Ser Gly Tyr Thr Phe Thr Gly Tyr
                405                 410                 415

Tyr Met His Trp Val Arg Gln Ala Pro Gly Gln Gly Leu Glu Trp Met
            420                 425                 430

Gly Trp Ile Asn Pro Asn Ser Gly Gly Thr Asn Tyr Ala Gln Lys Phe
        435                 440                 445

Gln Gly Arg Val Thr Ile Thr Arg Asp Thr Ser Ala Ser Thr Ala Tyr
        450                 455                 460

Met Glu Leu Ser Ser Leu Arg Ser Glu Asp Thr Ala Val Tyr Tyr Cys
465                 470                 475                 480

Ala Arg Asp Phe Leu Ser Gly Tyr Leu Asp Tyr Trp Gly Gln Gly Thr
                485                 490                 495

Leu Val Thr Val Ser Ser His His His His His His
            500                 505

<210> SEQ ID NO 170
<211> LENGTH: 511
<212> TYPE: PRT
<213> ORGANISM: Artificial Sequence
<220> FEATURE:
<223> OTHER INFORMATION: Construct

<400> SEQUENCE: 170

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125
```

Glu Val Gln Leu Leu Glu Gln Ser Gly Ala Glu Leu Val Arg Pro Gly
            130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
                195                 200                 205

Tyr Met Gln Leu Ser Ser Leu Thr Phe Glu Asp Ser Ala Val Tyr Phe
210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Asp Val Gln
                245                 250                 255

Leu Val Gln Ser Gly Ala Glu Val Lys Lys Pro Gly Ala Ser Val Lys
                260                 265                 270

Val Ser Cys Lys Ala Ser Gly Tyr Thr Phe Thr Arg Tyr Thr Met His
            275                 280                 285

Trp Val Arg Gln Ala Pro Gly Gln Gly Leu Glu Trp Ile Gly Tyr Ile
290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
                355                 360                 365

Thr Val Ser Ser Gly Glu Gly Thr Ser Thr Gly Ser Gly Gly Gly
370                 375                 380

Ser Gly Gly Gly Ser Gly Gly Ser Gly Ala Asp Asp Ile Val
385                 390                 395                 400

Leu Thr Gln Ser Pro Ala Thr Leu Ser Leu Ser Pro Gly Glu Arg Ala
                405                 410                 415

Thr Leu Ser Cys Arg Ala Ser Gln Ser Val Ser Ser Tyr Leu Ala
                420                 425                 430

Trp Tyr Gln Gln Lys Pro Gly Gln Ala Pro Arg Leu Leu Ile Tyr Gly
                435                 440                 445

Ala Ser Ser Arg Ala Thr Gly Val Pro Ala Arg Phe Ser Gly Ser Gly
450                 455                 460

Ser Gly Thr Asp Phe Thr Leu Thr Ile Ser Ser Leu Glu Pro Glu Asp
465                 470                 475                 480

Phe Ala Thr Tyr Tyr Cys Leu Gln Ile Tyr Asn Met Pro Ile Thr Phe
                485                 490                 495

Gly Gln Gly Thr Lys Val Glu Ile Lys His His His His His His
                500                 505                 510

<210> SEQ ID NO 171
<211> LENGTH: 508
<212> TYPE: PRT
<213> ORGANISM: Artificial Sequence
<220> FEATURE:
<223> OTHER INFORMATION: Construct

<400> SEQUENCE: 171

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Asp Ile Val
                245                 250                 255

Leu Thr Gln Ser Pro Ala Thr Leu Ser Leu Ser Pro Gly Glu Arg Ala
            260                 265                 270

Thr Leu Ser Cys Arg Ala Ser Gln Ser Val Ser Tyr Met Asn Trp Tyr
        275                 280                 285

Gln Gln Lys Pro Gly Lys Ala Pro Lys Arg Trp Ile Tyr Asp Thr Ser
290                 295                 300

Lys Val Ala Ser Gly Val Pro Ala Arg Phe Ser Gly Ser Gly Ser Gly
305                 310                 315                 320

Thr Asp Tyr Ser Leu Thr Ile Asn Ser Leu Glu Ala Glu Asp Ala Ala
                325                 330                 335

Thr Tyr Tyr Cys Gln Gln Trp Ser Ser Asn Pro Leu Thr Phe Gly Gly
            340                 345                 350

Gly Thr Lys Val Glu Ile Lys Gly Glu Gly Thr Ser Thr Gly Ser Gly
        355                 360                 365

Gly Gly Ser Gly Gly Gly Ser Gly Gly Gly Ser Gly Gly Ala Asp
                    370                 375                 380

Asp Val Gln Leu Val Gln Ser Gly Ala Glu Val Lys Lys Pro Gly Ala
385                 390                 395                 400

Ser Val Lys Val Ser Cys Lys Ala Ser Gly Tyr Thr Phe Thr Gly Tyr

```
                        405                 410                 415
Tyr Met His Trp Val Arg Gln Ala Pro Gly Gln Gly Leu Glu Trp Met
            420                 425                 430

Gly Trp Ile Asn Pro Asn Ser Gly Gly Thr Asn Tyr Ala Gln Lys Phe
            435                 440                 445

Gln Gly Arg Val Thr Ile Thr Arg Asp Thr Ser Ala Ser Thr Ala Tyr
    450                 455                 460

Met Glu Leu Ser Ser Leu Arg Ser Glu Asp Thr Ala Val Tyr Tyr Cys
465                 470                 475                 480

Ala Arg Asp Phe Leu Ser Gly Tyr Leu Asp Tyr Trp Gly Gln Gly Thr
                485                 490                 495

Leu Val Thr Val Ser Ser His His His His His His
            500                 505

<210> SEQ ID NO 172
<211> LENGTH: 380
<212> TYPE: PRT
<213> ORGANISM: Artificial Sequence
<220> FEATURE:
<223> OTHER INFORMATION: Construct

<400> SEQUENCE: 172

Gln Val Gln Leu Val Gln Ser Gly Gly Gly Leu Val Gln Pro Gly Gly
1               5                   10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Gly Gly Gly Gly Ser Asp Val Gln Leu Val Gln
        115                 120                 125

Ser Gly Ala Glu Val Lys Lys Pro Gly Ala Ser Val Lys Val Ser Cys
    130                 135                 140

Lys Ala Ser Gly Tyr Thr Phe Thr Arg Tyr Thr Met His Trp Val Arg
145                 150                 155                 160

Gln Ala Pro Gly Gln Gly Leu Glu Trp Ile Gly Tyr Ile Asn Pro Ser
                165                 170                 175

Arg Gly Tyr Thr Asn Tyr Ala Asp Ser Val Lys Gly Arg Phe Thr Ile
            180                 185                 190

Thr Thr Asp Lys Ser Thr Ser Thr Ala Tyr Met Glu Leu Ser Ser Leu
        195                 200                 205

Arg Ser Glu Asp Thr Ala Thr Tyr Tyr Cys Ala Arg Tyr Tyr Asp Asp
    210                 215                 220

His Tyr Cys Leu Asp Tyr Trp Gly Gln Gly Thr Thr Val Thr Val Ser
225                 230                 235                 240

Ser Gly Glu Gly Thr Ser Thr Gly Ser Gly Ala Ile Pro Val Ser Leu
                245                 250                 255

Arg Gly Ser Gly Gly Ser Gly Gly Ala Asp Asp Ile Val Leu Thr Gln
```

```
                260             265             270
Ser Pro Ala Thr Leu Ser Leu Ser Pro Gly Glu Arg Ala Thr Leu Ser
            275                 280                 285

Cys Arg Ala Ser Gln Ser Val Ser Ser Tyr Leu Ala Trp Tyr Gln
        290                 295                 300

Gln Lys Pro Gly Gln Ala Pro Arg Leu Leu Ile Tyr Gly Ala Ser Ser
305                 310                 315                 320

Arg Ala Thr Gly Val Pro Ala Arg Phe Ser Gly Ser Gly Ser Gly Thr
                325                 330                 335

Asp Phe Thr Leu Thr Ile Ser Ser Leu Glu Pro Glu Asp Phe Ala Thr
            340                 345                 350

Tyr Tyr Cys Leu Gln Ile Tyr Asn Met Pro Ile Thr Phe Gly Gln Gly
        355                 360                 365

Thr Lys Val Glu Ile Lys His His His His His His
    370                 375                 380

<210> SEQ ID NO 173
<211> LENGTH: 508
<212> TYPE: PRT
<213> ORGANISM: Artificial Sequence
<220> FEATURE:
<223> OTHER INFORMATION: Construct

<400> SEQUENCE: 173

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Gly Ser Gln Val Gln Leu Gln
        115                 120                 125

Gln Ser Gly Ser Glu Leu Met Met Pro Gly Ala Ser Val Lys Ile Ser
130                 135                 140

Cys Lys Ala Thr Gly Tyr Thr Phe Ser Asn Tyr Trp Ile Glu Trp Val
145                 150                 155                 160

Lys Gln Arg Pro Gly His Gly Leu Glu Trp Ile Gly Glu Ile Leu Pro
                165                 170                 175

Gly Thr Gly Arg Thr Ile Tyr Asn Glu Lys Phe Lys Gly Lys Ala Thr
            180                 185                 190

Phe Thr Ala Asp Ile Ser Ser Asn Thr Val Gln Met Gln Leu Ser Ser
        195                 200                 205

Leu Thr Ser Glu Asp Ser Ala Val Tyr Tyr Cys Ala Arg Arg Asp Tyr
    210                 215                 220

Tyr Gly Asn Phe Tyr Tyr Ala Met Asp Tyr Trp Gly Gln Gly Thr Ser
225                 230                 235                 240

Val Thr Val Ser Ser Gly Gly Gly Gly Ser Asp Val Gln Leu Val Gln
```

```
            245                 250                 255
Ser Gly Ala Glu Val Lys Lys Pro Gly Ala Ser Val Lys Val Ser Cys
            260                 265                 270

Lys Ala Ser Gly Tyr Thr Phe Thr Arg Tyr Thr Met His Trp Val Arg
            275                 280                 285

Gln Ala Pro Gly Gln Gly Leu Glu Trp Ile Gly Tyr Ile Asn Pro Ser
            290                 295                 300

Arg Gly Tyr Thr Asn Tyr Ala Asp Ser Val Lys Gly Arg Phe Thr Ile
305                 310                 315                 320

Thr Thr Asp Lys Ser Thr Ser Thr Ala Tyr Met Glu Leu Ser Ser Leu
            325                 330                 335

Arg Ser Glu Asp Thr Ala Thr Tyr Tyr Cys Ala Arg Tyr Tyr Asp Asp
            340                 345                 350

His Tyr Cys Leu Asp Tyr Trp Gly Gln Gly Thr Thr Val Thr Val Ser
            355                 360                 365

Ser Gly Glu Gly Thr Ser Thr Gly Ser Gly Ala Ile Pro Val Ser Leu
            370                 375                 380

Arg Gly Ser Gly Gly Ser Gly Gly Ala Asp Asp Ile Val Leu Thr Gln
385                 390                 395                 400

Ser Pro Ala Thr Leu Ser Leu Ser Pro Gly Glu Arg Ala Thr Leu Ser
            405                 410                 415

Cys Arg Ala Ser Gln Ser Val Ser Ser Ser Tyr Leu Ala Trp Tyr Gln
            420                 425                 430

Gln Lys Pro Gly Gln Ala Pro Arg Leu Leu Ile Tyr Gly Ala Ser Ser
            435                 440                 445

Arg Ala Thr Gly Val Pro Ala Arg Phe Ser Gly Ser Gly Ser Gly Thr
            450                 455                 460

Asp Phe Thr Leu Thr Ile Ser Ser Leu Glu Pro Glu Asp Phe Ala Thr
465                 470                 475                 480

Tyr Tyr Cys Leu Gln Ile Tyr Asn Met Pro Ile Thr Phe Gly Gln Gly
            485                 490                 495

Thr Lys Val Glu Ile Lys His His His His His
            500                 505

<210> SEQ ID NO 174
<211> LENGTH: 403
<212> TYPE: PRT
<213> ORGANISM: Artificial Sequence
<220> FEATURE:
<223> OTHER INFORMATION: Construct

<400> SEQUENCE: 174

Gln Val Lys Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
            50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
            85                  90                  95

Ala Ala Ala Ala Gly Ser Ala Trp Tyr Gly Thr Leu Tyr Glu Tyr Asp
```

Tyr Trp Gly Gln Gly Thr Gln Val Thr Val Ser Ser Gly Gly Gly
                115                 120                 125

Ser Gly Gly Gly Gly Ser Gly Gly Gly Gly Ser Gly Gly Gly Ser
            130                 135                 140

Gly Gly Gly Gly Ser Gly Gly Gly Ser Asp Val Gln Leu Val Gln
145                 150                 155                 160

Ser Gly Ala Glu Val Lys Lys Pro Gly Ala Ser Val Lys Val Ser Cys
                165                 170                 175

Lys Ala Ser Gly Tyr Thr Phe Thr Arg Tyr Thr Met His Trp Val Arg
            180                 185                 190

Gln Ala Pro Gly Gln Gly Leu Glu Trp Ile Gly Tyr Ile Asn Pro Ser
                195                 200                 205

Arg Gly Tyr Thr Asn Tyr Ala Asp Ser Val Lys Gly Arg Phe Thr Ile
            210                 215                 220

Thr Thr Asp Lys Ser Thr Ser Thr Ala Tyr Met Glu Leu Ser Ser Leu
225                 230                 235                 240

Arg Ser Glu Asp Thr Ala Thr Tyr Tyr Cys Ala Arg Tyr Tyr Asp Asp
                245                 250                 255

His Tyr Cys Leu Asp Tyr Trp Gly Gln Gly Thr Thr Val Thr Val Ser
            260                 265                 270

Ser Gly Glu Gly Thr Ser Thr Gly Ser Gly Ser Gly Gly Ser Gly
                275                 280                 285

Gly Ala Asp Asp Ile Val Leu Thr Gln Ser Pro Ala Thr Leu Ser Leu
            290                 295                 300

Ser Pro Gly Glu Arg Ala Thr Leu Ser Cys Arg Ala Ser Gln Ser Val
305                 310                 315                 320

Ser Tyr Met Asn Trp Tyr Gln Gln Lys Pro Gly Lys Ala Pro Lys Arg
                325                 330                 335

Trp Ile Tyr Asp Thr Ser Lys Val Ala Ser Gly Val Pro Ala Arg Phe
            340                 345                 350

Ser Gly Ser Gly Ser Gly Thr Asp Tyr Ser Leu Thr Ile Asn Ser Leu
                355                 360                 365

Glu Ala Glu Asp Ala Ala Thr Tyr Tyr Cys Gln Gln Trp Ser Ser Asn
            370                 375                 380

Pro Leu Thr Phe Gly Gly Gly Thr Lys Val Glu Ile Lys His His His
385                 390                 395                 400

His His His

<210> SEQ ID NO 175
<211> LENGTH: 406
<212> TYPE: PRT
<213> ORGANISM: Artificial Sequence
<220> FEATURE:
<223> OTHER INFORMATION: Construct

<400> SEQUENCE: 175

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Gly Gly Ser Gly Gly
130                 135                 140

Gly Gly Ser Gly Gly Gly Ser Gly Gly Gly Ser Asp Val Gln
145                 150                 155                 160

Leu Val Gln Ser Gly Ala Glu Val Lys Lys Pro Gly Ala Ser Val Lys
                165                 170                 175

Val Ser Cys Lys Ala Ser Gly Tyr Thr Phe Thr Arg Tyr Thr Met His
                180                 185                 190

Trp Val Arg Gln Ala Pro Gly Gln Gly Leu Glu Trp Ile Gly Tyr Ile
            195                 200                 205

Asn Pro Ser Arg Gly Tyr Thr Asn Tyr Ala Asp Ser Val Lys Gly Arg
        210                 215                 220

Phe Thr Ile Thr Thr Asp Lys Ser Thr Ser Thr Ala Tyr Met Glu Leu
225                 230                 235                 240

Ser Ser Leu Arg Ser Glu Asp Thr Ala Thr Tyr Tyr Cys Ala Arg Tyr
                245                 250                 255

Tyr Asp Asp His Tyr Cys Leu Asp Tyr Trp Gly Gln Gly Thr Thr Val
            260                 265                 270

Thr Val Ser Ser Gly Glu Gly Thr Ser Thr Gly Ser Gly Ser Gly
        275                 280                 285

Gly Ser Gly Gly Ala Asp Asp Ile Val Leu Thr Gln Ser Pro Ala Thr
290                 295                 300

Leu Ser Leu Ser Pro Gly Glu Arg Ala Thr Leu Ser Cys Arg Ala Ser
305                 310                 315                 320

Gln Ser Val Ser Tyr Met Asn Trp Tyr Gln Gln Lys Pro Gly Lys Ala
                325                 330                 335

Pro Lys Arg Trp Ile Tyr Asp Thr Ser Lys Val Ala Ser Gly Val Pro
            340                 345                 350

Ala Arg Phe Ser Gly Ser Gly Ser Gly Thr Asp Tyr Ser Leu Thr Ile
        355                 360                 365

Asn Ser Leu Glu Ala Glu Asp Ala Ala Thr Tyr Tyr Cys Gln Gln Trp
    370                 375                 380

Ser Ser Asn Pro Leu Thr Phe Gly Gly Gly Thr Lys Val Glu Ile Lys
385                 390                 395                 400

His His His His His His
            405

<210> SEQ ID NO 176
<211> LENGTH: 412
<212> TYPE: PRT
<213> ORGANISM: Artificial Sequence
<220> FEATURE:
<223> OTHER INFORMATION: Construct

<400> SEQUENCE: 176

Gln Val Lys Leu Glu Glu Ser Gly Gly Gly Ser Val Gln Thr Gly Gly
1               5                   10                  15

-continued

```
Ser Leu Arg Leu Thr Cys Ala Ala Ser Gly Arg Thr Ser Arg Ser Tyr
         20                  25                  30

Gly Met Gly Trp Phe Arg Gln Ala Pro Gly Lys Glu Arg Glu Phe Val
         35                  40                  45

Ser Gly Ile Ser Trp Arg Gly Asp Ser Thr Gly Tyr Ala Asp Ser Val
 50                  55                  60

Lys Gly Arg Phe Thr Ile Ser Arg Asp Asn Ala Lys Asn Thr Val Asp
 65                  70                  75                  80

Leu Gln Met Asn Ser Leu Lys Pro Glu Asp Thr Ala Ile Tyr Tyr Cys
                 85                  90                  95

Ala Ala Ala Ala Gly Ser Ala Trp Tyr Gly Thr Leu Tyr Glu Tyr Asp
             100                 105                 110

Tyr Trp Gly Gln Gly Thr Gln Val Thr Val Ser Ser Gly Gly Gly Gly
         115                 120                 125

Ser Gly Gly Gly Gly Ser Gly Gly Gly Ser Gly Gly Gly Gly Ser
 130                 135                 140

Gly Gly Gly Ser Gly Gly Gly Ser Asp Val Gln Leu Val Gln
145                 150                 155                 160

Ser Gly Ala Glu Val Lys Lys Pro Gly Ala Ser Val Lys Val Ser Cys
                 165                 170                 175

Lys Ala Ser Gly Tyr Thr Phe Thr Arg Tyr Thr Met His Trp Val Arg
             180                 185                 190

Gln Ala Pro Gly Gln Gly Leu Glu Trp Ile Gly Tyr Ile Asn Pro Ser
         195                 200                 205

Arg Gly Tyr Thr Asn Tyr Ala Asp Ser Val Lys Gly Arg Phe Thr Ile
 210                 215                 220

Thr Thr Asp Lys Ser Thr Ser Thr Ala Tyr Met Glu Leu Ser Ser Leu
225                 230                 235                 240

Arg Ser Glu Asp Thr Ala Thr Tyr Tyr Cys Ala Arg Tyr Tyr Asp Asp
                 245                 250                 255

His Tyr Cys Leu Asp Tyr Trp Gly Gln Gly Thr Thr Val Thr Val Ser
             260                 265                 270

Ser Gly Glu Gly Thr Ser Thr Gly Ser Gly Ala Ile Pro Val Ser Leu
         275                 280                 285

Arg Gly Ser Gly Gly Ser Gly Gly Ala Asp Asp Ile Val Leu Thr Gln
 290                 295                 300

Ser Pro Ala Thr Leu Ser Leu Ser Pro Gly Glu Arg Ala Thr Leu Ser
305                 310                 315                 320

Cys Arg Ala Ser Gln Ser Val Ser Ser Ser Tyr Leu Ala Trp Tyr Gln
                 325                 330                 335

Gln Lys Pro Gly Gln Ala Pro Arg Leu Leu Ile Tyr Gly Ala Ser Ser
             340                 345                 350

Arg Ala Thr Gly Val Pro Ala Arg Phe Ser Gly Ser Gly Ser Gly Thr
         355                 360                 365

Asp Phe Thr Leu Thr Ile Ser Ser Leu Glu Pro Glu Asp Phe Ala Thr
 370                 375                 380

Tyr Tyr Cys Leu Gln Ile Tyr Asn Met Pro Ile Thr Phe Gly Gln Gly
385                 390                 395                 400

Thr Lys Val Glu Ile Lys His His His His His
                 405                 410
```

<210> SEQ ID NO 177
<211> LENGTH: 412

<212> TYPE: PRT
<213> ORGANISM: Artificial Sequence
<220> FEATURE:
<223> OTHER INFORMATION: Construct

<400> SEQUENCE: 177

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
            85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser Gly
            115                 120                 125

Gly Gly Gly Ser Gly Gly Gly Ser Gly Gly Gly Ser Gly Gly
130                 135                 140

Gly Gly Ser Gly Gly Gly Ser Gly Gly Gly Ser Asp Ile Val
145                 150                 155                 160

Leu Thr Gln Ser Pro Ala Thr Leu Ser Leu Ser Pro Gly Glu Arg Ala
            165                 170                 175

Thr Leu Ser Cys Arg Ala Ser Gln Ser Val Ser Tyr Met Asn Trp Tyr
            180                 185                 190

Gln Gln Lys Pro Gly Lys Ala Pro Lys Arg Trp Ile Tyr Asp Thr Ser
            195                 200                 205

Lys Val Ala Ser Gly Val Pro Ala Arg Phe Ser Gly Ser Gly Ser Gly
210                 215                 220

Thr Asp Tyr Ser Leu Thr Ile Asn Ser Leu Glu Ala Glu Asp Ala Ala
225                 230                 235                 240

Thr Tyr Tyr Cys Gln Gln Trp Ser Ser Asn Pro Leu Thr Phe Gly Gly
            245                 250                 255

Gly Thr Lys Val Glu Ile Lys Gly Glu Gly Thr Ser Thr Gly Ser Gly
            260                 265                 270

Ala Ile Pro Val Ser Leu Arg Gly Ser Gly Ser Gly Gly Ala Asp
            275                 280                 285

Asp Val Gln Leu Val Gln Ser Gly Ala Glu Val Lys Lys Pro Gly Ala
            290                 295                 300

Ser Val Lys Val Ser Cys Lys Ala Ser Gly Tyr Thr Phe Thr Gly Tyr
305                 310                 315                 320

Tyr Met His Trp Val Arg Gln Ala Pro Gly Gln Gly Leu Glu Trp Met
            325                 330                 335

Gly Trp Ile Asn Pro Asn Ser Gly Gly Thr Asn Tyr Ala Gln Lys Phe
            340                 345                 350

Gln Gly Arg Val Thr Ile Thr Arg Asp Thr Ser Ala Ser Thr Ala Tyr
            355                 360                 365

Met Glu Leu Ser Ser Leu Arg Ser Glu Asp Thr Ala Val Tyr Tyr Cys
            370                 375                 380

```
Ala Arg Asp Phe Leu Ser Gly Tyr Leu Asp Tyr Trp Gly Gln Gly Thr
385                 390                 395                 400

Leu Val Thr Val Ser Ser His His His His His His
                405                 410

<210> SEQ ID NO 178
<211> LENGTH: 9
<212> TYPE: PRT
<213> ORGANISM: Artificial Sequence
<220> FEATURE:
<223> OTHER INFORMATION: HLA-A*0201-restricted viral peptide

<400> SEQUENCE: 178

Asn Leu Val Pro Met Val Ala Thr Val
1               5
```